US009439595B2

(12) United States Patent
Leininger et al.

(10) Patent No.: US 9,439,595 B2
(45) Date of Patent: *Sep. 13, 2016

(54) METHOD AND APPARATUS FOR DETECTING SEIZURES

(71) Applicant: Brain Sentinel, Inc., San Antonio, TX (US)

(72) Inventors: James R. Leininger, San Antonio, TX (US); Russell M. Herring, San Antonio, TX (US); Michael R. Girouard, San Antonio, TX (US); Jose E. Cavazos, San Antonio, TX (US)

(73) Assignee: Brain Sentinel, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/659,317

(22) Filed: Mar. 16, 2015

(65) Prior Publication Data

US 2015/0250415 A1    Sep. 10, 2015

Related U.S. Application Data

(63) Continuation of application No. 13/275,309, filed on Oct. 17, 2011, now Pat. No. 8,983,591.

(51) Int. Cl.
| | |
|---|---|
| *A61B 5/0488* | (2006.01) |
| *A61B 5/00* | (2006.01) |
| *A61B 5/0402* | (2006.01) |
| *A61B 5/04* | (2006.01) |
| *A61B 5/01* | (2006.01) |
| *A61B 5/11* | (2006.01) |

(52) U.S. Cl.
CPC ............ *A61B 5/4094* (2013.01); *A61B 5/0004* (2013.01); *A61B 5/01* (2013.01); *A61B 5/0402* (2013.01); *A61B 5/04015* (2013.01); *A61B 5/0488* (2013.01); *A61B 5/11* (2013.01); *A61B 5/6804* (2013.01); *A61B 5/6844* (2013.01); *A61B 2505/07* (2013.01); *A61B 2562/0219* (2013.01)

(58) Field of Classification Search
CPC ............ A61B 5/0004; A61B 5/04015; A61B 5/0488; A61B 5/4094
USPC ........................................................ 600/546
See application file for complete search history.

(56) References Cited

U.S. PATENT DOCUMENTS 8,983,591 B2 *   3/2015   Leininger ............ A61B 5/0004
                                                                600/546

* cited by examiner

*Primary Examiner* — Lee S Cohen
*Assistant Examiner* — Emily Lloyd
(74) *Attorney, Agent, or Firm* — The Pizarro Firm

(57) ABSTRACT

A method of detecting seizures may comprise receiving an EMG signal and processing the received EMG signal to determine whether a seizure characteristic is present in the EMG signal during a time window. An apparatus for detecting seizures with motor manifestations may comprise one or more EMG electrodes capable of providing an EMG signal substantially representing seizure-related muscle activity; and a processor configured to receive the EMG signal, process the EMG signal to determine whether a seizure may be occurring, and generate an alert if a seizure is determined to be occurring based on the EMG signal.

15 Claims, 37 Drawing Sheets

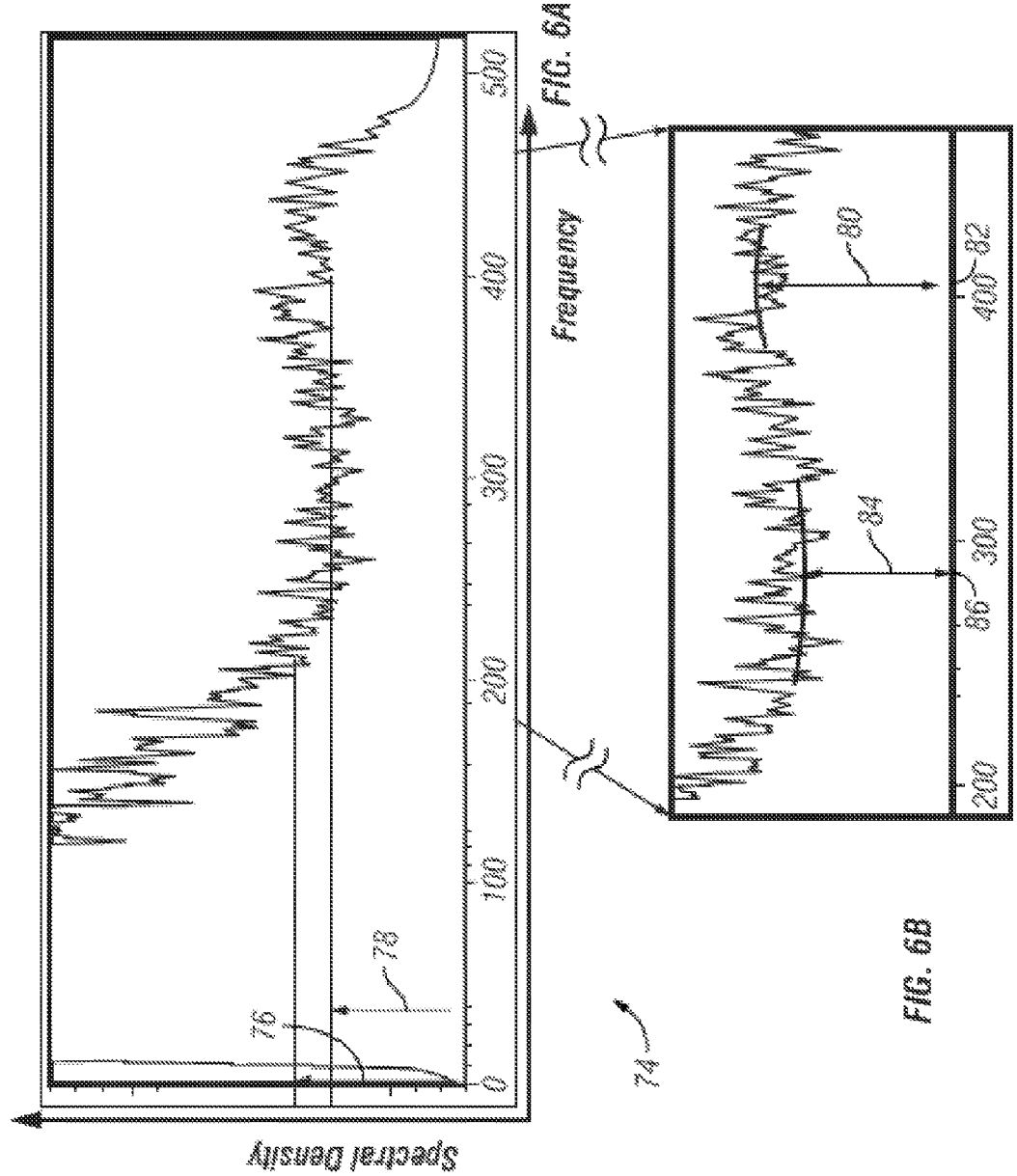

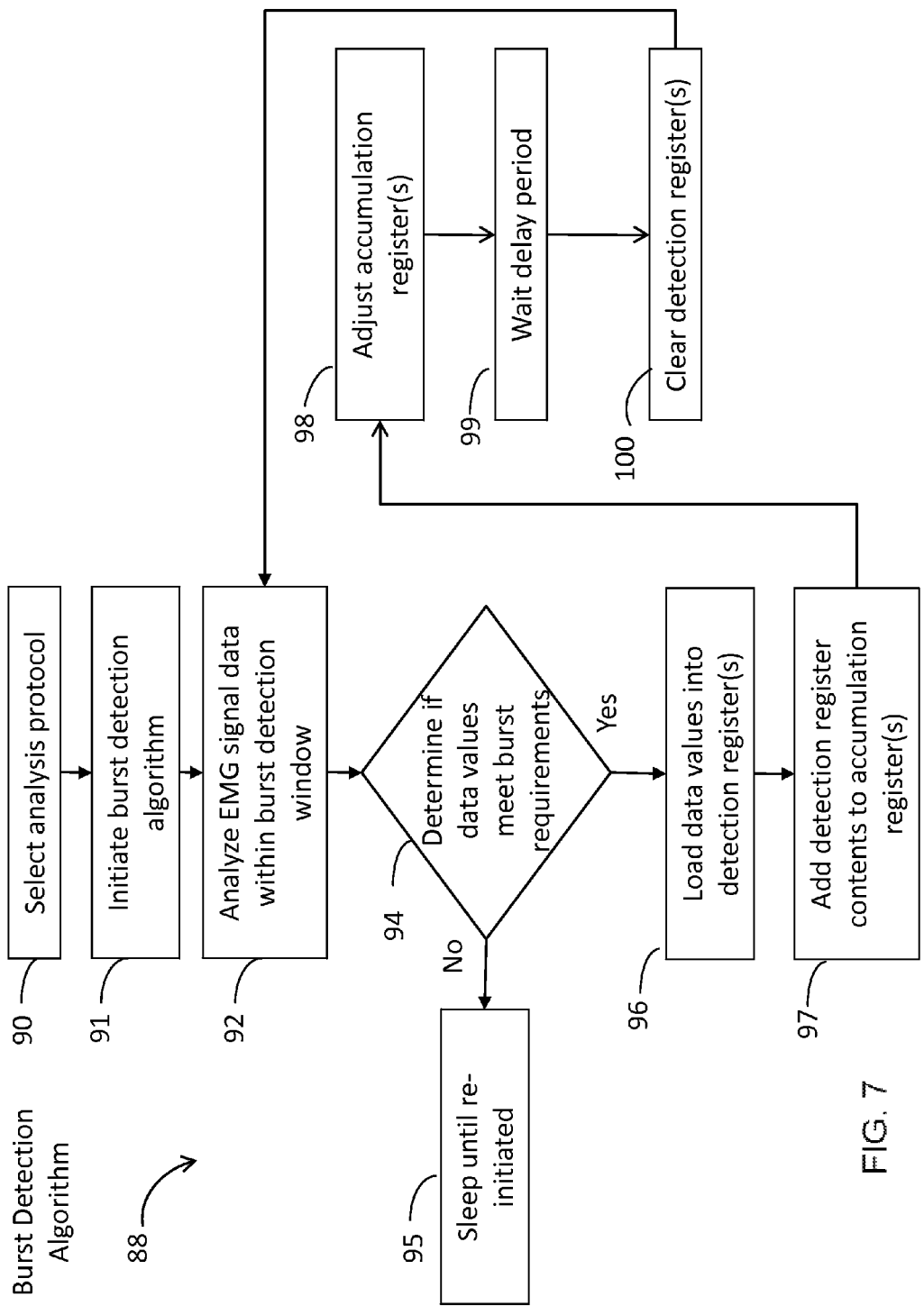

Waveform Regularity Detection Algorithm

154 ↘

156 — Measure amplitude and burst widths looking for very regular waveforms

↓

158 — If waveforms appear to be too uniform in amplitude or burst width, increment the Regularity Accumulation register periodically

↓

160 — If the waveforms' regularity decreases, then decrement the Regularity Accumulation Register periodically

218 — Wake up periodically and measure the EMG signal amplitude

220 — If amplitude is above threshold, stay awake and continue to measure. If not, go back to sleep.

FIG. 18

METHOD AND APPARATUS FOR DETECTING SEIZURES

PRIORITY DATA

This application is a continuation of U.S. patent application Ser. No. 13/275,309 filed Oct. 17, 2011, which issued as U.S. Pat. No. 8,983,591 on Mar. 17, 2015, and claims priority from U.S. Provisional Application No. 61/393,747, filed Oct. 15, 2010, the disclosures of which are each incorporated herein by reference.

BACKGROUND

A seizure may be characterized as abnormal or excessive synchronous activity in the brain. At the beginning of a seizure, neurons in the brain may begin to fire at a particular location. As the seizure progresses, this firing of neurons may spread across the brain, and in some cases, many areas of the brain may become engulfed in this activity. Seizure activity in the brain may cause the brain to send electrical signals through the peripheral nervous system to different muscles. For example, an electrical signal may originate in the central nervous system and initiate the propagation of an electrical signal through motor neurons. A motor neuron may, for example, communicate with a muscle through interaction with the motor end plate of a muscle fiber; thereby initiating an action potential and depolarization of muscle cells within a given motor unit. Depolarization typically results from the coordinated flow of ions, e.g., sodium and potassium cations, through channels within a muscle cell membrane. That is, changes in states of ion channels initiate a change in the permeability of a cell membrane, and subsequent redistribution of charged ions. Current flow through muscle cells may initiate a corresponding flow in the tissue above the muscle and thus an electrical signature at the surface of the skin.

Techniques designed for studying and monitoring seizures have typically relied upon electroencephalography (EEG), which characterizes electrical signals using electrodes attached to the scalp or head region of a seizure prone individual, or seizure patient. EEG electrodes may be positioned so as to measure such activity, that is, electrical activity originating from neuronal tissue. Compared to EEG, electromyography (EMG) is a little-used technique in which an electrode may be placed on or near the skin, over a muscle, to detect an electrical current or change in electric potential in response to redistribution of ions within muscle fibers.

Detecting an epileptic seizure using electroencephalography (EEG) typically requires attaching many electrodes and associated wires to the head and using amplifiers to monitor brainwave activity. The multiple EEG electrodes may be very cumbersome and generally require some technical expertise to apply and monitor. Furthermore, confirming a seizure requires observation in an environment provided with video monitors and video recording equipment. Unless used in a staffed clinical environment, such equipment is frequently not intended to determine if a seizure is in progress but rather provide a historical record of the seizure after the incident. Such equipment is usually meant for hospital-like environments where a video camera recording or caregiver's observation may provide corroboration of the seizure, and is typically used as part of a more intensive care regimen such as a hospital stay for patients who experience multiple seizures. A hospital stay may be required for diagnostic purposes or to stabilize a patient until suitable medication can be administered. Upon discharge from the hospital, a patient may be sent home with little further monitoring. However, at any time after being sent home the person may experience another seizure, perhaps fatal.

A patient should in some cases be monitored at home for some length of time in case another seizure should occur. Seizures with motor manifestations may have patterns of muscle activity that include rhythmic contractions of some, most, or all of the muscles of the body. A seizure could, for example, result in Sudden Unexplained Death in Epilepsy (SUDEP). The underlying causes of SUDEP are not well understood; however, some possible mechanisms causing SUDEP may include tonic activation of the diaphragm muscle so as to prevent breathing, neurogenic pulmonary edema, asystole, and other cardiac dysrhythmia. If a sleeping person experiences a seizure involving those conditions, then caregivers may not be aware that the seizure is occurring, and thus be unable to render timely aid.

While there presently exist ambulatory devices for diagnosis of seizures, they are EEG-based and are generally not designed or suitable for long-term home use or daily wearability. Other seizure alerting systems may operate by detecting motion of the body, usually the extremities. Such systems may generally operate on the assumption that while suffering a seizure, a person will move erratically and violently. For example, accelerometers may be used to detect violent extremity movements. However, depending upon the type of seizure, this assumption may or may not be true. Electrical signals sent from the brain during the seizure are frequently transmitted to many muscles simultaneously, which may result in muscles fighting each other and effectively canceling out violent movement. In other words, the muscles may work to make the person rigid rather than cause actual violent movement. Thus, the seizure may not be consistently detected with accelerometer-based detectors.

Accordingly, there is a need for an epileptic seizure detection method and apparatus that can be used in a non-institutional or institutional environment without many of the cumbersome electrodes to the head or extremities. Such an apparatus may be minimally intrusive, minimally interfere with daily activities and be comfortably used while sleeping. There is also a need for an epileptic seizure detection method and apparatus that accurately detects a seizure with motor manifestations and may alert one or more local and/or remote sites of the presence of a seizure. Furthermore, there is a need for an epileptic seizure detection method and apparatus that may be used in a home setting and which may provide robust seizure detection, even in the absence of violent motion, and which may be personalizable, e.g., capable of being tailored for an individual or specific population demographic.

SUMMARY

In some embodiments, a method of detecting seizures may comprise receiving an EMG signal and processing the received EMG signal to determine whether a seizure characteristic is present in the EMG signal during a time window.

In some embodiments, an apparatus for detecting seizures with motor manifestations may comprise one or more EMG electrodes capable of providing an EMG signal substantially representing seizure-related muscle activity; and a processor configured to receive the EMG signal, process the EMG signal to determine whether a seizure may be occurring, and generate an alert if a seizure is determined to be occurring based on the EMG signal.

In some embodiments, apparatuses and methods comprise a detection unit which includes EMG electrodes and a base unit in communication and physically separated from said detection unit, wherein the base station is configured for receiving and processing EMG signals from the detection unit, determining from the processed EMG signals whether a seizure may have occurred, and sending an alert to at least one caregiver. In some embodiments, the base station may separately process the data provided by the detection unit for verification of the alarm condition. If the base station agrees with the alarm, then the base station may generate an alarm to remote devices and local sound generators. Having the base station agree to the detection unit's alarm may introduce a voting concept. Both devices must vote on the decision and agree to sound the alarm. This may be used to limit false alarms.

In some embodiments, a method and apparatus for detecting a seizure and providing a remote warning of that incident is provided. Such a method may detect seizures using EMG electrodes. One or more EMG electrodes may be attached to an individual's body and one or more characteristics from the signal output of the one or more EMG electrodes may be analyzed. EMG output may be compared to general seizure characteristics and to one or more threshold values. If one or more values of the output data exceed one or more thresholds an event may be registered, e.g., logged on a register. Analysis of events logged in registers for different characteristics of the output data may be used to assess whether a seizure incident is declared and whether an alarm is sent to one or more locations.

In some embodiments, an apparatus for detecting seizures with motor manifestations may include a detector unit and a base unit. The detector unit may include one or more electromyography (EMG) electrodes, and optionally one or more electrocardiography (ECG) electrodes. The detector unit and base unit may be in communication with each other, such as by wireless communication. The detector unit and base unit may include electronic components configured to execute instructions for evaluation of EMG signal data. The base unit may be enabled for sending an alarm to one or more remote locations. Alternatively, the base unit may be in communication with a separate transceiver. That transceiver may be physically distinct but within the general locale of the base unit. That transceiver may be enabled for sending an alarm to one or more remote locations.

In some embodiments, an alarm protocol may be initiated based on a convolution of data in a plurality of data registers. Individual registers may, for example, each be responsive to detection of a different seizure variable. An alarm protocol may be initiated if a supervisory algorithm, that supervisory algorithm responsive to the values in the plurality of registers, determines that an alarm protocol should be initiated.

In some embodiments, seizure detection methods as described herein may be adaptive. For example, threshold values may be adjusted as seizure data is collected from one or more patients. In addition, algorithms, which may be used to determine whether a seizure incident is declared, may be modified. Algorithms may, for example, be modified by adjusting variable coefficients. Those coefficients may be associated with, and weight, seizure variables. The adjustment of such coefficients may be based on seizure data that is collected from one or more patients, including, but not limited to an individual patient, or other patients, such as those of a particular demographic. The association between registered events, the initiation of alarm protocols, and seizure related incidents, e.g., declared events, actual seizures and inaccurately reported incidents, may be tracked and used to update variables in a detection method and thus improve the accuracy of a seizure detection method or apparatus.

In some embodiments, a historical record of patient seizure data and related incidents may be collected. A user may analyze a historical record and modify or change one or more sub-methods or alter the distribution of sub-methods that are included in a method for detecting a seizure. A sub-method may, for example, be a set of instructions which may be used to increment a counter. Sub-methods may include data, including for example, threshold values, weighting coefficients and other data, may be provided in a template file, may have a "factory default" setting, and may change as the method adapts to a particular patient.

In some embodiments, the value of a plurality of seizure variables may be determined for a patient. Individual seizure variables may be selected and analyzed using algorithms such that events logged for an individual seizure variable is unlikely to trigger an alarm; however, the convolution of events logged for the plurality of seizure variables may raise the confidence with which a seizure may be detected.

In some embodiments, a method and apparatus may be used, for example, to initiate an alarm protocol, create a log of seizure incidents to help medically or surgically manage the patient, activate a Vagal Nerve Stimulator, or activate other stimulating devices that may be used to abort or attenuate a seizure. In some embodiments, a log of seizure related incidents may prompt a physician to understand more quickly the failure of a treatment regimen.

BRIEF DESCRIPTION OF THE DRAWINGS

FIG. 6A and FIG. 6B illustrate exemplary EMG frequency domain data for a patient.

FIG. 7 illustrates one embodiment of a burst detection algorithm.

FIG. 13 illustrates one embodiment of a waveform regularity detection algorithm.

FIG. 18 illustrates one embodiment of an amplitude detection algorithm.

DETAILED DESCRIPTION

The apparatuses and methods described herein may be used to detect seizures and timely alert caregivers of a seizure using EMG, among other things. The apparatuses and method may be used, for example, to initiate an alarm protocol, create a log of seizure incidents to help medically or surgically manage the patient, activate a Vagal Nerve Stimulator, or activate other stimulating devices that may be used to abort or attenuate a seizure. In some embodiments, a log of seizure related incidents may prompt a physician to understand more quickly the failure of a treatment regimen. The apparatuses and methods may comprise a process and device and/or system of devices for detecting seizures with motor manifestations including, but not limited to Tonic-Clonic, Tonic-only, or Clonic-only seizures. A "motor manifestation" may in some embodiments generally refer to muscle activity, whether sustained or otherwise.

Apparatuses as described herein may be useful for monitoring a person to determine whether the person may be having a seizure, and for initiating an alarm. The methods described herein may be flexible, e.g., such methods may be customized for an individual. Moreover, such methods may be adaptive, and may improve as data is collected, e.g., for a given patient or for a certain patient demographic. Furthermore, apparatuses described herein may be suited for organizing and/or prioritizing the collection of large amounts of data, e.g., data that may be collected in a substantially continuous manner, such as while a seizure-prone individual is in a home setting.

In general terms, EMG electrode signals may be collected and processed to determine seizure variables. A "seizure variable" may in some embodiments refer to a criterion or criteria of one or more portions of data collected from the output signal of a detector. For a given set of data, a seizure variable may have one or more numerical values associated with it. For example, the amplitude of a signal may be a seizure variable that may have one or more numerical values associated with it for a given set of data. A value of a seizure variable may be compared to a threshold level and may be used as an input in an algorithm for determining whether a seizure may have occurred.

A processing method may include calculating one or more seizure variable values and may further include comparing such values to one or more thresholds that may characterize a seizure. Data registers may be populated based upon such a comparison, and used to evaluate whether to initiate an alarm protocol. The weighting of data in different registers, and thus the importance of different characteristics of EMG data, may be customized for an individual patient or patient demographic, and may adapt as the system obtains more information for a patient or patient demographic.

Figure 1:
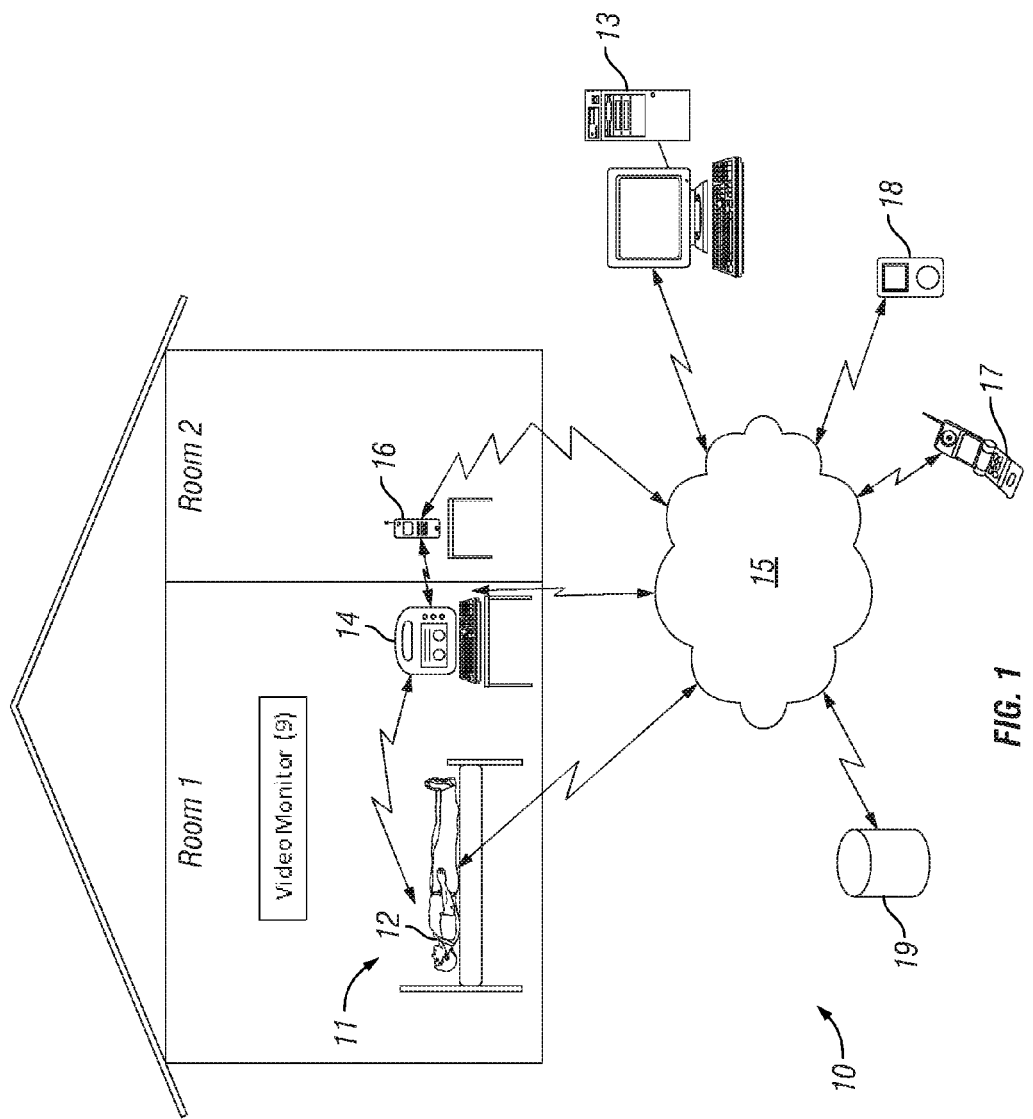
FIG. 1 illustrates one embodiment of a seizure detection system.

A variety of suitable systems may be suitable for collecting large amounts of EMG and other patient-related data, organizing such data for system optimization, and for initiating an alarm in response to a suspected seizure. FIG. 1 illustrates an exemplary embodiment of such a system. In the embodiment of FIG. 1, a seizure detection system 10 may include a detection unit 12, an optional base station 14, an optional video monitor 9 and an optional alert transceiver 16. The detection unit may comprise one or more EMG electrodes capable of detecting electrical signals from muscles at or near the skin surface of a patient, and delivering those electrical EMG signals to a processor for processing. The base station may comprise a computer capable of receiving and processing EMG signals from the detection unit, determining from the processed EMG signals whether a seizure may have occurred, and sending an alert to a caregiver. An alert transceiver may be carried by, or placed near, a caregiver to receive and relay alerts transmitted by the base station.

In using the apparatus of FIG. 1, for example, a person 11 susceptible to epileptic seizures may be resting in bed, or may be at some other location as daily living may include, and may have a detection unit 12 in physical contact with or in proximity to his or her body. The detection unit 12 may be a wireless device so that a person may be able to get up and walk around without having to be tethered to an immobile power source or to a bulkier base station 14. For example, the detection unit 12 may be woven into a shirt sleeve, or may be mounted to an armband or bracelet. In other embodiments, one or more detection units 12 may be placed or built into a bed, a chair, an infant car seat, or other suitable clothing, furniture, equipment and accessories used by those susceptible to seizures. The detection unit 12 may comprise a simple sensor, such as an electrode, that may send signals to the base station for processing and analysis, or may comprise a "smart" sensor having some data processing and storage capability. In some embodiments, a simple sensor may be connected via wire or wirelessly to a battery-operated transceiver mounted on a belt worn by the person.

The system may monitor the patient, for example, while resting, such as during the evening and nighttime hours. If the detection unit 12 on the patient detects a seizure, the detection unit 12 may communicate via wire or wirelessly, e.g., via a communications network or wireless link, with the base station 14 and may send some signals to the base station device for more thorough analysis. For example, the detection unit 12 may process and use EMG signals (and optionally ECG and temperature sensor signals) to make an initial assessment regarding the likelihood of occurrence of a seizure, and may send those signals and its assessment to the base station 14 for separate processing and confirmation. If the base station 14 confirms that a seizure is likely occurring, then the base station 14 may initiate an alarm for transmission over the network 15 to alert a caregiver by way of email, text, or any suitable wired or wireless messaging indicator. In some embodiments, if one or more of the detection unit 12, the base station 14, or a caregiver, e.g., a remotely located caregiver monitoring signals provided from the base station, determines that a seizure may be occurring, a video monitor 9 may be triggered to collect information.

The base station 14, which may be powered by a typical household power supply and contain a battery for backup, may have more processing, transmission and analysis power available for its operation than the detection unit 12, may be able to store a greater quantity of signal history, and evaluate a received signal against that greater amount of data. The base station 14 may communicate with an alert transceiver 16 located remotely from the base station 14, such as in the bedroom of a family member, or to a wireless device 17, 18 carried by a caregiver or located at a work office or clinic. The base station 14 and/or transceiver 16 may send alerts or messages to caregivers, or medical personnel via any suitable means, such as through a network 15 to a cell phone 17, personal digital assistant (PDA) 18 or other client device. The system 10 may thus provide an accurate log of seizures, which may allow a patient's physician to understand more quickly the success or failure of a treatment regimen. Of course, the base station 14 may simply comprise a computer having installed a program capable of receiving, processing and analyzing signals as described herein, and capable of transmitting an alert. In other embodiments, the system 10 may simply comprise, for example, EMG electrodes and a smartphone, such as an iPhone, configured to receive EMG signals from the electrodes for processing the EMG signals as described herein using an installed program application. In further embodiments, so-called "cloud" computing and storage may be used via network 15 for storing and processing the EMG signals and related data. In yet other embodiments, one or more EMG electrodes could be packaged together as a single unit with a processor capable of processing EMG signals as disclosed herein and sending an alert over a network. In other words, the apparatus may comprise a single item of manufacture that may be placed on a patient and that does not require a base station separate transceiver.

In the embodiment of FIG. 1, the signal data may be sent to a remote database 19 for storage. In some embodiments, signal data may be sent from a plurality of epileptic patients to a central database 19 and "anonymized" to provide a basis for establishing and refining generalized "baseline" sensitivity levels and signal characteristics of an epileptic seizure.

The database 19 and base station 14 may be remotely accessed via network 15 by a remote computer 13 to allow updating of detector unit and/or base station software, and data transmission. The base station 14 may generate an audible alarm, as may a remote transceiver 16. All wireless links may be two-way for software and data transmission and message delivery confirmation. The base station 14 may also employ one or all of the messaging methods listed above for seizure notification. The base station 14 may provide an "alert cancel" button to terminate the incident warning.

In some embodiments, a transceiver may additionally be mounted within a unit of furniture or some other structure, e.g., an environmental unit or object. If a detection unit is sufficiently close to that transceiver, such a transceiver may be capable of sending data to a base station. Thus, the base station may be aware that information is being received from that transducer, and therefore the associated environmental unit. In some embodiments, a base station may select a specific template file, e.g., such as including threshold values and other data as described further herein, that is dependent upon whether or not it is receiving a signal from a certain transceiver. Thus, for example, if the base station receives information from a detector and from a transducer that is associated with a bed or crib it may treat the data differently than if the data is received from a transducer associated with another environmental unit, such as, for example, clothing typically worn while an individual may be exercising The embodiment of FIG. 1 may be configured to be minimally intrusive to use while sleeping or minimally interfere in daily activities, may require a minimum of electrodes such as one or two, may require no electrodes to the head, may detect a seizure with motor manifestations, may alert one or more local and/or remote sites of the presence of a seizure, and may be inexpensive enough for home use.

Figure 2:
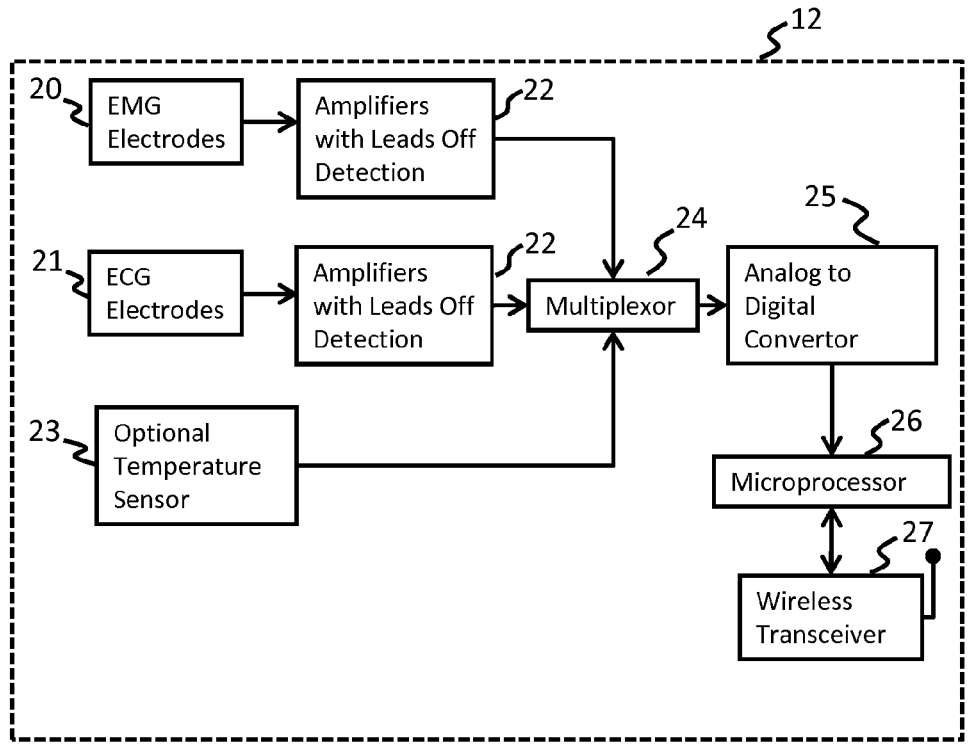
FIG. 2 illustrates one embodiment of a detection unit and base station for a seizure detection system.

FIG. 2 illustrates an embodiment of a detection unit 12 or detector. The detection unit 12 may include EMG electrodes 20, and may also include ECG electrodes 21. The detection unit 12 may further include amplifiers with leads-off detectors 22. In some embodiments, one or more leads-off detectors may provide signals that indicate whether the electrodes are in physical contact with the person's body, or otherwise too far from the person's body to detect muscle activity, temperature, brain activity or other patient phenomena.

The detection unit 12 may further include a temperature sensor 23 to sense the person's temperature. Other sensors (not shown) may be included in the detection unit as well, such as accelerometers. Signals from electrodes 20 and 21, temperature sensor 23 and other sensors may be provided to a multiplexor 24. The multiplexor 24 may be part of the detection unit 12 or may be part of the base station 14 if the detection unit 12 is not a smart sensor. The signals may then be communicated from the multiplexor 24 to one or more analog-to-digital (A-D) converters 25. The analog-to-digital converters may be part of the detection unit 12 or may be part of the base station 14. The signals may then be communicated to one or more microprocessors 26 for processing and analysis as disclosed herein. The microprocessors 26 may be part of the detection unit 12 or may be part of the base station 14. The detection unit 12 and/or base station 14 may further include memory of suitable capacity. The microprocessor 26 may communicate signal data and other information using a transceiver 27. Communication by and among the components of the detection unit 12 and/or base station 14 may be via wired or wireless communication.

Of course, the exemplary detection unit of FIG. 2 may be differently configured. Many of the components of the detector of FIG. 2 may be in base station 14 rather than in the detection unit 12. For example, the detection unit may simply comprise an EMG electrode 20 in wireless communication with a base station 14. In such an embodiment, A-D conversion and signal processing may occur at the base station 14. If an ECG electrode 21 is included, then multiplexing may also occur at the base station 14.

In another example, the detection unit 12 of FIG. 2 may comprise an electrode portion having one or more of the EMG electrode 20, ECG electrode 21 and temperature sensor 23, in wired or wireless communication with a small belt-worn transceiver portion. The transceiver portion may include a multiplexor 24, an A-D converter 25, microprocessor 26, transceiver 27 and other components, such as memory and input/output (I/O) devices (e.g., alarm cancel buttons and visual display).

Figure 3:
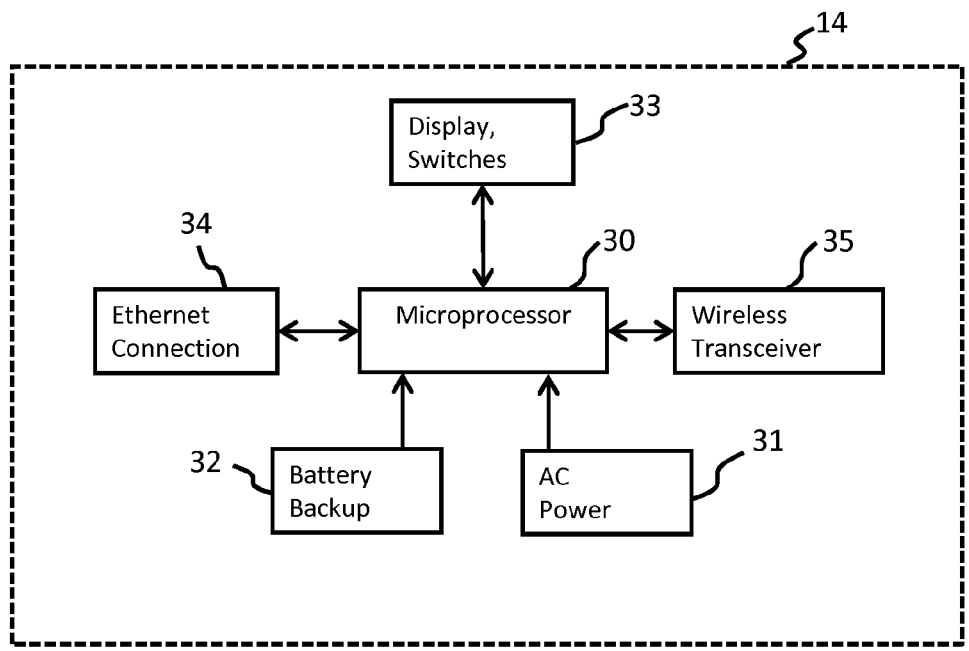
FIG. 3 illustrates one embodiment of a base station.

FIG. 3 illustrates an embodiment of a base station 14 that may include one or more microprocessors 30, a power source 31, a backup power source 32, one or more I/O devices 33, and various communications means, such as an Ethernet connection 34 and transceiver 35. The base station 14 may have more processing and storage capability than the detection unit 12, and may include a larger electronic display for displaying EMG signal graphs for a caregiver to review EMG signals in real-time as they are received from the detection unit 12 or historical EMG signals from memory. The base station 14 may process EMG signals and other data received from the detection unit 12. If the base station 14 determines that a seizure is likely occurring, it may send an alert to a caregiver via transceiver 35.

Various devices in the apparatus of FIGS. 1-3 may communicate with each other via wired or wireless communication. The system 10 may comprise a client-server or other architecture, and may allow communication via network 15. Of course, the system 10 may comprise more than one server and/or client. In other embodiments, the system 10 may comprise other types of network architecture, such as a peer-to-peer architecture, or any combination or hybrid thereof.

Figure 4:
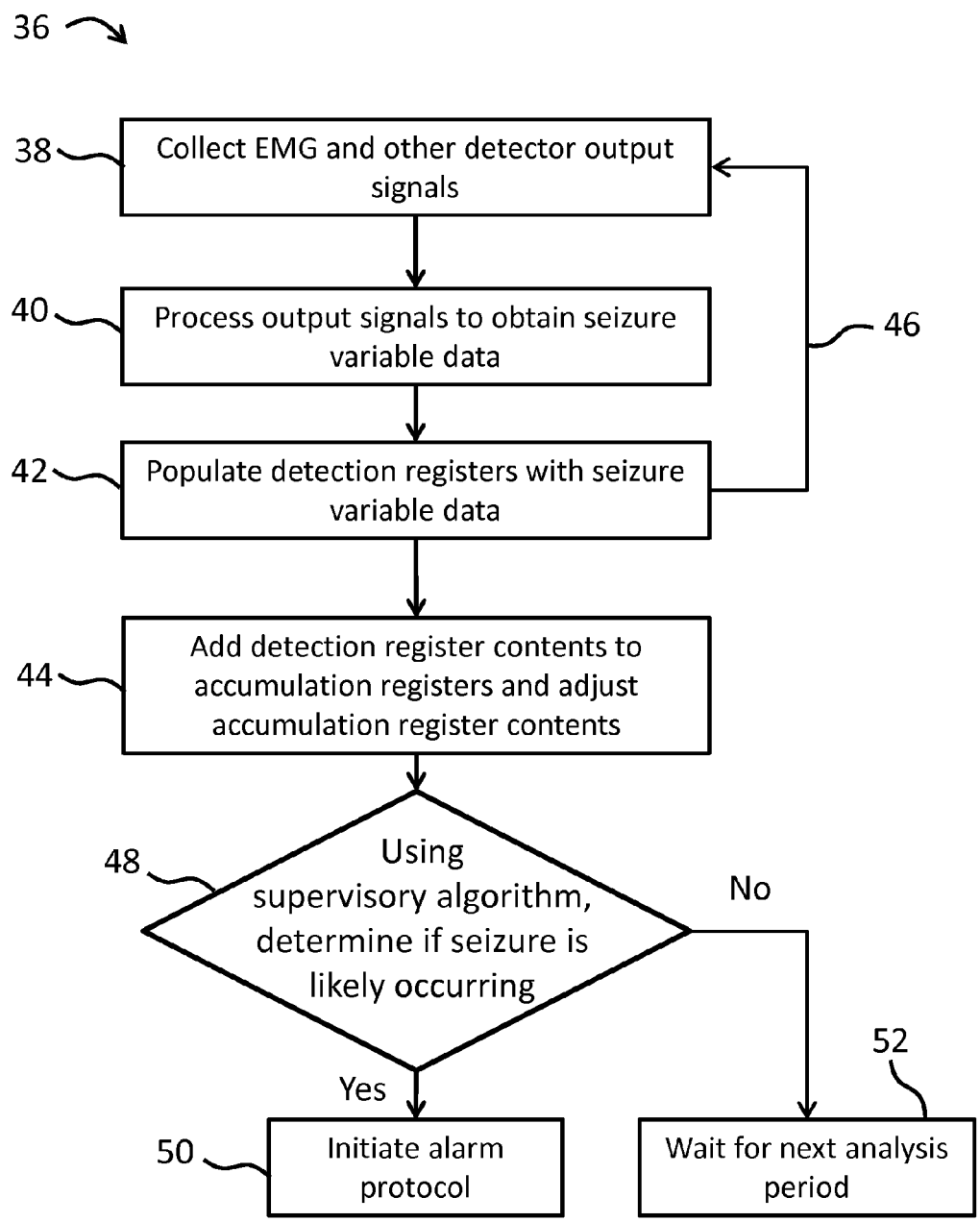
FIG. 4 illustrates one embodiment of a method for detecting seizure related incidents.

FIG. 4 illustrates an exemplary method 36 of monitoring EMG and other signals for seizure characteristics, and initiating an alarm response if a seizure is detected. Such a method may involve collecting of EMG signals, calculating one or more values of a seizure variable, and using such seizure variable data to populate processor or memory registers. In general, one or more seizure variables and one or more registers may be included in data analysis. In a step 38, EMG signals and other detector output signals may be collected. Output signals may be collected in a substantially continuous manner or periodically. Output signals may be processed in a step 40 to obtain seizure variable data. The data values may be used to populate one or more detection registers, as shown in step 42. Processing of output signals and population of detection registers may be executed during a defined period of time, i.e., collection time window. At the expiration of such a collection time window, each detection register may transfer its contents, if any, to one or more accumulation registers (as shown in step 44), and the contents of one or more detection registers, if any, may be cleared. After expiration of the collection time window, and after adjustment (increase or leakage) of accumulation registers, the cycle may repeat itself (as shown by line 46), i.e., detector output may be collected during a subsequent collection window. Periodically, a supervisory algorithm may analyze the contents of one or more accumulation registers to determine whether a seizure is likely occurring (step 48).

If the supervisory algorithm determines that the sum of values or a weighted sum of values in the accumulation registers exceeds a threshold then an alarm protocol may be initiated (step 50). Alternatively, the supervisory register may determine that the contents of accumulation registers do not indicate that a seizure is likely and the system may wait for a next analysis period (step 52).

As discussed below, a supervisory algorithm may comprise a number of sub-routines that use various seizure variable values in the accumulation and/or detection registers. As shown by way of example in FIG. 4, methods may involve the population of individual detection registers with a data value and addition of such a data value to accumulation registers (steps 38, 40, 42, and 44). A sub-method may include steps involved in the population of individual detection registers and accumulation registers. Each sub-method may consider one or more characteristics of the collected data and perform process analysis on such characteristics. Individual sub-methods may include, by way of nonlimiting example, detection of signal bursts and detection of GTC waveforms. Sub-methods may process data in the time domain, the frequency domain, or, in some embodiments, process portions of data in both the time domain and frequency domain. Before discussion of those individual sub-methods in greater detail, it is helpful to consider some general aspects of data collection, the detectors used, as well as processing steps, such as data filtration that may be involved in various sub-methods. In addition, it is instructive to discuss exemplary EMG signal data, as shown in FIGS. 5A, 5B, 6A, and 6B discussed in more detail further herein.

As indicated in step 38 of FIG. 4, in some embodiments, detection of seizures may be accomplished exclusively by analysis of EMG electrode data. In other embodiments, a combination of EMG and other detectors may be used. For example, temperature sensors, accelerometers, ECG detectors, other detectors, or any combinations thereof, may be used. Accelerometers may, for example, be placed on a patient's extremities to detect the type of violent movement that may characterize a seizure. Similarly, ECG sensors may be used to detect raised or abnormal heart rates that may characterize a seizure. Thus, a monitoring device may detect an epileptic seizure without the customary multitude of wired electrodes attached to the head, as typical with EEG. Combination of EMG electrodes with other detectors may, for example, be used with particularly difficult patients. Patients with an excessive amount of loose skin or high concentrations of adipose tissue, which may affect the stability of contact between an electrode and the skin, may be particularly difficult to monitor. In some embodiments, an electrode may be attached to a single muscle, and in other embodiments a combination of two or more electrodes may be used. Electrodes may, for example, be attached to an agonist and antagonist muscle group or signals from other combinations of different muscles may be collected.

In general, the system described herein is compatible with any type of EMG electrode, such as, for example, surface monopolar electrodes or bipolar differential electrodes or electrodes of any suitable geometry. Such electrodes may, for example, by positioned on the surface of the skin, may or may not include application of a gel, and may, in some embodiments, be Ag/AgCl electrodes. The use of a bipolar EMG electrode arrangement, e.g., with a reference lead and two surface inputs, allows for the suppression of noise that is common to those inputs. That is, a differential amplifier may be used, and a subtraction of the signals from one input with respect to the other may be accomplished, and any differences in signal between the inputs amplified. In such an approach, signals that are common to both inputs (such as external noise) may be substantially nullified and preferential amplification of signals originating from muscle depolarization may be achieved.

An EMG signal may be collected for a given time period, e.g., a time domain electrode signal may be collected. Time domain electrode data, may be converted to frequency data, i.e., spectral content, using techniques such as Fast-Fourier Transform (FFT). In reference to FIG. 4, the conversion of data between the time and frequency domain may be included in a processing step 40. Other aspects of data processing may include smoothing data, application of one or more frequency filters, fitting data in a given region to a particular function, and other processing operations FIGS. 5A and 5B (collectively referred to as FIG. 5) provide examples of EMG data 54 collected over a time period of about 2 seconds. The data in FIG. 5 may exemplify data collected by placing a bipolar differential electrode over the biceps or triceps of a patient. FIGS. 6A and 6B (collectively referred to as FIG. 6) illustrate some of the EMG data 54 of FIG. 5 converted to the frequency domain. The EMG data 74 in FIG. 6 may represent, for example, a one-second epoch of the EMG data 54 converted to the frequency domain. For an EMG electrode, visual representation of frequency domain data may also be referred to as a spectral graph.

Figure 5A:
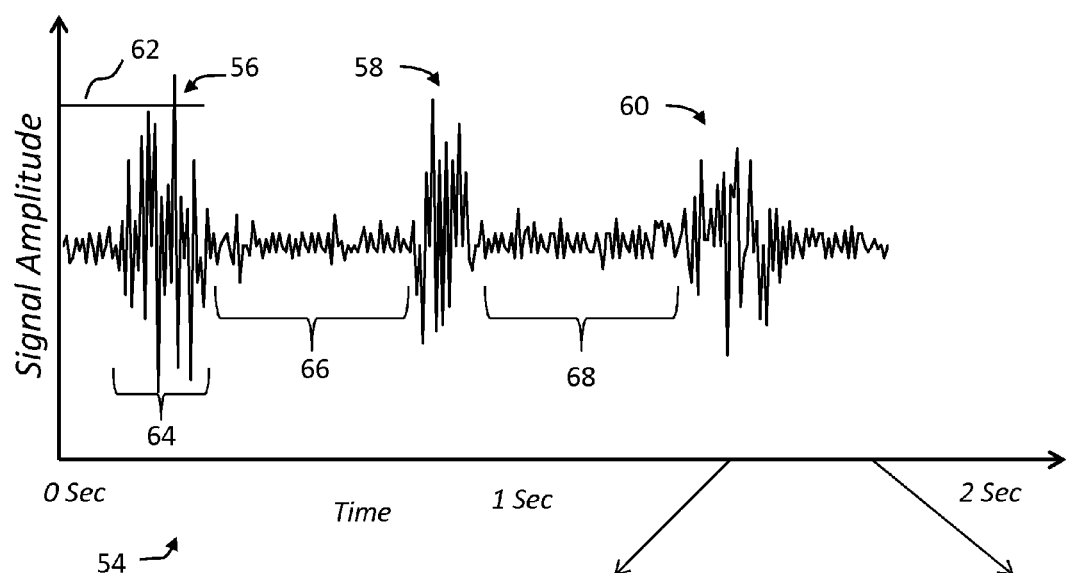
FIG. 5A and FIG. 5B illustrate exemplary EMG time domain data for a patient.
Figure 5B:
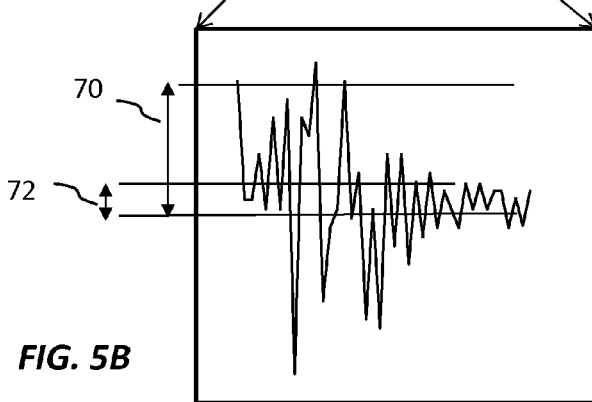

Referring now to the time domain data for the graph of FIG. 5, the vertical axis or scale in FIG. 5A is signal amplitude, e.g., the differential signal between the pair of EMG electrode inputs, and the horizontal axis or scale shows time (in FIG. 5, the time window is approximately two seconds). In reference to any of the graphs described herein the term amplitude may be used, and such may refer to either the magnitude of signal, or absolute value of magnitude, as may be appropriate for a given calculation. Signals collected may, for example, be rectified, and unless otherwise noted, detection of bursts as described herein involves rectified signal data. As shown in FIG. 5, the amplitude (or absolute value of the amplitude) appears to experience a sustained increase 62 at least three times (56, 58, and 60) during the 2-second period. Such sustained increase may be indicative of what is referred to as a burst, or signal or data burst. As discussed in more detail below, fluctuations in time periods between suspected bursts, such as 66 or 68, may be used to calculate a baseline. Fluctuations in a baseline region, i.e., noise, may be related to a peak to peak value, a root mean square (RMS) value or other metric. FIG. 5B illustrates a portion of the EMG data 54, namely, the region of data including burst 60 and adjacent period. In FIG. 5B, a RMS noise value 72 and amplitude 70 are indicated. The signal-to-noise ratio (SNR or S/N) of burst 60 is, in this example, about 4:1, i.e., amplitude 70 is about four times larger than the noise value 72. The EMG data of FIG. 5 is discussed in further detail with regards to a burst detection sub-method in FIG. 7.

Referring now to the exemplary data of FIG. 6 the vertical scale represents the magnitude of a given frequency (which may be referred to as spectral density) and the horizontal scale is signal frequency. Note that the spectral data in FIG. 6 indicates a curving slope with decreasing magnitude as the frequency increases, i.e., the spectral density generally decreases as the frequency increases. The ratio of spectral density at a lower frequency to the spectral density at a higher frequency may be a seizure variable that, for any given portion of electrode data, may have an associated value. For example, for the data shown in FIG. 6 the ratio of spectral density at a frequency of about 200 Hz (76) to the spectral density at about 400 Hz (78) may have a value of about 1.1.

Also, as illustrated in the expanded portion of the same data in FIG. 6B, which shows at least a portion of the characteristic GTC waveform, a region of elevated spectral density 80, i.e., a relatively high-frequency "bump" between approximately 300-500 Hz, and particularly around 400 Hz 82 is shown. That is, the spectral density 80 at frequency 82 in that region is elevated above the spectral density 84, e.g., within a "slumped" region, approximately located at a frequency 86 of about 300 Hz. The term "slump region" or "slump" may in some embodiments refer to a portion of spectral data generally possessing the property of having positive curvature, i.e., a slump region refers to a local minimum in a set of data. The term "bump region" or "bump" may in some embodiments refer to a portion of spectral data where the data generally possesses the property of having negative curvature, i.e., a bump region refers to a local maximum in a set of data. To generally possess a positive or negative curvature means that local fluctuations in individual data points may be averaged or smoothed out of the data. That is, neglecting local fluctuations, e.g., due to noise, a data set may possess a property of curvature.

The ratio of spectral density at a frequency 86 to the spectral density at a frequency 82, or slump to bump ratio, may be used as a seizure variable. In some embodiments, the slump to bump ratio may be used as a metric for detection of a GTC waveform. However, more advanced data analysis techniques, e.g., looking at a greater number of data points and/or advanced pattern recognition algorithms, may also be used to identify a GTC waveform. In some embodiments, a detection unit may include instructions for calculation of a slump to bump ratio and a base unit may calculate a slump to ratio and also corroborate the slump to bump calculation with more advanced pattern recognition analyses. The EMG data of FIG. 6 and the above data features are discussed in further detail with regards to a GTC waveform detection sub-method as described, for example, in FIGS. 11 and 12.

Referring back to FIG. 4, the collection of EMG data may be accomplished with a detection unit and that detection unit may execute an initial analysis and processing of data. In some embodiments, if the detection unit determines that a seizure is likely occurring, it may send data to a base station, where further processing may occur. Thus, a detection unit, a base station or both may process EMG signals, and either or both devices may execute a seizure detection sub-method. Such a sub-method may characterize particular features of EMG data, and may, based upon such a characterization, direct the transfer of data between data registers and accumulation registers. Those aspects of sub-methods, such as described herein in reference to FIGS. 7 and 10-13, may involve aspects of steps 38, 40, 42, 44, and 46 of method 36. A sub-method may feed data into a supervisory algorithm.

Figure 9A:
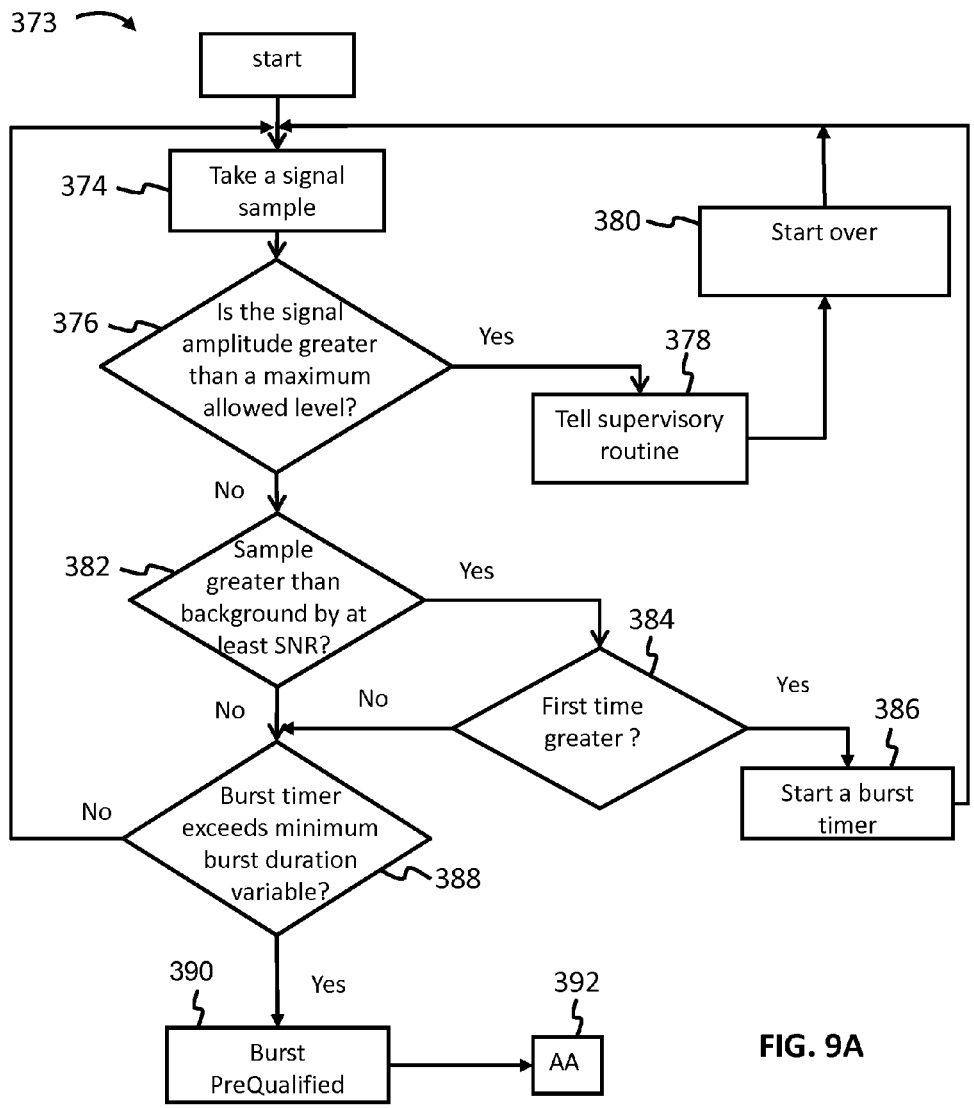
FIGS. 9A, 9B and 9C illustrate another embodiment of a burst and burst train detection algorithm
Figure 9B:
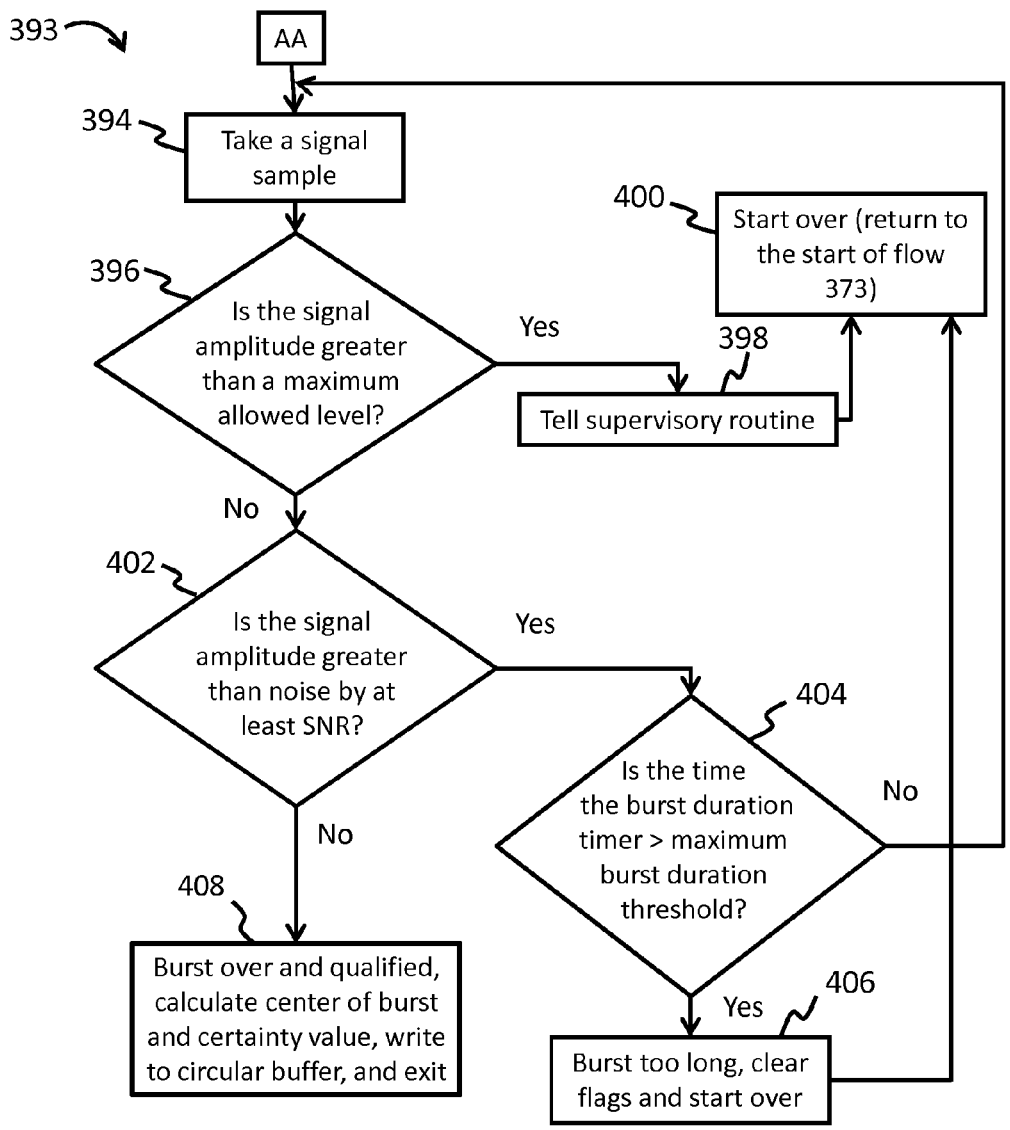
Figure 9C:
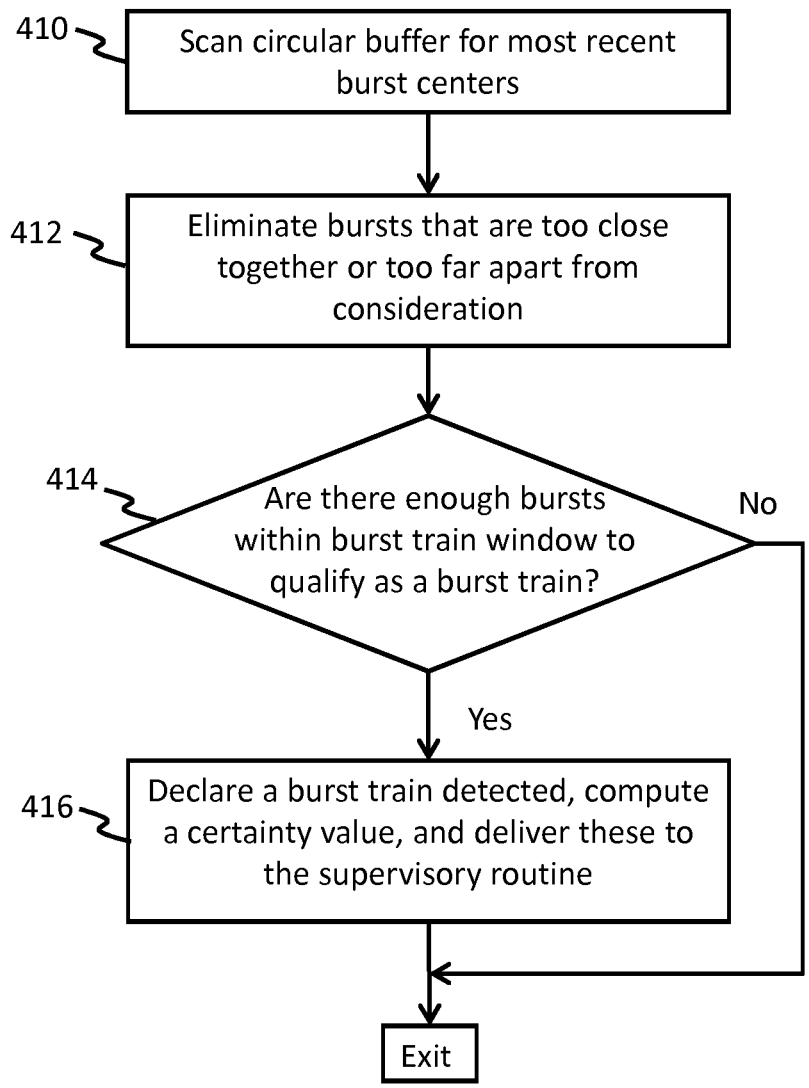

FIG. 7 illustrates one embodiment of a sub-method 88 which may be used for analysis of data bursts. In a step 90 of FIG. 7, a detection unit and/or base station may select a protocol for analysis of data bursts. The selection of an analysis protocol may, for example, be indicated in a template file. Such a template file may include instructions to choose a routine to smooth data, a routine to filter data, a routine to treat the data in some other manner or combinations of routines thereof. Such routines may be executed by either the detection unit, base station or both. The analysis protocol may include a peak detection program, which, for example, after band-pass filtering and rectification may identify and shape a data burst, as shown in the examples of FIGS. 9A, 9B, 9C (collectively referred to as FIG. 9) and FIG. 10. Any suitable peak detection technique may be used (e.g., continuous wavelet transform), and may in some embodiments include, for example, data smoothing techniques (e.g., moving average filter, Savitzky-Golay filter, Gaussian filter, Kaiser Window, various wavelet transforms, and the like), baseline correction processes (e.g., monotone minimum, linear interpolation, Loess normalization, moving average of minima, and the like) and peak-finding criteria (SNR, detection/intensity threshold, slopes of peaks, local maximum, shape ratio, ridge lines, model-based criterion, peak width, and the like).

A peak detector may have separate attack and decay rates. These rates may be individually adjusted. Since there frequently may be plenty of sustained amplitude during a real burst, fear of the peak detected signal decaying too quickly during bursts is generally not a problem. Therefore, the decay rate may be set to decay rather quickly following a burst. Usually the time between bursts is longer than the burst itself, and so there may be no reason to speed up the decay. However, a noise spike between bursts could artificially cause the peak detector output to jump up to a level that would make distinguishing real seizure bursts a problem. Therefore, the attack rate may be carefully controlled to prevent this from occurring.

In step 91 of the method of FIG. 7, a burst detection algorithm may be initiated. Burst analysis may be triggered, for example, by detection of an EMG signal having an amplitude value that meets or exceeds a burst analysis amplitude threshold. Within the burst detection window, the EMG data may be analyzed for elevated amplitude using, e.g., a peak detection program. Regions of elevated amplitude may be classified as potential bursts. For example, referring back to FIG. 5, at least three periods of sustained elevation of amplitude (56, 58, and 60) may be identified in the approximately 2-second epoch. Regions of elevated amplitude within the burst detection window may be measured for amplitude, width, and a SNR may also be determined. A portion of data, e.g., identified as a possible peak, may have amplitude associated with it, e.g., peak amplitude, median, mean or other metric may be calculated.

In step 92 of FIG. 7, EMG signal data, such as within a certain time period (burst detection window), may be analyzed for bursts. For example, for suspected data burst 56, amplitude 62 may be measured. A burst may have an amplitude that is elevated over surrounding portions of data, and that elevated amplitude may extend for a period of time. That is, a burst may have a burst width, such as burst width 64. To determine a burst width, a leading edge of a burst and a trailing edge of a burst may be determined. To detect the leading edge and trailing edge of a burst, changes in amplitude for successive data points may be measured, e.g., the rate of change of amplitude with time may be calculated. Any other suitable technique, such as those described above, may be used, as well. In some embodiments, burst width may be categorized by calculating, for a region of time, whether a threshold minimum amplitude is met at a given probability, e.g., where a majority of points show elevated amplitude above some threshold.

Signal to noise calculations may involve, for example, establishing a baseline by determining fluctuations in detector signal, i.e., baseline noise, in a time period immediately prior to data in a time suspected of containing bursts. For example, an EMG signal may be relatively quiet in the time leading up to a seizure, as discussed in more detail in connection with FIG. 25, below. That quiet period may be used to establish a baseline.

A baseline may also be established by looking at fluctuations between burst periods within the same time window suspected of having bursts. For example, referring back to the EMG data of FIG. 5, data fluctuations in time periods between suspected bursts, such as the data in the time periods 66 or 68, may be used to calculate a baseline. Fluctuations in a baseline region, i.e., noise, may be related to a peak to peak value, a RMS value or other suitable baseline detection metric. In FIG. 5 an expanded region of data, i.e., the region of data including burst 60 and adjacent period, is shown in FIG. 5B, and a root mean square noise value 72 and amplitude 70 are approximately indicated. The S/N of burst 60 may, for example, be about four, i.e., amplitude 70 is about four fold larger than the noise value 72.

It should be noted that the baseline established by looking at fluctuations between burst periods may be different than the baseline established by looking at a pre-seizure quiet time. Thus, different peak detection algorithms may be run for each, or the same algorithm may be ramped up or down with respect to baseline detection depending on whether detecting quiet time or seizure activity. For example, a baseline detector may be a peak detector having a much longer time constant than a peak detector used for signal envelope generation. This baseline detector may rise up to a higher level during a tonic phase but may ramp down during a clonic phase of activity. A negative peak detector may also be employed to ramp a baseline detector down more quickly during relatively quiet times so as to distinguish the bursts more readily.

In step 94, the burst detection algorithm may determine if the EMG signal data within a burst detection window meet various requirements or thresholds or other criteria to qualify regions of elevated amplitude as bursts. For example, the algorithm may determine whether one or more regions of elevated amplitude meet requirements for amplitude, width, and time between regions of elevated amplitude to qualify as seizure bursts. For example, a sub-method for detecting bursts may detect amplitudes above a certain threshold that are closer than Y seconds apart and farther than Z seconds apart. Such requirements (or burst criteria) may be provided in a template file. For example, referring to Table 1, the minimum S/N criteria may be pulled from the template file and compared to the calculated value of S/N for each suspected burst.

Figure 8A:
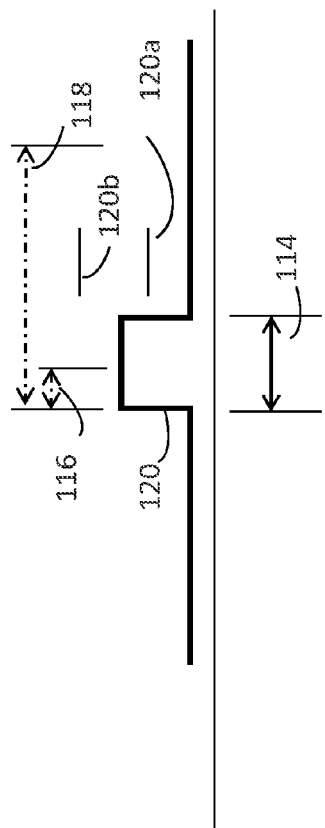
FIG. 8A and FIG. 8B illustrate exemplary model forms or envelopes of signal bursts after filtering, rectification and peak detection.
Figure 8B:
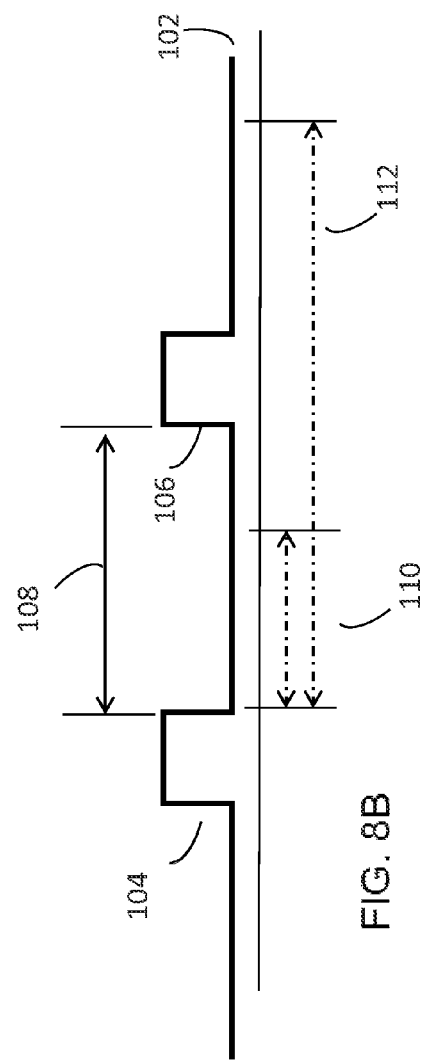

Generally, a burst may be characterized by a sudden increase in the amplitude of the EMG electrode signal from a lower amplitude level, maintenance of that increased amplitude level for a specified minimum amount of time, return of the amplitude level to a lower level of electrode signal after no more than a specified maximum time, and maintenance of the lowered amplitude level for a specified minimum time. FIG. 8A and FIG. 8B (collectively referred to as FIG. 8) illustrate exemplary model forms or envelopes of signal bursts after filtering, rectification and peak detection. Generally, the lower amplitude signal level may not go to zero. The lower amplitude above zero is signal noise. The ratio of the burst amplitude level to the noise level is the SNR. For example, if the signal level of the burst is 1 volt, and the noise is 0.35 volts, then the SNR would be 1/0.35, or 2.86. In the example of FIG. 8, the peak amplitude 120 of EMG signal data may be compared to criterion associated with peak amplitude. If the amplitude 120 is greater than a minimum amplitude criterion 120a, and less than a maximum amplitude criterion 120b, then the ratio of peak amplitude to the level of noise 102 may be determined and compared to a burst amplitude criterion, e.g., a SNR threshold. If the peak amplitude meets the SNR threshold, then the EMG signal data may qualify as a burst (or the start of a burst) with respect to amplitude. A maximum burst amplitude requirement may be helpful in eliminating from consideration elevated amplitude EMG data caused from external noise sources that may introduce amplitude well above the amplitudes capable of being produced by the human body.

FIG. 8A also shows the region of elevated amplitude as having a width 114. The width 114 may be compared to a minimum burst width (dashed line 116) and a maximum burst width (dashed line 118). As may be seen in FIG. 8B, the width 114 falls between the minimum and maximum burst width thresholds, and thus qualifies the region of elevated amplitude as a burst with respect to width. A maximum burst width requirement may be helpful in eliminating from consideration elevated amplitude EMG data that is from voluntary muscle activity, a noise source or is caused by electrode connectivity problems. That could help eliminate falsely identifying real or apparent high-amplitude muscle activity as a seizure.

FIG. 8B shows examples of two successive bursts (104 and 106) separated by a time period 108. In FIG. 8B the time between bursts 108 may, for example be compared to criterion values associated with a minimum period between successive bursts (dashed line 110) and a maximum period between successive bursts (dashed line 112). If a sufficient quantity of bursts succeed each other within the minimum and maximum time periods, then successive bursts may qualify as a burst train indicative of a seizure. However, not all burst trains indicate a seizure, and a periodicity algorithm (discussed in more detail below) may be used to further evaluate the likelihood that a seizure is occurring. For example, extremely regular bursts may not indicate a seizure. Sporadic bursts may not indicate a seizure, either, or if spaced sufficiently far apart, represent minimal threat of imminent harm from seizure.

After reaching the end of the burst detection window, the burst detection algorithm may wait for a delay period before analyzing data in a subsequent burst detection window. By adding a delay, the burst detection algorithm may ensure that new data is analyzed. If analysis of a burst window, or analysis of one or more successive burst detection windows reveals no bursts or near-bursts, then the burst detection sub-method may pause, as seen at step 95, until the burst analysis amplitude threshold triggers activation of the sub-method.

The burst amplitude, width and periodicity values may be stored in registers for use by a supervisory algorithm to determine the likelihood of a seizure occurring. If the supervisory algorithm determines that a seizure is occurring, then it may declare an alarm, and cause the base station 14 to send an alert to a caregiver.

Criterion values may, for example, be included in a template file. More specifically, Table 1 lists exemplary criteria that that may be included in a template file which may be used in a sub-method for evaluation of data bursts. Each criterion may be a variable that may be changed to adjust the sensitivity of the seizure detection method. Of course, not all of the criteria need be used. For example, maximum burst amplitude may be considered optional if unduly limiting for a particular patient. Likewise, additional criteria may be used. For example, if signal amplitude is sufficiently high to trigger the burst detection sub-method, but does not quite meet the minimum burst amplitude even though it meets burst width criteria, then its variance from the minimum burst amplitude may be negatively weighted by a certainty value criterion. A certainty value criterion may be, for example, a percentage value. If the measured amplitude is 95% of the minimum burst amplitude, then the certainty value may be set accordingly. If successive bursts have sufficient periodicity to qualify as a burst train, the negatively-weighted burst may be included in the train to further test periodicity. If a certain number of negatively-weighted bursts appear in the data, then a supervisory algorithm may lower the minimum burst amplitude thresholds to increase the sensitivity of the burst detection method for the particular patient being monitored. Similar weighting may be done with respect to signal values that do not quite meet the other burst criteria. Certainty values may be used by the burst detection method, other sub-methods described herein, and the supervisory algorithm.

TABLE 1

| Template data for a burst detection sub-method | | |
|---|---|---|
| Variable | Value/unit | Type |
| Burst analysis minimum amplitude threshold | XX amplitude | Criterion for initiation of burst detection algorithm |
| Burst detection window | XX seconds | Routine selection |
| Delay between adjacent burst detection windows | XX seconds | Routine selection |
| Minimum burst width | XX seconds | Criterion for burst count |
| Maximum burst width | XX seconds | Criterion for burst count |
| Burst envelope peak detector attack rate | XX | Routine selection |
| Burst envelope peak detector decay rate | XX | Routine selection |
| Minimum burst amplitude | XX amplitude | Criterion for burst count |
| Maximum burst amplitude | XX amplitude | Criterion for burst count |
| Minimum S/N | XX | Criterion for burst count |
| Minimum period between successive bursts | XX seconds | Criterion for burst count |
| Maximum period between successive bursts | XX seconds | Criterion for burst count |
| Decay rate | XX | Data feature/weighting coefficient |
| Decay rate (S/N) modifier | XX | Data feature/weighting coefficient |
| Selection of filter protocol (if applied) | XX | Routine selection |
| Selection of smoothing protocol (if applied) | XX | Routine selection |
| Calculation method | XX | Routine selection |

TABLE 1-continued

Template data for a burst detection sub-method

| Variable | Value/unit | Type |
|---|---|---|
| Baseline calculation method | XX | Routine selection |
| Coefficient (combination with supervisory algorithm) | XX | Weighting coefficient |

For clarity, the "XX" is simply a value placeholder, and should not be construed to connote magnitude or precision in any way.

Referring back to FIG. 7, in a step 96, one or more detection registers may be loaded with burst values for a detection window. For example, a burst count register may be used to contain a value corresponding to the number of detected bursts within the burst detection window. For example, if the two-second time period of FIG. 5 was a burst detection window, then the EMG data within that window may be analyzed for bursts. In FIG. 5, for example, the EMG signal data shows three bursts. Thus, a value of 3 may be stored in the burst count register. Other registers may be used to store other burst values, such as amplitude, periodicity, width, certainty values, and so forth.

Following each burst detection cycle, e.g., analysis of a burst detection window, the detection register may, in some embodiments, add its contents to one or more burst accumulation registers (step 97). Before analyzing the data in subsequent burst detection windows, the detection registers may be cleared to allow storage of burst data for the subsequent burst detection windows. The detection registers may then begin storing burst values during another cycle, or, in some embodiments, begin counting bursts after a certain delay period.

In some embodiments, the EMG signal data may be written to a circular buffer in RAM in the device hardware. One advantage of such a strategy may be that less RAM is used because the processed data may store only a pattern of the data, such as peak detected values, and not a point by point data file of full signal data. That is, a voltage (or other electrical parameter that reflects amplitude of the detection unit) at each corresponding point in time need not be stored. For example, in some embodiments, only the data necessary to derive a model form such as indicated in FIG. 8A and FIG. 8B may be stored. It should be appreciated in those figures that noise in regions between detected bursts is depicted to be maintained at a constant level. Thus, only a calculated value of the noise, e.g., such as RMS amplitude (102), may be stored and not all of the individual fluctuations in the baseline data. Thus, the data file in RAM may be significantly compressed. In some embodiments, as opposed to storing a compression of the data in a time window, all raw data from a given window may be stored in a circular buffer in RAM. It should thus be appreciated that an algorithm may look at any given preceding time window at any point in the algorithm. Such may be used, for example, to consider how any given value of EMG data has changed between one or more time windows.

In some embodiments, each burst may be weighted with a value that is not only related to detection of a burst but also related to the certainty of burst detection. Certainty values may, for example, be related to the normalized amplitude or the ratio of the normalized amplitude to detector noise. For example, a signal burst may be characterized by transition from approximately 100% of the normalized amplitude to approximately 35% of the normalized amplitude. The certainty value may be approximately 65, which number may be loaded into a register whose maximum value could be approximately 100.

As denoted in step 97, one or more of the detection registers may add their contents to one or more accumulation registers. For example, a burst count detection register may add its value to a burst count accumulation register.

In step 98, the accumulation registers may, in addition to accepting a data value from the detection register, adjust the value of any previous data which may be held. For example, in some embodiments, the burst count accumulation register may hold a value that is related to the quantity of bursts collected in a preceding number of burst detection cycles. That is, each time the burst count detection register adds contents from one cycle, the burst count accumulation register may remove a data value that was added during some preceding cycle. Thus, the burst count accumulation register may, in some embodiments, act as a moving sum based on the sum of counts from a number of preceding burst detection windows. In such an embodiment, the computer may store in memory, e.g., in any number of additional registers, the appropriate data value to add or subtract from the burst count accumulation register. In other embodiments, at the completion of a cycle, the burst count detection register may add any contents, e.g., value of collected bursts, to the burst count accumulation register and then remove a certain value, i.e., it may leak at a certain rate. A leakage rate, or decay rate as shown in Table 1, may be included in a template file and may be adjusted to customize the burst detection sub-method to a particular patient or patient demographic. In some embodiments, the leakage rate may be a value that is modified based upon another criterion. For example, the burst count accumulation register may be modified if one or more successive burst detection windows do not contain any bursts.

In other embodiments, the rate of decay of the burst count accumulation register may depend upon the S/N of bursts counted in one or more given time window. In further embodiments, the burst count accumulation register may be modified based on how the S/N of bursts is changing. That is, the average S/N of detected bursts may be tracked, e.g., the average S/N value of bursts in given time windows may, at least for some period of time, be stored in memory, such as in a circular RAM buffer. If the S/N of bursts changes between time windows, such a change may be analyzed, and used to modify the decay rate of the burst count accumulation register. In general, if the S/N of bursts is increasing the decay rate of the burst count accumulation register will drop by some factor and if the S/N of bursts is decreasing the decay rate of the burst count accumulation register will increase by some factor. In addition, during step 98 the contents of the burst count accumulation register, may decay in a manner that is dependent upon various negative weighting factors. For example, if no bursts are detected in a cycle, such may be an indication that a seizure is not occurring, and the rate of decay of the burst count accumulation register may be adjusted. Again, to analyze data in preceding time windows, either point by point data or a model shape may be stored in a circular buffer of RAM in the system hardware. Referring back to FIG. 4, the value stored in the burst count accumulation register is an example of one value that may be examined with a supervisory algorithm.

In step 99, the burst detection algorithm may wait for a time period equal to the burst detection window delay value before analyzing EMG signal data in subsequent burst detection windows. The burst detection registers may be cleared in step 100 before analyzing EMG data in the next burst detection window. In some embodiments, the burst detection algorithm may continue to run until it finds one or more burst detection windows that do not contain any bursts or near-bursts, or until the supervisory algorithm triggers an alarm.

In general, the presence of qualified bursts, and a large value being stored in the burst count accumulation register, may increase the probability that a seizure event is declared. It is also an aspect of methods described herein, negative weighting factors may be used, for example, with respect to signal characteristics that diminish the likelihood that a seizure is occurring. For example, as discussed above, different negative weighting factors, such as the absence of bursts in a preceding time window, or a decreasing S/N may influence the leakage rate of an accumulation register.

FIGS. 9A, 9B and 9C illustrate another embodiment of a burst and burst train detection algorithm. The flowcharts of FIGS. 9A-9C show logic flow, not actual routines. In an actual routine, they would be called by the supervisory algorithm or be scheduled as one-time passes by timer interrupt, not infinite loops. There are two main routines, the burst detection algorithm (FIGS. 9A and 9B), and the burst train detection algorithm (FIG. 9C). The burst detection algorithm looks for a burst that meets the requirements of amplitude (both min and max) and minimum width. If the minimum spacing between detected bursts is too small, the burst train detection algorithm will catch it. A burst train detection algorithm may rely on a periodicity algorithm, as discussed below.

FIG. 9A illustrates one embodiment of a burst detection logic flow 373. Burst detection logic flow 373 may include obtaining a signal sample in the step 374. In the step 376, the logic flow may include determining if the signal amplitude is greater than a maximum allowed amplitude level. If the signal amplitude is greater than the maximum allowed level, then the supervisory algorithm may be informed in the step 378, and the burst detection logic flow may then start over (step 380). If in the step 376 the signal amplitude is not greater than a maximum level, then the flow 373 may, in the step 382, determine if the signal amplitude is greater than noise by at least some SNR. If the signal amplitude is greater than the SNR, then the burst detection logic flow 373, as shown in step 384, may include determining if it was the first time in the routine that the required SNR level was met. If it was the first time the SNR level was met, then the routine may start a burst timer (step 386) and take another signal sample (step 374). If it was not the first time that the SNR level was met within the flow, then the flow may include determining, in the step 388, if the burst timer has exceeded a minimum burst duration threshold. If the burst timer has exceeded the minimum burst duration threshold, then the signal may, in the step 390, be pre-qualified as a burst. The pre-qualified burst may then be processed in the exemplary flow 393 shown in FIG. 9B as shown in the (step 392).

The burst detection logic flow 393 in FIG. 9B may include taking a signal sample (step 394). The signal sample may, for example, be a signal sample pre-qualified as a burst as described in FIG. 9A. In the step 396, the routine may determine if the signal amplitude is greater than a maximum allowed amplitude level. If the signal amplitude is greater than the maximum level, the supervisory algorithm may be informed in the step 398, and the burst detection flows 373, 393 may start over (step 400). That is, a new signal sample may be taken in the step 374 of FIG. 9A. If the signal amplitude is not greater than the maximum allowed amplitude level, the routine may then include determining, in the step 402, if the signal amplitude is greater than background by at least a SNR. If the signal amplitude is greater than noise by at least the SNR, the routine may, in the step 404, determine if the burst duration timer has exceeded a maximum burst duration threshold. Considering the flows 373 and 393 together, the duration of activation of the burst timer, which may be initiated in the step 386 of the flow 373, may be evaluated against each of a minimum burst duration threshold 388 and maximum burst duration threshold 404. That is, viewing the flows 373 and 393 together data may be compared against each of a minimum duration threshold and a maximum duration threshold. If the maximum burst duration threshold is exceeded in the step 404, as shown in the step 406, it may be deemed that the burst is too long, and the process may start over (as shown in step 400). If the maximum burst duration threshold is not exceeded in the step 404, a next signal sample may be taken in the step 394. And, as long as the signal amplitude does not exceed the maximum allowed level in step 396, the flow 393 may loop back to the step 402 and evaluate if the signal amplitude is greater than noise by at least a SNR. If in the step 402, it is determined that the taken signal sample (which may include signal sample in any number of loops of the flow 393) does not exceed background by the SNR level, a burst may be deemed to be over and the burst may be qualified (step 408). As indicated in the step 408, a signal qualified as a burst may be characterized by a certainty value, the center of the burst may be determined and the burst data may be written into a circular memory buffer for further analysis.

In the burst train detection logic flow of FIG. 9C, data in a circular buffer may be analyzed. In the step 410, the routine may scan the circular buffer for the most recent burst centers. In the step 412, the logic flow may eliminate bursts that are too close together or too far apart from consideration. In the step 414, the routine may evaluate whether there are enough bursts within a window to qualify as a burst train. If enough bursts are detected, the routine may, in the step 416, qualify the scanned data in the circular buffer as a burst train, calculate a certainty value, and deliver the burst data to a supervisory routine for further analysis. In the step 414, if there are not enough bursts within the burst train window the flow may exit.

Figure 10:
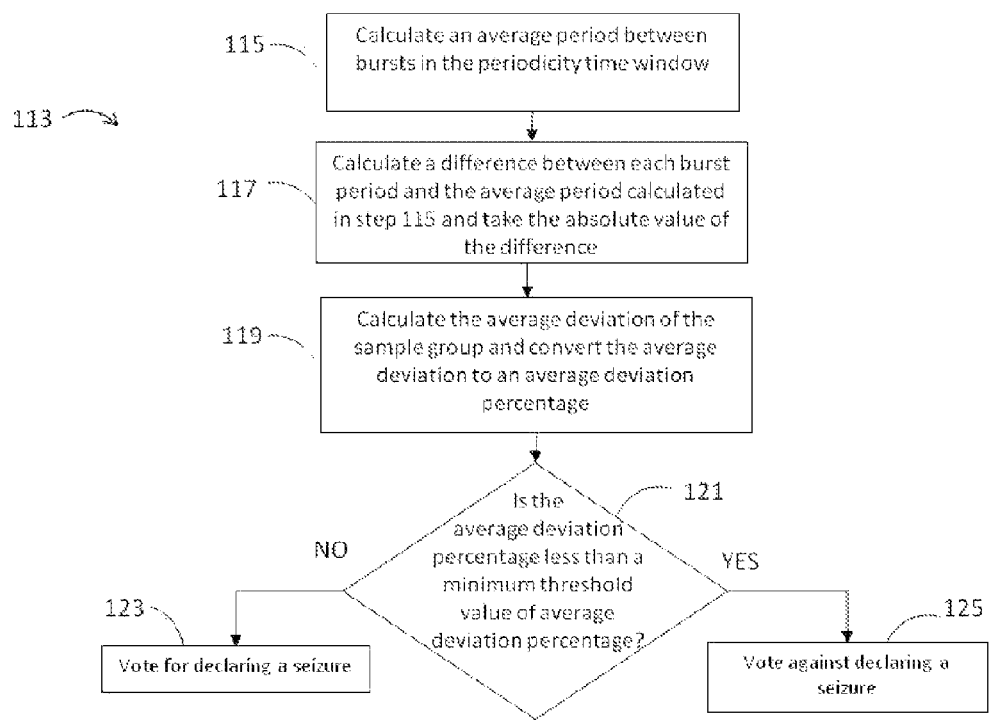
FIG. 10 illustrates one embodiment of a periodicity algorithm.

In FIG. 10 an additional exemplary algorithm 113 (the periodicity algorithm) is described that may, in some cases, act to suppress the initiation of a seizure alarm. The periodicity algorithm accomplishes this task by looking at the circular buffer over a time frame and examining the regularity of time periods between the detected bursts. A periodicity algorithm may scan different data values from various time windows that the burst detection algorithm wrote into a circular buffer, and examine the periodicity of signal characteristics, including those that may not be indicative of a seizure.

In some embodiments, variables in the periodicity algorithm may be:
  Periodicity Time Window (in seconds)
  Minimum Average (or Standard) Deviation Allowed (percentage)

The periodicity time window variable is the period of time over which the periodicity algorithm scans data. For example, the periodicity time window may be sufficient to include some number of burst detection windows from the burst detection algorithm. The Deviation Allowed variable is the minimum value of how far from a single frequency the bursts may be distributed to qualify as a seizure. If the bursts huddle too closely around a specific frequency, for example 1 Hz, then that burst train may not indicate a real seizure. In some embodiments, values for the periodicity algorithm may be empirically selected for default. This variable could be altered based upon patient history, experience, patient modeling and learning, and/or human feedback. In some embodiments, a patient may, for example, partake in different activities, such as, for example brushing teeth, exercising, walking or other activities to collect data that may be used to establish defaults for the periodicity algorithm.

In step 115 of the exemplary method of FIG. 10, the average duration of the period between bursts within the periodicity time window may be calculated. In step 117, each actual duration of the value of each such time period may be subtracted from the average time value, and the absolute values of the differences used to calculate, in step 119, the average deviation of the periods, and convert the average deviation to a percentage.

In step 121 the average deviation percentage may be compared to threshold values such as a minimum threshold value of average deviation percentage as indicated in FIG. 10. Such threshold values may be taught to the system in operation and may be customized for the particular environment that an individual may commonly occupy.

For example, if in a periodicity time window (measuring in seconds), nine bursts were detected at the following times:
12, 13, 13.75, 14.35, 15, 15.8, 16.2, 16.5, 17.4
there would be 8 time periods between bursts. So, over a periodicity time window including the foregoing epoch of 5.4 seconds, there were nine bursts with eight periods between bursts. The average period may be calculated as 5.4/8=0.675 seconds per burst. The time periods between bursts are as follows:
13−12=1
13.75−13=0.75
14.35−13.75=0.6
15−14.35=0.65
15.8−15=0.8
16.2−15.8=0.4
16.5−16.2=0.3
17.4−16.5=0.9
In this example, a simplified method allows the time around which a burst is centered to serve as a time stamp for that burst. In other words, each time the burst algorithm qualifies a burst, a time stamp may be written into a circular buffer for use by the periodicity algorithm. In other embodiments, real burst width may be used to calculate the actual length of the time periods between bursts. For example, if the burst occurring at 12 seconds lasted for 0.02 seconds, then the time period between the burst starting at 12 and the burst starting at 13 would be 0.98 seconds. The absolute value of the deviations from the average may be calculated as follows:
1−0.675=0.325
0.75−0.675=0.075
0.675−0.6=0.075
0.675−0.65=0.025
0.8−0.675=0.125
0.675−0.4=0.275
0.675−0.3=0.375
0.9−0.675=0.225
Averaging the absolute values may be accomplished as follows:
Sum of all deviations: 0.325+0.075+0.075+0.025+0.125+0.275+0.375+0.225=1.5
Average deviation: 1.5/8=0.1875
The average deviation percentage is: 0 0.1875/0.675=27.8%. That is a significant deviation from the average and is unlikely to be artificial. If a minimum threshold value of the average deviation percentage is set, for example, to 15%, then the periodicity algorithm would declare that confidence is high that this is a seizure and would not vote against declaring that a seizure alarm (step 123). The result may be placed in a register for use by the supervisory algorithm.

In another simplified example, the burst train could look like this (in seconds):
17, 17.5, 18.02, 18.51, 19.04, 19.56, 20.1, 20.6, 21.13
So, over a periodicity time window including the foregoing epoch of 4.13 seconds, there were nine bursts with eight periods between bursts. The average period may be calculated as 4.13/8=0.51625 seconds per burst. The individual times between bursts are as follows:
17.5−17=0.5
18.02−17.5=0.52
18.51−18.02=0.49
19.04−18.51=0.53
19.56−19.04=0.52
20.1−19.56=0.45
20.6−20.1=0.5
21.13−20.6=0.53
The absolute value of the deviations from the average are as follows:
0.51625−0.5=0.01625
0.52−0.51625=0.00375
0.51625−0.49=0.02625
0.53−0.51625=0.01375
0.52−0.51625=0.00375
0.51625−0.45=0.06625
0.51625−0.5=0.01625
0.53−0.51625=0.01375
The sum of all deviations may be calculated as follows:
0.01625+0.00375+0.02625+0.01375+0.00375+0.06625+0.01625+0.01375=1.6
The average deviation is therefore: 1.6/8=0.02
The average deviation percentage in this example is thus: 0 0.02/0.51625=3.87%. This example thus shows a very regular pattern. If the minimum threshold value of average deviation percentage was set to 15%, then the algorithm would declare that confidence is very low that a true seizure is occurring and would vote against declaring a seizure alarm. The result may be placed in a register for use by the supervisory algorithm.

Of course, standard deviation calculations may be substituted for average deviation calculations for a more statistically accurate result.

The supervisory algorithm may use the results of the values provided by the periodicity algorithm. That is, in steps 123 or 125 the algorithm may add either a positive or negative value to the supervisory algorithm. Therefore, as indicated in FIG. 10, the periodicity algorithm may either vote for declaring that bursts in the periodicity time window are indicative of a seizure (step 123) or vote for declaring that bursts in the periodicity time window are not indicative of a seizure (step 125). The particular value added may depend upon comparison to thresholds in step 121. The value added to the supervisory algorithm may, in some embodiments, depend not only on the particular decision, at step 121, but also on the certainty in which the decision was qualified. In addition, the value added to the supervisory algorithm may depend on other features measured. For example, characteristic patterns in an environment may not only have a certain periodicity they may also have certain amplitude. For example, an algorithm may learn that a certain period is typically identified with a certain signal amplitude and when those characteristics are viewed together, an additive or super-additive value may modulate the supervisory algorithm.

In a real seizure, the bursts can look like they are spaced evenly. However, these are generated by the body and may be only rarely evenly spaced. Real seizures are generally characterized by some variance in the spacing between bursts. Other sources of signals, that is, sources that are not derived from seizure muscle activity, may be picked up by the EMG electrodes. For example, mechanical vibration of the room or bed could result in a rhythmic vibration of the arm or other muscle to which the electrodes are attached. This could cause signals which may be picked up from the electrodes and may have an elevated amplitude. However, these signals may be very regular in frequency. Likewise, regular voluntary body movements, such as from brushing teeth, may produce bursts that look like a seizure. Whatever the source of interference at the electrodes that may look like bursts, the periodicity algorithm evaluates the periodicity of pseudo-bursts as being too regular and therefore not indicative of a seizure.

Figure 11:
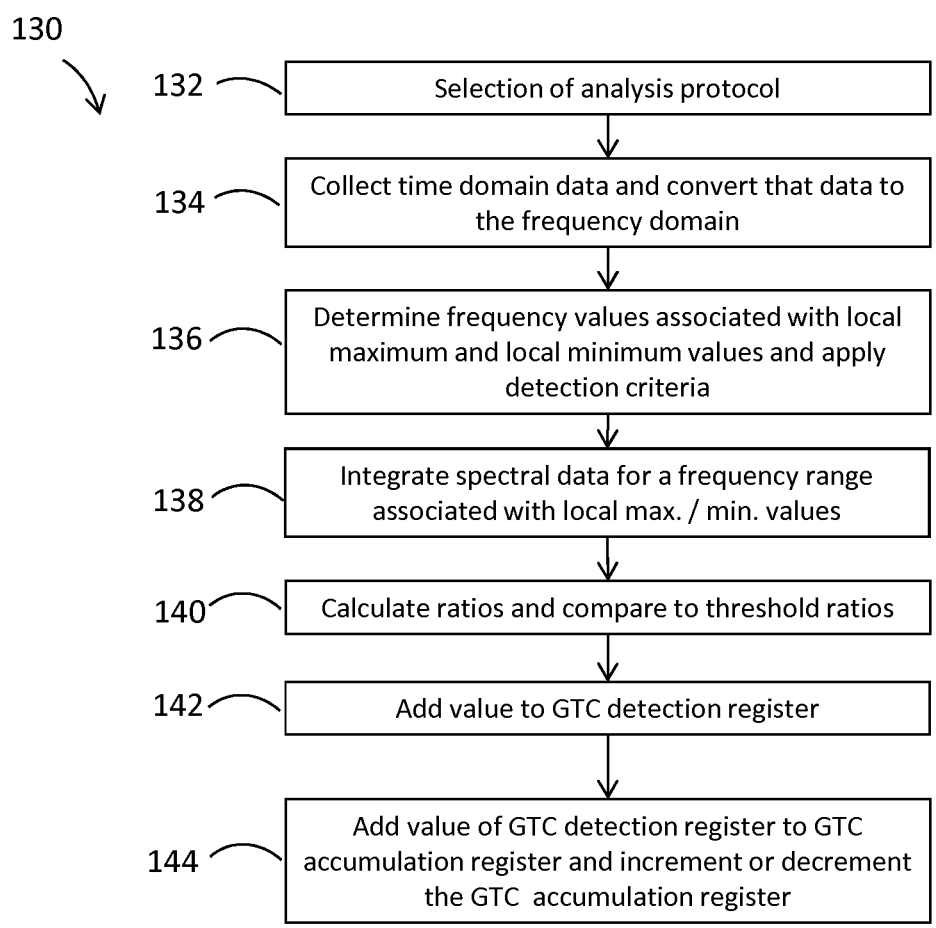
FIG. 11 illustrates one embodiment of a GTC waveform detection algorithm.
Figure 12:
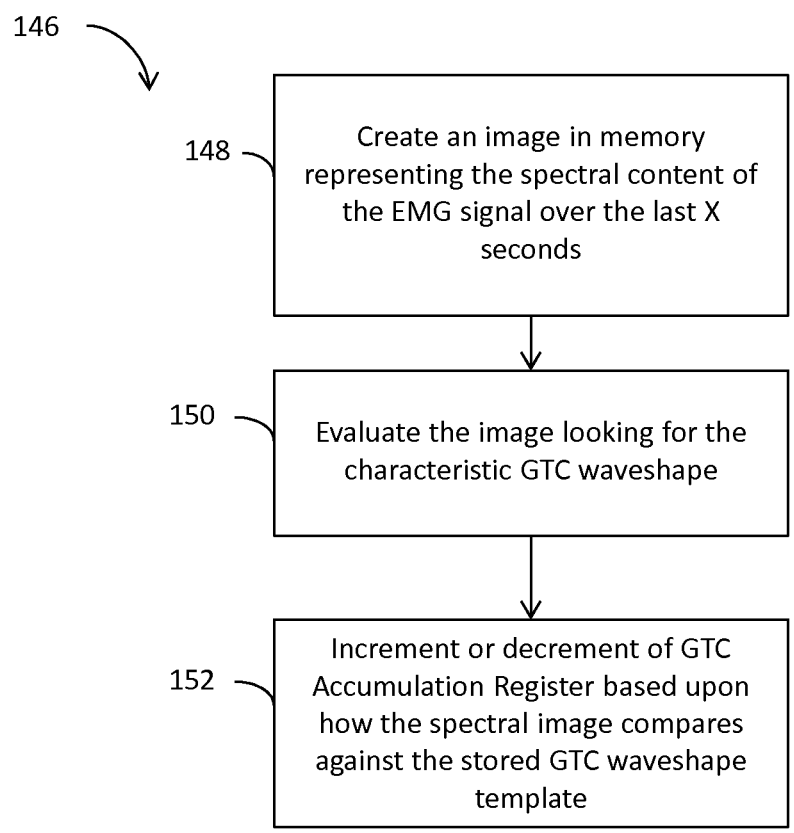
FIG. 12 illustrates a second embodiment of a GTC waveform detection algorithm.

FIG. 11 illustrates one embodiment of another sub-method that may also contribute a value that may be that may be examined with a supervisory register. In FIG. 11, one embodiment of a GTC waveform detection algorithm 130 is illustrated. FIG. 12 illustrates another embodiment of a GTC waveform detection algorithm 146. As previously described, in some embodiments, the detection unit and the base station may analyze data in the same or different ways. The embodiment of FIG. 10 may, for example, be useful as an initial screen of data, i.e., it may be used to determine whether a data set is sent to a base station. The embodiment of FIG. 12 may, for example, involve the comparison of a spectral shape to a large number of files stored in memory and may be executed by a base station.

In a step 132, as shown in FIG. 11, a detection unit and/or base station may select an analysis protocol. The selection of an analysis protocol may, for example, be indicated in a template file. Such a template file may include instructions to choose a routine to smooth data, a routine for data filtration, a routine to treat the data in some other manner, or combinations of routines thereof. Such routines may be executed at various steps in sub-method 130. In a step 134, data may be collected and FFT methods may be used to convert data between the time and frequency domains. In collection of EMG data, suitable sample rates may be used as appropriate, for example, to avoid aliasing of the frequency domain data. In a step 136, the frequency value associated with a local minimum value and a local maximum value of the power density may be determined. To accomplish such, the data may typically be smoothed and a parabolic function fit to the data in a frequency region suspected of being a local maximum. In attempting to find local extreme values, the sub-method may find that the EMG data does not meet criteria to be classified as a GTC waveform. For example, the sub-method may find that in a given region expected to show a local maximum or local minimum value, the data does not exhibit such behavior.

The sub-method may, if local maximum and local minimum values are found, calculate the area under the power density/frequency curve for a region associated with the determined local extreme values (step 138). For example, the program may calculate the area under a region of 10 Hz centered on the determined local maximum and also calculate the area under a region of 10 Hz centered on the determined local minimum. The ratio of these areas may be calculated, i.e., a slump to bump ratio may be calculated, in a step 140, and compared to a threshold ratio, e.g., minimum and maximum threshold for acceptable slump to bump ratios. If the slump to bump ratio is within the threshold bounds a value may be added to a GTC detection register in a step 142. The value added to the GTC detection register, may, in some embodiments, be related to the certainty in which the slump to bump ratio was detected. In a next step 144, the value of the GTC detection register may be added to a GTC accumulation register. That is at the completion of a cycle, i.e., after each GTC collection window, the GTC detection register may add any contents, e.g., a value reflecting a detected slump to bump ratio, to the GTC accumulation register. In some embodiments, the GTC collection window may be the same as the burst detection window, i.e., the GTC waveform detection algorithm may analyze the same data that the burst detection algorithm analyzes. The GTC accumulation register may then be changed by a certain value, e.g., it may leak at a certain rate.

Referring to FIG. 12, in a step 148, another embodiment of the waveform detection algorithm may, for example, create an image in memory representing the spectral content of the EMG signal over a certain period of time. For example, one or more detectors may collect data over a certain time window and then that data may be converted to the frequency domain for spectral analysis. In a step 150, the waveform detection algorithm may evaluate the image, e.g., spectral data, and look for a characteristic GTC waveform. Any number of spectral regions, such as a high frequency region of the spectrum may be analyzed. In a step 152, a GTC accumulation register may be populated in a manner that depends on how the spectral data compares to a stored GTC waveshape template.

FIG. 13 illustrates one embodiment of a waveform regularity detection algorithm 154. Like a periodicity algorithm, a waveform regularity detection algorithm may be used to determine if bursts are too regular in waveform to originate from seizure activity. In a step 156, the amplitude and burst width of EMG signal data during a time period may be determined. This may be accomplished in much the same way as described in for the burst detection algorithm. In a step 158 a waveform may be calculated, e.g., data from a sub-period of time around a burst may be converted to the frequency domain and a waveform calculated. The waveform may be calculated and compared to waveforms that were collected for other bursts in the time period. In some embodiments, if those waveforms are too uniform, e.g., identical or very similar in at least some characteristics, then a regularity accumulation register may be incremented. Differences between waveforms may be calculated in a manner similar to that of a periodicity algorithm, e.g., by determining an average waveform, calculating the average deviation of each waveform, and determining the percentage difference of the average deviation from the average waveform. If that percentage difference falls below a regularity threshold requirement (another variable), then a regularity detection register may be populated. In succeeding detection cycles, the regularity detection register may add its contents to a regularity accumulation register. In some embodiments, the waveform may look for uniformity within a given time period by converting data collected over that time period to the frequency domain and detecting a spike in amplitude over a very narrow frequency range. In a step 150, if the waveform regularity decreases then the regularity accumulation register may decay. As previously noted, some seizure variables may either enhance or weigh against the declaration of an alarm. In some embodiments, the value a regularity accumulation register may serve to suppress the declaration of an alarm. Referring back to FIG. 4, the values stored in either GTC accumulation register of sub-methods 130 or 146, or the value stored in the regularity accumulation register, such as described in sub-method 160, may be a value that may be used by a supervisory algorithm.

The value stored in all or some of the above referenced accumulation detection registers, e.g., such as described in relation to FIGS. 7, 11-13, and 18, or input from other algorithms, e.g., as discussed in FIG. 10, may be periodically evaluated, such as in a step 48 of FIG. 4, which describes the use of a supervisory algorithm. The supervisory algorithm may be the overall seizure detection program running in the processor of a device in the seizure detection system 10, such as the detection unit 12 or base unit 14. Among other things, the supervisory algorithm may determine whether a seizure is in process. The supervisory algorithm may accomplish this by evaluating the conclusions of the other sub-methods or algorithms that analyze EMG signal data, and perhaps other data such as temperature or heart rate, as well. A supervisory algorithm may convolute data in one or more registers that correspond to seizure variables. For example, as discussed above, a sub-method may, e.g., identify a specific characteristic of data, calculate a certainty value, and increment a register value. A supervisory algorithm may then take the register values and multiply each value by a coefficient (e.g., from zero to one) to give more weight to certain seizure variables, and then may add all of the resultant products together. If the sum of the products exceeds a threshold value, then a seizure may be declared as detected, and an alert sent accordingly. For example, an example would be TOTAL=a(register 1)+b (register 2)+ . . . z(register 26). If TOTAL ever goes over the detection threshold, then a seizure detection may be declared.

Figure 14:
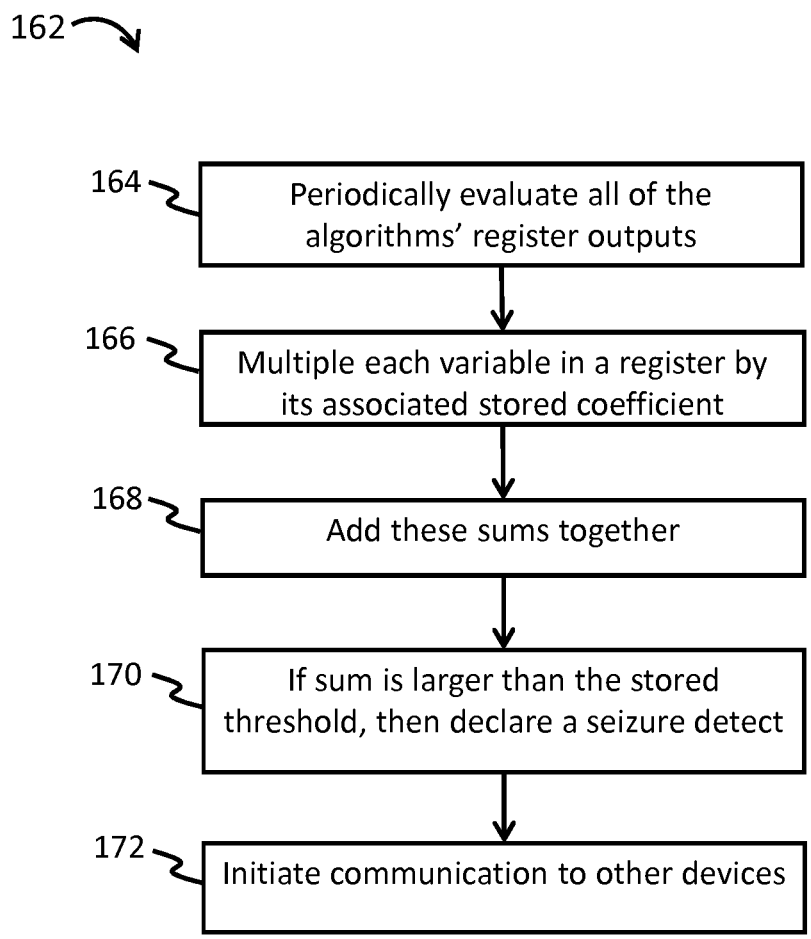
FIG. 14 illustrates one embodiment of a supervisory algorithm.

FIG. 14 illustrates one embodiment of a supervisory algorithm 162. In a step 164, the supervisory algorithm may periodically evaluate one or more of the detection and accumulation registers. That is, the supervisory algorithm may determine the value stored in such registers. In a step 166, the supervisory algorithm may multiply, or convolute in some other manner, the value in each register by an appropriate weighting coefficient. Such weighting coefficients may, for example, be associated with a template file. For example, table 1 indicates a coefficient that may be used to adjust the value of the burst count accumulation register. A sum of the values in accessed detection and accumulation registers may be added together in a step 168. In a step 170, the sum determined in step 168 may be compared to an overall threshold. If the sum is larger than the threshold, then a seizure alarm protocol may be initiated (step 172). In some embodiments, a supervisory algorithm may evaluate the output of a portion of the registers. For example, one or more registers may be evaluated, convoluted with coefficients, compared to a threshold, and if appropriate, an alarm protocol may be initiated. In some embodiments, the coefficient by which one seizure variable is modified may depend upon the value of another seizure variable. For example, the system may learn that when two seizure variables are simultaneously elevated, or related in some other way, that the system may detect a seizure with higher confidence.

Figure 14A:
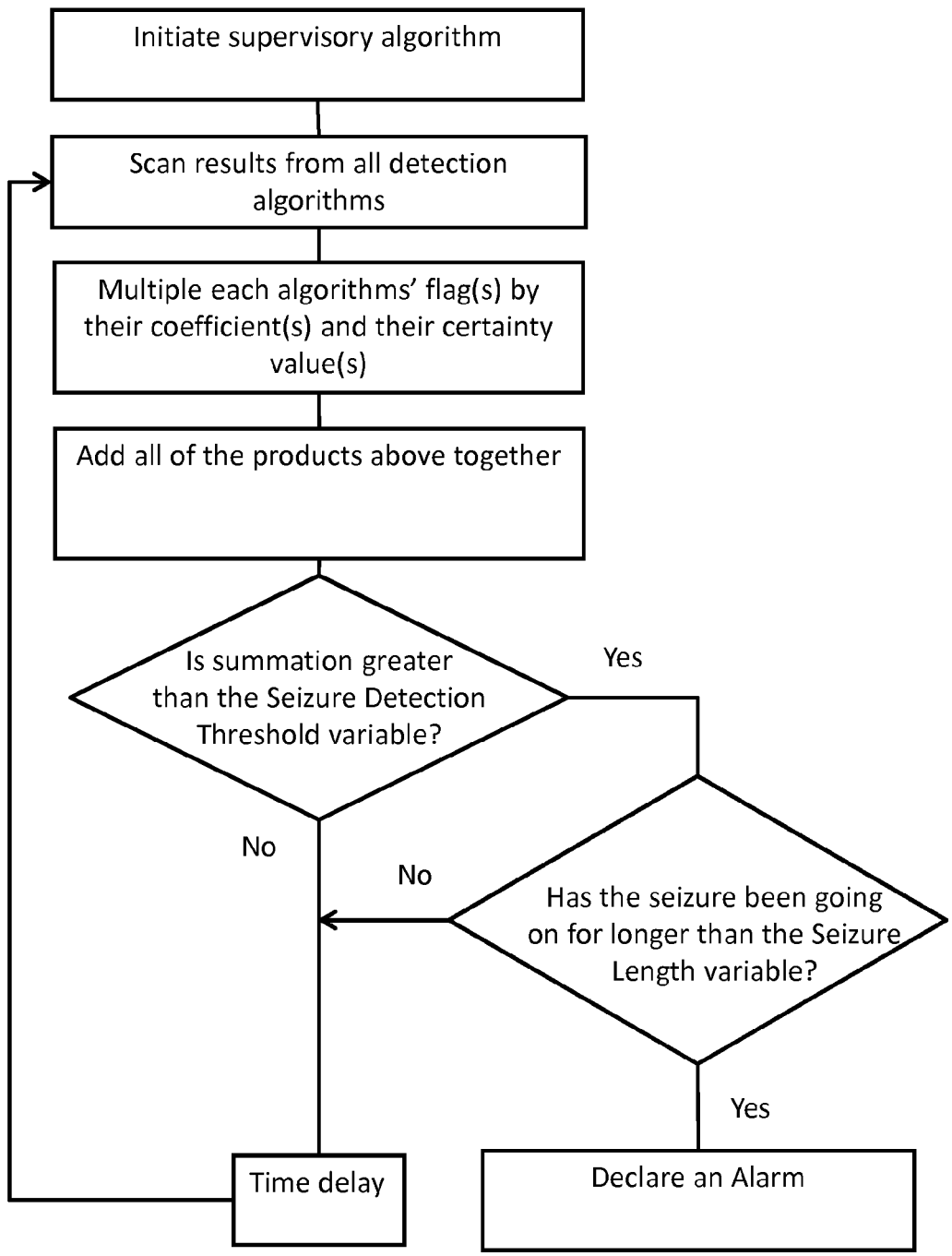
FIG. 14A illustrates another embodiment of a supervisory algorithm.

FIG. 14A illustrates another embodiment of a supervisory algorithm. A supervisory algorithm may analyze the processed EMG data with respect to a different seizure characteristics. A supervisory algorithm may integrate or average over time its results and continually update its conclusions. This may serve to remove short glitches or spikes in the data that could lead to a false positive. In the embodiment of FIG. 14A, the supervisory algorithm uses register values from some of the foregoing sub-algorithms as follows:

Burst Train Detect flag and Certainty value
Periodicity good or bad and Certainty value
GTC waveform Detect and Certainty value In this embodiment, each sub-algorithm could produce a flag indicating a detection, or, in the case of the periodicity, a flag that votes against detection. Each may have a coefficient or multiplier variable (A, B, C, D) that establishes each sub-algorithm's importance or weight in the overall determination of seizure declaration. As discussed above, certainty values may range from 0 to 100%, with 100 being the highest certainty. The supervisory algorithm uses the Certainty Value to gauge confidence in the results of the Burst Detection algorithm.

Generally, a Certainty value may be used by one algorithm to transmit to another algorithm how certain the first algorithm was in its judgment. For a burst detection algorithm, for example, one metric may be the average SNR during the burst normalized to a max value of 50. Another metric may be how closely the burst looks like an ideal burst, e.g., through waveform regularity analysis. A burst that is barely greater in width than the minimum may not rate as high as one 5 times wider than the minimum. Also, a burst that is too close to the maximum may given a lower certainty value. For example, as suggested herein, a reference burst width could originally come from empirical data from many test patients experiencing actual seizures, and be a factory default. Later, as data from the patient is gathered, a more representative ideal width could be established for that patient. The rating of a burst width could be normalized to a max value of 50 and added to the SNR value for a maximum of 100. Other metrics could be factored in as well and each could be weighted differently. One example of a method of weighting would be to normalize each to a different value:

SNR 40%
Width 35%
Amplitude 25%

A similar process for establishing certainty values could be implemented for each sub-algorithm.

An equation that the supervisory algorithm could use to quantify the decision process is:

Seizure_detection=$A$*(Burst_Train_Flag*Certainty)+
    $B$*(Periodicity_good_flag*Certainty_good)−$C$*
    (Peridodicity_bad_flag*Certainty_bad)+$D$
    (GTC_flag*Certainty_value)

If the sum is greater than a Seizure Detection Threshold variable value, then the supervisory algorithm declares a seizure. Other seizure variables may be used, such as Seizure Length could be used to specify how long (time in seconds) the seizure must be in process before an alarm is generated. If the sum is less than a Seizure Detection Threshold variable value, then the supervisory algorithm may be inactive for a period of time before re-scanning sub-method registers.

It can be seen from the above equations that if the periodicity is good, it adds to the summation with one weight. If the periodicity is bad, it subtracts from the summation with another weight. This allows the periodicity algorithm to strongly vote against a seizure detection if it determines that the EMG signals include obvious interference such as harmonics from the power mains, fluorescent lights, etc. Other inputs such as temperature or heart rate could be added with their own coefficients and certainty values. Sometimes heart rate can be detected with EMG electrodes and thus would require no more electrodes. However, dedicated electrodes for heart rate and temperature may provide better signals with respect to those phenomena.

An aspect of systems and methods described herein is that they may be readily customized and adapted as more data regarding general seizure characteristics for a patient, or patient demographic, is collected. Such methods may use algorithms that may have a set of routines, coefficients, or other values that may be included in a modifiable template file. It may, in some embodiments, also be useful that a detection system, e.g., a system that is designed to quickly detect seizures, has an accurate log of the data and also a log of the condition of a patient. That is, for example, a detection system that has accurately logged the event it is intended to detect and the detection data itself (and correlated those events in time), may, as described below, be optimized.

Figure 15:
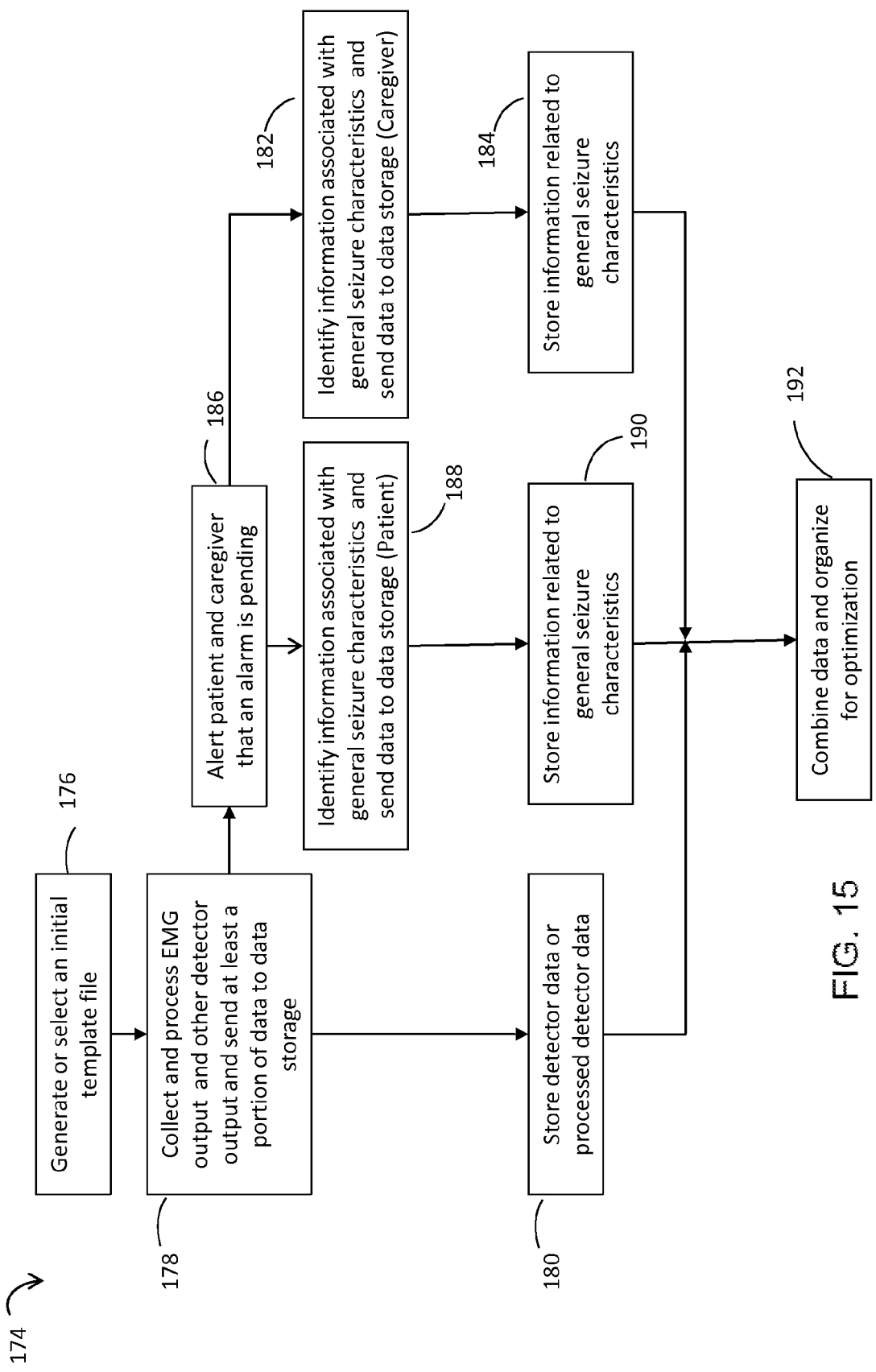
FIG. 15 illustrates one embodiment of a method of data collection.
Figure 16:
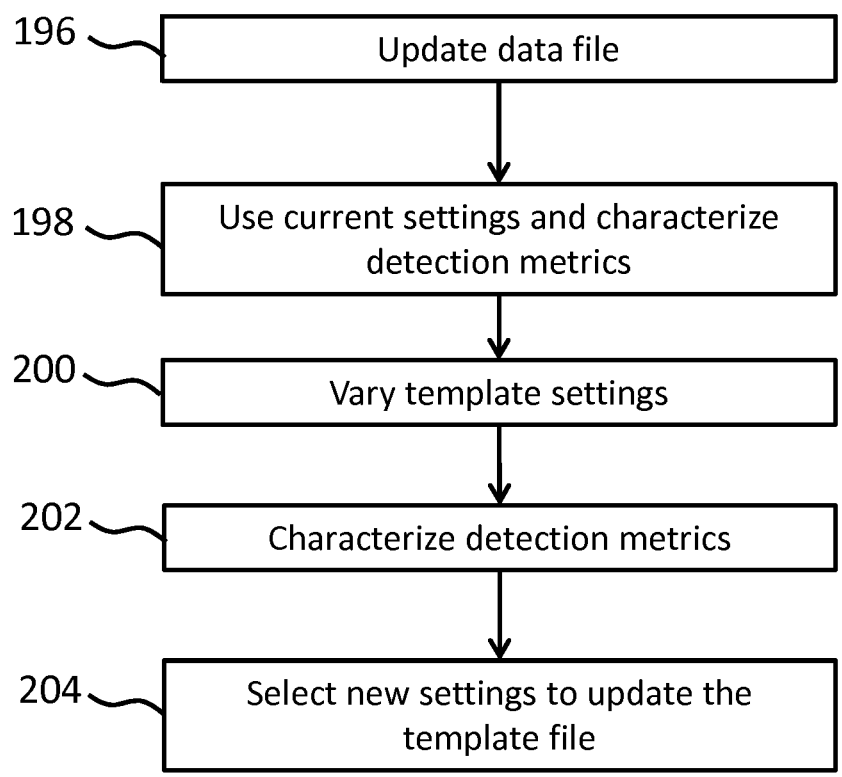
FIG. 16 illustrates one embodiment of a method of updating a template file.

To appreciate the concept of a template file and adaptive aspects of systems described herein, reference may now be made to FIGS. 15 and 16. FIG. 15 shows at a high level, a method 174 of data collection. Such a method may be used to optimize the detection of seizures. In method 174 an initial template file may be generated or selected for an individual (step 176). Once a template is generated or selected it may be added to computer memory of a detection unit and/or a base station. An example of some data that may be included in a template file was shown in Table 1.

A number of approaches may be used for establishing an initial template file. In some embodiments, a patient may be monitored for a period of time in a hospital or other controlled setting and data, such as data derived from EMG electrode outputs, may be collected and correlated with the presence or absence of seizures, i.e., general seizure characteristics for an individual may be established. From that data, an operator or software may generate an initial template file or select an appropriate file from a list of pre-generated templates. In some embodiments, an initial template file may be obtained using historical data from a general patient demographic. For example, a patient may be defined by various characteristics including, for example, any combination of age, gender, ethnicity, weight, level of body fat, fat content in the arms, fat content in the legs, fitness level, or the patient may be defined by other characteristics. The patient's medical history including, for example, history of having seizures, current medications, or other factors may also be considered. Once a template file is generated or selected it may be included in computer memory within a detection unit and base unit and an individual may use the detection unit in a home-setting.

In step 178 a patient while in a home-setting may collect and process EMG output or other detector output, such as using a detection unit. It should be noted, as indicated in FIG. 1, that a detection unit may be in communication with a base unit, transceiver and also with a data storage unit. Thus, any portion of data may be collected, processed and also sent to a data archive. In FIG. 15, the storage of detector data is illustrated in step 180. Any portion of the data, e.g., raw data or processed data may be stored. In some embodiments, data may be converted to a model form that allows one to access the data and determine how that data would have behaved if analyzed in another algorithm. For example, the noise value in periods between shaped data bursts may be stored as value and may not include a point by point data file that includes all fluctuations in the baseline. Bursts may themselves be shaped and this pattern may be stored. In some embodiments, data may be added to a storage archive and more than one different template applied to that data. That is, the data may be analyzed with any number of template files and the results of that analysis stored for future review. In that light, the results of running different pre-generated templates may be stored and not raw data or other processed data. Of course, the results of running those pre-generated templates may be evaluated and it may be determined, e.g., after comparison of those results with data reflecting the physical states of patients, that one template, i.e., a template that was not used to monitor a patient, would have in fact detected the patient's seizures in a preferred manner.

Adapting an algorithm to better detect seizures in an individual patient or patient demographic may depend not only on the organization of detector data but also upon corroborating information, e.g., for any given portion of detector data, the physical condition of the patient. That is, it may, in some embodiments, be useful to document, along with EMG or other detector data, a record of what actually occurred at certain points in a data stream. Such information may, for example, be identified by a caregiver, as indicated in step 182. A caregiver may also provide such information to a data storage facility, which may store the information (step 184). Alternatively, one caregiver may provide such information to an operator who may execute an optimization procedure. Information provided to data storage may include, for example, whether a suspected seizure was verified to be a seizure, whether a suspected seizure was in fact something different, the location of the patient when an incident occurred, severity of the seizure, time of the incident, any medical care that may have been issued and other information as well. At least some of this information may also be provided by the patient or individual.

In addition, in some embodiments, a patient may also provide information related to general seizure characteristics. For example, a patient may receive an alert from the detector unit that a seizure is in progress (step 186). An individual, if alert, and aware that they are in fact not experiencing a seizure, may be given the option of sending a message to a caregiver and/or to a data storage unit that a false positive was alerted by the system. In some embodiments, an individual may communicate the presence of a false detection by simultaneously pressing two buttons on an attached device, e.g., the detection unit or another unit. Of course, the requirement that an individual simultaneously press two buttons may minimize the risk that an inadvertent signal is sent. Any other suitable approach to minimize inadvertent messages may also be used. A message sent in this manner, e.g., sent to a storage facility from a patient (step 188), may include a time stamp to correlate a false positive event with the data which initiated the false positive event. Such information may be stored in a data storage facility (step 190).

An individual may, in some embodiments, also be given the option to provide additional information, e.g., other information that may be associated with any false positive event, or seizure incident. Such supporting information may include an activity they were engaged in or the physical location they were at when they received notification that a seizure is in progress. Also, a detector unit may, as previously described, be an input/output device, and thus, a seizure alert may be sent to a detector unit, or other unit carried or worn by a patient, from a base unit. That is, if the base unit controls initiation of an alarm, the base station may inform the detector unit (which is physically near the patient) that a seizure has been detected. In some embodiments, a device including means for reporting information, such as a false positive event, to a caregiver or data storage facility may be worn around the wrist or on the belt of a patient. An operator may access data in a data storage facility and organize the information 192.

A method 194 of optimizing seizure detection, and updating a template file, is shown in FIG. 16. In step 196 an operator may add any new data, e.g., data collected in a home-setting for a patient, to any previously stored data for that patient, i.e., an operator may update a data file. Alternatively, an operator may add newly collected data for a patient to a body of data that is associated with a patient demographic. The system may in step 198, for example, use the initial template file (or a currently used template file for that patient), and characterize detection metrics for the system as applied to the individual's updated data file. Metrics of the system may include listing seizure events that were correctly identified, seizure events that were missed, false positives, and in some embodiments, a determination of the severity of an event that was considered to be a seizure. Also, for any given reported event, e.g., a seizure incident or false positive detection, the operator may, in some embodiments, be provided with a listing of the data in different registers at the time of the event. Such information may, for example, be recalculated (during optimization) from original signal data or from stored values. In a step 200, the operator may execute a computer program to select fields of information, e.g., weighting coefficients, thresholds, criteria, and selected processing routines, from the initial template file (or currently used template) and vary those fields. The operator may also manually select and adjust one or more fields. The system may characterize detection metrics (step 202) while varying template fields and select new settings (step 204) for an updated template file. Of course, the updated template file may be downloaded to either or both of the detection unit and base station.

One aspect of methods and apparatuses described herein is that they are, in various embodiments, able to organize information between a detection unit and base station or between those units and a data archive. In addition, some embodiments may be used to organize the collection of portions of data that are most relevant.

Figure 17:
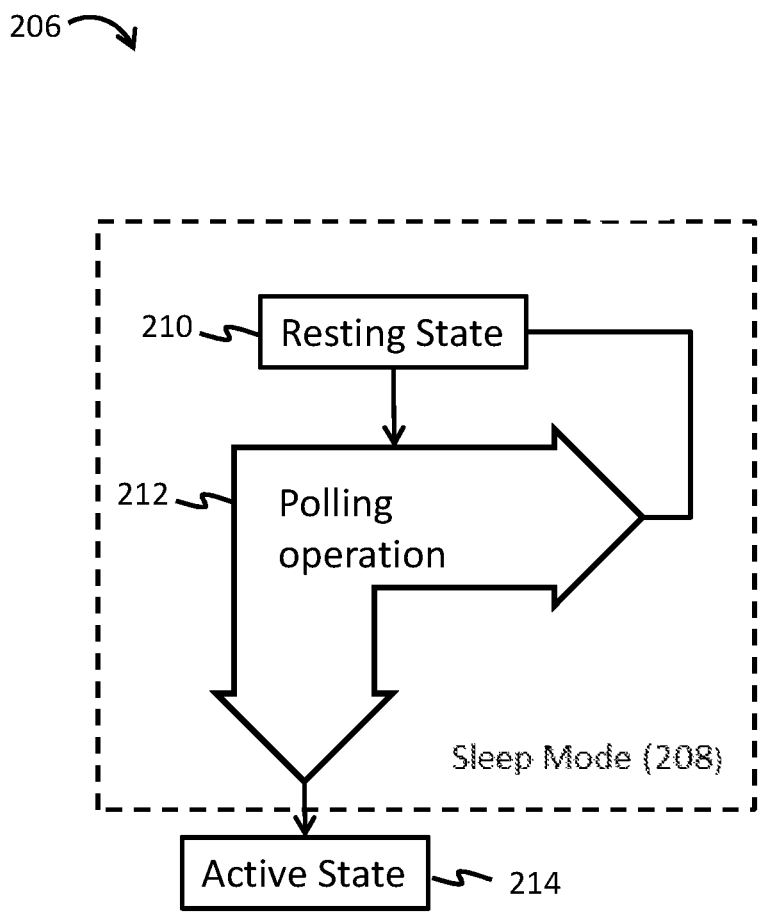
FIG. 17 illustrates one embodiment of a method of adjusting the state of a detection unit in a method of seizure monitoring.

In some embodiments, the rate at which data may be collected may depend upon whether or not an electrode is in a given state, such as an active state, resting state, or engaged in a polling operation. For example, FIG. 17 illustrates one embodiment of a method 206 of detecting seizures in which the rate of data collection depends upon the state of an electrode. Method 206 may, for example, be used to toggle a detection unit and/or base station between a "sleep" mode, i.e., characterized by operations within dashed line 208, and a mode of substantially continuous operation, such as active state 214. As shown in FIG. 17, a detector and/or base unit may be configured to exist in the resting state 200 for a portion of time while in a "sleep mode." While in the resting state 210 a detector or base unit may be silent, e.g., it may not be monitoring or collecting data from a patient. The resting state may include instructions to periodically exit the resting state 210 and, for example, collect detector data for a period of time. That is, a detector may enter a polling operation step 212 where data is collected. The duration of an individual polling operation may be sufficient to collect data as needed to make a decision regarding the state of an electrode. That is, for example, based on data collected during polling step 212 a detector may revert back to the resting state 210 or may enter another state, such as active state 214.

Any of various routines may be used to collect data for toggling between a resting and active state. An amplitude detection algorithm may, for example, be used to switch an electrode between a resting and active state. FIG. 18 illustrates one embodiment of an amplitude detection algorithm 216. An EMG signal amplitude may be, for example, a peak value, a mean value, a median value, an integrated value, or other value that may be measured at a given time point or over a selected time interval. EMG signal amplitude may be normalized or calibrated for a patient's baseline activity. As shown in FIG. 18, in a step 218 one or more electrodes in a resting state may "wake up" and measure the EMG signal amplitude. For example, as illustrated in step 220, if the amplitude is above a threshold level, then the one or more electrodes may continue to measure the EMG signal amplitude and if the threshold level is not obtained, the one or more electrodes may return to a resting state. By having a period of time in which a detection unit is in "sleep" mode, a system may conserve battery life, minimize the amount of data that is stored in memory, minimize the amount of data that is transferred over a network, or serve other functions. In some embodiments, a decision to enter an active state, and monitor a patient in a more continuous manner, may be made based on factors in addition to amplitude detection.

Figure 19:
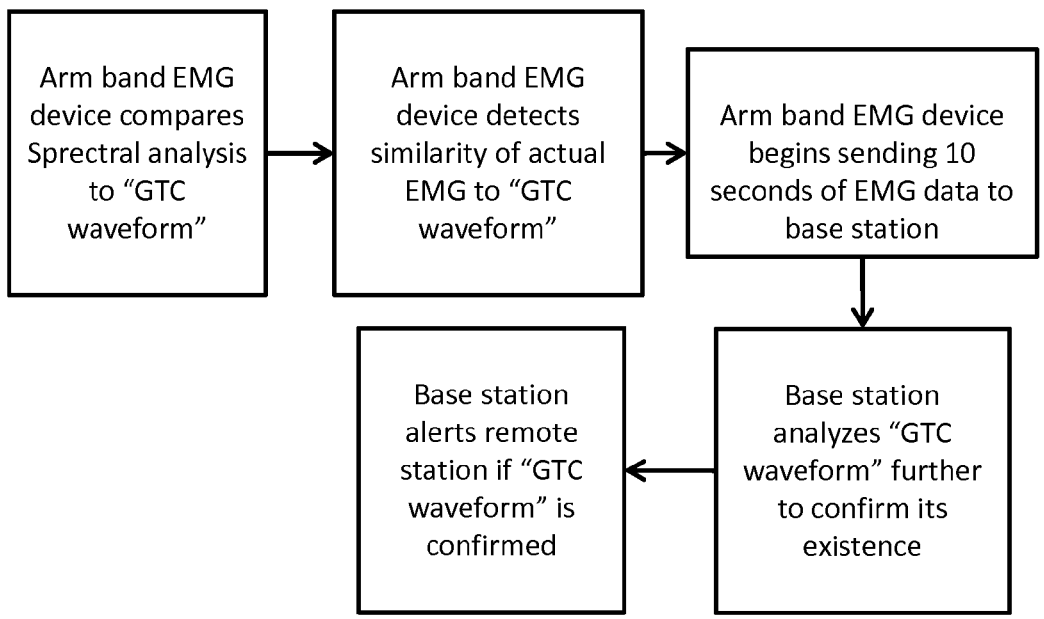
FIG. 19 illustrates a further embodiment of a method for detecting seizure related incidents.
Figure 20:
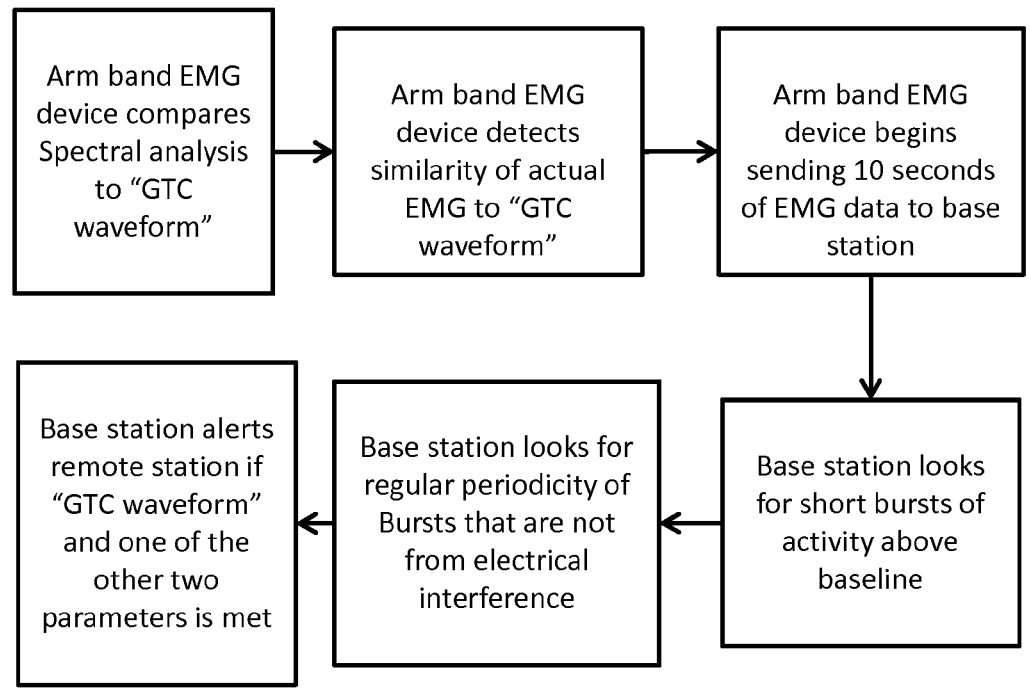
FIG. 20 illustrates a still further embodiment of a method for detecting seizure related incidents.

Additional embodiments that may be used to allocate data collection among devices are shown in FIGS. 19 and 20. In the embodiment of FIG. 19, an EMG electrode in a detection unit detects an EMG signal, determines the spectral content of the signal, and may compare the spectral content to a model GTC waveform stored in the detection unit's memory. If the spectral content is substantially similar to the GTC waveform, then the detector unit may send approximately ten seconds-worth of EMG signal to the base station. Preferably, the sent EMG signal includes the signal that formed the basis of the comparison. The base station may independently determine the spectral content of the received signal, and compare the spectral content to the GTC waveform stored at the base station. If the spectral content is substantially similar to the GTC waveform, then the base station may send an alert to a remote station or caregiver. Thus, in one embodiment, for an alert to be sent, both the detection unit and base station must each determine that the spectral content of the EMG signal is substantially similar to the GTC waveform.

In the embodiment of FIG. 20, an EMG electrode in a detection unit detects an EMG signal, determines the spectral content of the signal, and compares the spectral content to the GTC waveform stored in the detection unit. If the spectral content is substantially similar to the GTC waveform, then the detector unit may send approximately ten seconds-worth of EMG signal to the base station. Preferably, the sent EMG signal includes the signal that formed the basis of the comparison. The base station may independently determine the spectral content of the received signal, and compare the spectral content to the GTC waveform stored at the base station. The base station may also analyze the received signal for burst activity, as described above, such as regular periodicity, to determine if burst thresholds are met.

If the spectral content is substantially similar to the GTC waveform, and the base station recognizes burst activity that meets the burst thresholds, then the base station may send an alert to a remote station or caregiver.

Similarly, processing of EMG signal data for various seizure variable values may be accomplished at the detection unit, at the base station, or both, depending on processor existence and capability and storage capacity.

Some additional processing techniques that may be used in the above algorithms or in other sub-methods are described below. For example, in some embodiments, a register may be populated in a manner such the level, or value of the contents, of the register is related to the time that a seizure variable may be above threshold, related to the magnitude of a certain characteristic of data, e.g., seizure variable, or both. For example, a register may be loaded with a set numerical value every X seconds that a certain characteristic is maintained above a threshold. Thus, if a given number of time periods, e.g., nX seconds, are maintained with the characteristic above threshold, the method may advocate a seizure detection. If the characteristic drops below threshold, the register may be reset or decremented in some manner. In such an embodiment, an alarm may be triggered based on the number of time periods that a certain characteristic is above threshold. A register (e.g., a first register) may also be loaded with a numerical value every X seconds that a certain characteristic is above a threshold, and that numerical value may be proportional to the magnitude of signal or number of events detected over the provided time period. At the completion of every X seconds, a second register may be populated in a manner that depends upon the first register, e.g., whether it is maintained above a certain level. In such an embodiment, an alarm may be triggered, for example, if the second register is populated for a certain number of consecutive time periods. The first register may, in some embodiments decrement at a certain rate. For example, the first register may be loaded every X seconds in a manner proportional to the magnitude or number of registered events and also decremented each X second period. Thus, the first register may either increase in value or decrease in value as dependent upon how it is incremented or decremented. In some embodiments, an alarm may be triggered if either the second register exceeds a certain threshold, if the first register exceeds threshold, or if either or both exceeds a certain threshold. If a characteristic evaluated is of a type where an integration calculation is needed, then the method may increment the register a specific amount every X seconds. If the register is set to decay more slowly than the rate of increment, then the register value will increase over time. A slower rate of increase may allow the method to slowly build up to a higher confidence level of seizure detection.

In some embodiments, an EMG electrode in a detection unit may detect an EMG signal, determine the spectral content of the signal, and compare the spectral content to the GTC waveform stored in the detection unit. If the spectral content is substantially similar to the GTC waveform, then the detector unit may send an alert to the base station, a remote station, and or caregiver. The detector unit may send the alert without requiring corroborative analysis by the base station. In yet other embodiments, the detector unit may further analyze the EMG signal for seizure burst activity, as described above, such as regular periodicity, to determine if burst thresholds are met. If the spectral content is substantially similar to the GTC waveform, and the detector unit recognizes burst activity that meets the burst thresholds, then the detector unit may send an alert to a base station, a remote station and/or caregiver.

In some embodiments, the seizure detection system may be provided with a generalized GTC waveform and calibrated for a patient's baseline activity, e.g., sleeping, daytime activity, etc. When waveform activity increases, the seizure detection system may compare the signals collected by the detection unit to the generalized GTC waveform. The seizure detection system may begin to characterize the signals and look for elevated signal amplitudes. The seizure detection system may process the signals to generate spectral content by well understood methods such as Fast-Fourier Transform (FFT). The seizure detection system may apply filtering to more clearly reveal higher-frequency "bursts." The seizure detection system may determine if the processed signal fits the generalized seizure characteristics by measuring one or more of the factors of amplitude, count, time length of train, and periodicity of bursts and comparing those factors against stored patterns and thresholds. If the thresholds are exceeded, then an alarm may be sent, e.g., to the base station together with data. The base station may separately process the data for verification of the alarm condition. If the base station agrees with the alarm, then the base station may generate an alarm to remote devices and local sound generators. An alarm may comprise an audible signal, or a text message, or email, or trigger vibration in a PDA, or other suitable attention-getting mechanisms. In some embodiments, having the base station agree to the detection unit's alarm introduces a voting mechanism for reducing false alarms. Both devices must vote on the decision and agree to sound the alarm. This may be used to limit false alarms. Of course, a processor in a patient-mounted unit may process the EMG signals based on burst detection, and may separately process the EMG signals based on GTC waveform, and may send an alert if both processes indicate that an alarm protocol should be initiated. Thus, voting may occur within a device, as well.

In some embodiments, during or after a seizure event, a human operator may review and adjust thresholds based upon the severity of the seizure or possibly the non-detection of an actual seizure because of high thresholds. Many people have seizures and do not realize that they had a seizure, e.g., the short-lived seizures discussed above. Having this data to review may help medically manage the person with seizures. Also, a human operator may evaluate the data and conclude that a seizure did not occur, and either cancel the alarm or instruct the seizure detection system that the detected waveform did not indicate a seizure. Likewise, a human operator may instruct the seizure detection system that an undetected seizure had occurred by, e.g., specifying the time during which the seizure occurred. For example, the graphs in the figures discussed above may comprise a rolling "window" of EMG activity, and the human operator may "rewind" the recorded signal and indicate to the seizure detection system the time window in which the seizure occurred. In some embodiments, the base unit may include a visual display that allows display of EMG signals in time and spectral domain to allow a caregiver to view historical seizure data. In some embodiments, the base station may visually depict the signal and provide a graphic user interface (GUI) that allows human operators to accomplish the "window" selection and define other operating thresholds and conditions. For example, the system 10 of FIG. 1 may include a video camera that records the patient while sleeping to allow a caregiver to review the EMG signal in coordination with video footage to assess a patient's condition corresponding that EMG signal. Thus, video data may be stored along with EMG signal data, and reviewed, for example, on the base station GUI along with the EMG signal graphs. In other words, the base station could allow a caregiver to view EMG signal graphs and corresponding video data side-by-side. The seizure detection system may thus have additional data points against which to evaluate future seizure events for that particular patient. The seizure detection system may employs adaptively intelligent software to "learn" the patient's seizure patterns, and over time effectively customize the generalized GTC waveform to better detect seizures in that patient.

An apparatus for detecting seizures is preferably man-portable, and may include a detection unit that may be attached to the body, such as by use of an elastic arm band. The detection unit may be battery powered, and may wirelessly communicate with the base station. The detection unit may include sufficient data storage, processing and transmission capability to receive, buffer, process and transmit signals. The detection unit may process the signals and conduct a simplified comparison, e.g., using two factors of amplitude and frequency, with the generalized seizure detection requirements stored in the detection unit. When the detection unit determines that a seizure is occurring, it can download both its analysis and the raw signal data to a bedside base station for more complex processing. The base station may have much more power, larger storage capability and greater processing speed and power, and be better able overall to process the information. It could have a larger database of patterns to compare against. As the seizure detection system "learns" the patient's patterns, the base station may modify the generalized seizure detection requirements to more closely model the patient's pattern. The base station may update the detection device periodically with the modified generalized seizure detection requirements. Likewise, the base station may transmit raw and processed signal data to a remote computer for further analysis and aggregation with signal data from other units in use. For example, multiple base stations may transmit data for multiple patients to a remote computer. Each base station may not receive the other base station's data, but the remote computer may serve as a common repository for data. Aggregation of the data may allow further data points upon which to further refine the generalized seizure detection requirements, thresholds and statistical information that may be supplied to base stations and detection units as a factory default.

As previously noted, in some embodiments, in addition to using EMG, electrocardiography (ECG) may be used to corroborate (or contradict) the occurrence of a seizure. This option could be used with particularly difficult patients. Patients with an excessive amount of loose skin or high concentrations of adipose tissue may be particularly difficult to monitor. For example, a factor associated with reliable EMG measurements, is the stability of the contact between the electrodes and skin. For some patients this may be difficult to achieve in a reliable manner ECG data may be included in a method for determining a likelihood of whether a seizure related incident is taking place (or has taken place) and ECG data may be used to determine whether a seizure should be declared, e.g., an alarm initiated. Moreover, skin and fat are inherently a type of frequency filter.

Heart rate may, for example, elevate during a seizure, e.g., a patient may become tachycardic. As discussed further herein, if the EMG processing portion of the seizure detection apparatus determines that a seizure may be in progress and the heart rate does not go up, then the confidence of the detection may be reduced. For example, epileptic patients that use a beta blocker drug may not experience a rise in heart rate. In such situations, a method incorporating heart rate as a factor may be provided with a coefficient to lower the weight given to that factor. Thus, the disclosed detection method and apparatus may be adjusted or readily customized according to patient-specific considerations, such as use of a particular drug regimen. In some embodiments, ECG may be used to detect other cardiac dysrhythmia, such as bradycardia or asystole following a seizure, and to send an alarm if such a condition is detected. Data from a temperature sensor situated as to detect patient temperature may also be used to corroborate occurrence of a seizure or to initiate an alarm.

Generally, the devices of a seizure detection system may be of any suitable type and configuration to accomplish one or more of the methods and goals disclosed herein. For example, a server may comprise one or more computers or programs that respond to commands or requests from one or more other computers or programs, or clients. The client devices, may comprise one or more computers or programs that issue commands or requests for service provided by one or more other computers or programs, or servers. The various devices in FIG. 1, e.g., 12, 13, 14, 16, 17, 18 and/or 19, may be servers or clients depending on their function and configuration. Servers and/or clients may variously be or reside on, for example, mainframe computers, desktop computers, PDAs, smartphones (such as Apple's iPhone™, Motorola's Atrix™ 4 G, and Research In Motion's Blackberry™ devices), tablets, netbooks, portable computers, portable media players with network communication capabilities (such as Microsoft's Zune HD™ and Apple's iPod Touch™ devices), cameras with network communication capabilities, wearable computers, and the like.

A computer may be any device capable of accepting input, processing the input according to a program, and producing output. A computer may comprise, for example, a processor, memory and network connection capability. Computers may be of a variety of classes, such as supercomputers, mainframes, workstations, microcomputers, PDAs and smartphones, according to the computer's size, speed, cost and abilities. Computers may be stationary or portable, and may be programmed for a variety of functions, such as cellular telephony, media recordation and playback, data transfer, web browsing, data processing, data query, process automation, video conferencing, artificial intelligence, and much more.

A program may comprise any sequence of instructions, such as an algorithm, whether in a form that can be executed by a computer (object code), in a form that can be read by humans (source code), or otherwise. A program may comprise or call one or more data structures and variables. A program may be embodied in hardware or software, or a combination thereof. A program may be created using any suitable programming language, such as C, C++, Java, Perl, PHP, Ruby, SQL, and others. Computer software may comprise one or more programs and related data. Examples of computer software include system software (such as operating system software, device drivers and utilities), middleware (such as web servers, data access software and enterprise messaging software), application software (such as databases, video games and media players), firmware (such as device specific software installed on calculators, keyboards and mobile phones), and programming tools (such as debuggers, compilers and text editors).

Memory may comprise any computer-readable medium in which information can be temporarily or permanently stored and retrieved. Examples of memory include various types of RAM and ROM, such as SRAM, DRAM, Z-RAM, flash, optical disks, magnetic tape, punch cards, EEPROM. Memory may be virtualized, and may be provided in, or across one or more devices and/or geographic locations, such as RAID technology.

An I/O device may comprise any hardware that can be used to provide information to and/or receive information from a computer. Exemplary I/O devices include disk drives, keyboards, video display screens, mouse pointers, printers, card readers, scanners (such as barcode, fingerprint, iris, QR code, and other types of scanners), RFID devices, tape drives, touch screens, cameras, movement sensors, network cards, storage devices, microphones, audio speakers, styli and transducers, and associated interfaces and drivers.

A network may comprise a cellular network, the Internet, intranet, local area network (LAN), wide area network (WAN), Metropolitan Area Network (MAN), other types of area networks, cable television network, satellite network, telephone network, public networks, private networks, wired or wireless networks, virtual, switched, routed, fully connected, and any combination and subnetwork thereof. The network may use a variety of network devices, such as routers, bridges, switches, hubs, repeaters, converters, receivers, proxies, firewalls, translators and the like. Network connections may be wired or wireless, and may use multiplexers, network interface cards, modems, IDSN terminal adapters, line drivers, and the like. The network may comprise any suitable topology, such as point-to-point, bus, star, tree, mesh, ring and any combination or hybrid thereof.

Wireless technology may take many forms such as person-to-person wireless, person-to-stationary receiving device, person-to-a-remote alerting device using one or more of the available wireless technology such as ISM band devices, WiFi, Bluetooth, cell phone SMS, cellular (CDMA2000, WCDMA, etc.), WiMAX, WLAN, and the like.

Communication in and among computers, I/O devices and network devices may be accomplished using a variety of protocols. Protocols may include, for example, signaling, error detection and correction, data formatting and address mapping. For example, protocols may be provided according to the seven-layer Open Systems Interconnection model (OSI model), or the TCP/IP model.

Although the foregoing specific details describe certain embodiments of this invention, persons reasonably skilled in the art will recognize that various changes may be made in the details of this invention without departing from the spirit and scope of the invention as defined in the appended claims and considering the doctrine of equivalents. Therefore, it should be understood that this invention is not to be limited to the specific details shown and described herein.

Additional information related to the methods and apparatus herein described may be understood in connection with the examples provided below.

EXAMPLES

Example 1

In one example, a patient who may be susceptible to having seizures may be monitored. The patient may, for example, be monitored during a period immediately following a hospitalization, or at some other time where they are at risk for SUDEP. It may be useful to set up the monitoring protocol for the patient, based at least in part, upon data obtained for the patient while the patient is monitored for seizures in a controlled setting. For example, during hospitalization the patient may be monitored and data may be collected for determining general seizure characteristics. The patient may, for example, be monitored with EMG over a period of several days, or some other interval, as necessary to collect data associated with a statistically significant number of seizures. During the period of hospitalization, the patient EMG data may be collected by placing bipolar differential electrodes on or near one or more pairs of muscles, e.g., agonist and antagonist muscle pairs. EMG data may, for example, be collected from a first group of muscles, e.g., the biceps and triceps, and a second group of muscles, e.g., the hamstrings and quadriceps. EMG data from time periods with known seizures and also intervals with non-seizure periods may be collected, archived and an operator may analyze the data.

An operator may analyze the data and characterize how the patient data relates to a seizure variable, including, for example, seizure variables characteristic of a burst. An operator may, for example, measure the amplitude, width, and determine the signal to noise (S/N) ratio for portions of data that are elevated, i.e., periods that may be characterized as data bursts. Signal to noise calculations may involve, establishing a baseline by determining fluctuations in detector signal, i.e., baseline noise, in a time period immediately prior to data in a time suspected of containing bursts. Various filters may be applied to the data, e.g., digitized data may be subjected to a 3rd order Butterworth filter from 300 Hz to 500 Hz or filtered in another manner. Using data that is filtered, the operator may, for example, repeat measurement of amplitude, width, and signal to noise (S/N) ratio for data at times that appears to contain data bursts. The operator may then select threshold values associated with burst measurements. Alternatively, an operator may opt to use threshold values typical for all patients or patients of a certain demographic.

Similarly, an operator may, for example, determine the frequency position of local minimum values and local maximum values of power density for the spectral data. For example, data from a certain time window, such as five seconds, may be collected and converted to spectral data (in the frequency domain). The operator may determine local maximum and minimum values and specify a range of frequencies on either side of the local maximum value and local minimum value and an algorithm may calculate the area under the power density/frequency curves. The ratio of these areas may be used as the value of a seizure variable, e.g., a slump to bump ratio. A threshold value for the slump to bump ratio may be specified by the operator or selected from a template file for all patients, or patients of a certain demographic.

Figure 21:
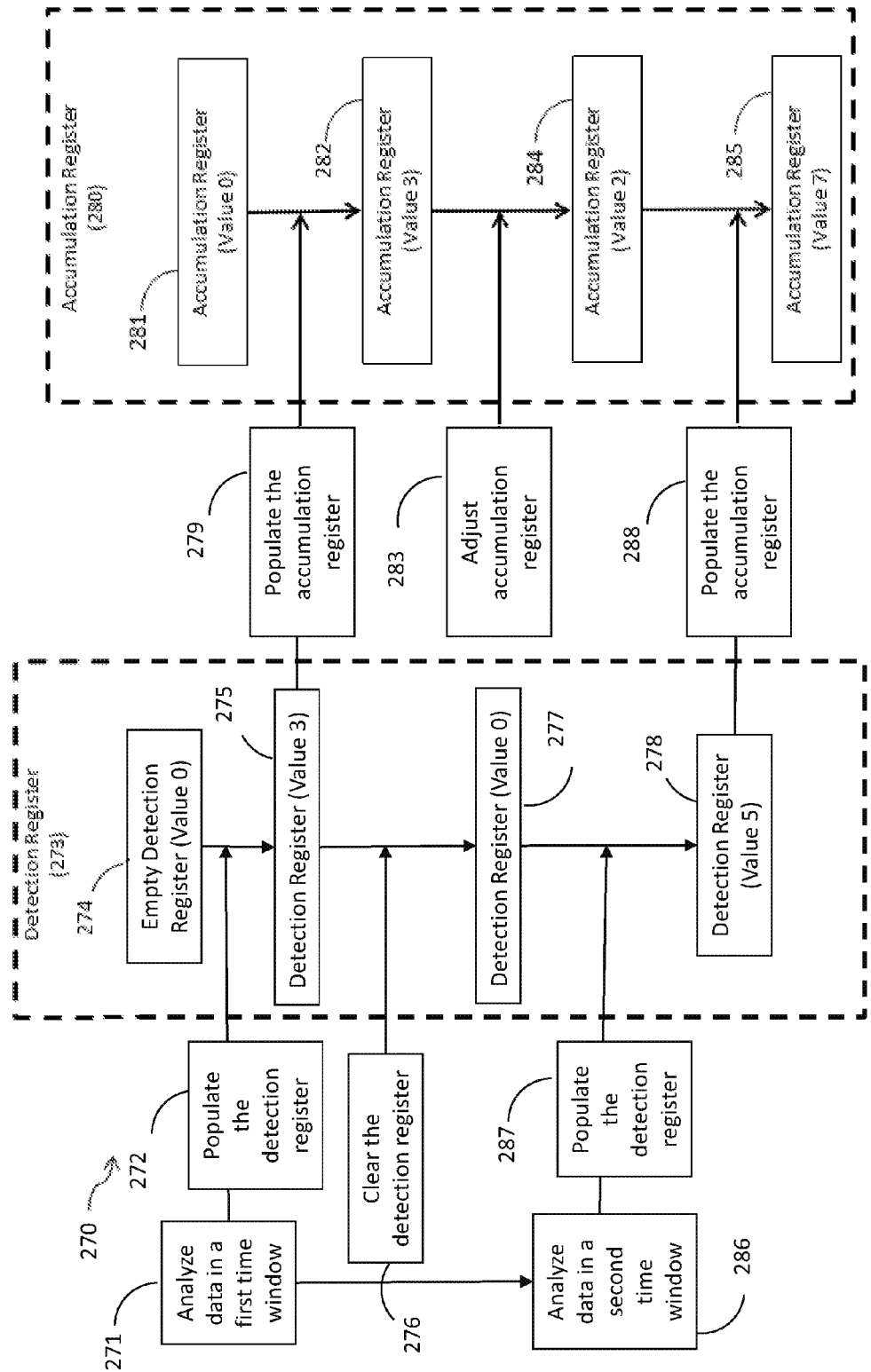
FIG. 21 illustrates how model data in a procedure for analysis of data bursts may be organized.

An operator may import archived data, i.e., data from periods collected in which a seizure was present and other non-seizure periods, into a computer program using the selected threshold values and instructions for executing an algorithm. The algorithm may, for a given time window, e.g., 5 seconds, calculate values of burst related seizure variables. For example, for any time period, software may detect possible bursts, and may also measure amplitude, width and S/N. If bursts meet the criteria established, e.g., are within the set thresholds, the computer may populate a value in a burst detection register. To clarify the flow of data in the algorithm, model data from Example 1 may be referenced to FIG. 21. FIG. 21 shows how model data in a procedure (270) for analysis of data bursts may be organized, and how data may be transferred between a detection register in computer memory and an accumulation register, also in computer memory. In a first interval of time (271), data may be analyzed, and for example, it may be determined that three events meet threshold requirements for characterization as bursts. In a step (272) data may be transferred to a detection register. The detection register (273) in FIG. 21 is represented by dashed line (273), and the flow of information within the detection register (273) is represented by blocks (274, 275, 277, and 278), which represent the detection register (273) in different states. As data is transferred in step (272), the detection register in a state (274), i.e., storing a data value of zero, may become populated with a value of three, as shown in state (275). In a step (279), the data value stored in the detect register (273) may be transferred to an accumulation register (280). In FIG. 21 the burst train accumulation register (280) is represented by dashed line (280), and the flow of information within the burst train accumulation register (280) is represented by blocks (281, 282, 284, and 285), which represent the accumulation register in different states. In step (279), the accumulation register in a state (281), i.e., a store storing a data value of zero, may become populated with a value of three, as reflected in state (282). Referring back to the detection register (273), upon transferring contents to the accumulation register (280), in step (276), the detection register (273) may clear its contents, as reflected in state (277). As reflected in step (286), in a second interval of time (286), another interval of data may be analyzed, and for example, it may be determined that five events meet threshold requirements and are characterized as bursts. In step (287), the detect register (273), now in state (277) may receive data associated with the measured burst value from step (287), i.e., a value of five. The detect register (273) may now hold a data value of five, as shown by state (278). Prior to transfer of data from the detect register, i.e., in state (278) to the burst train accumulation register (280), the burst train accumulation register (280), may be subjected to an adjust accumulation register step (283). That is, in step (283) the burst train accumulation register may be adjusted in value. For example, as illustrated in Example 1, the accumulation register is shown to "leak" a value of one during the adjust accumulation register step (283). Thus, if step 283 denotes a leakage value of one and if a greater number of bursts are detected in successive time intervals, e.g., steps (271) and (286), then the accumulation register will increase in value. For example, as shown in Example 1, in step (288), the detect register (273) transfers its contents to the burst train accumulation register (280), while the burst train accumulation register is in state (284), and a value content of five is transferred to the burst train accumulation register (280). The accumulation register would then hold a data value of seven, as shown for state (285).

In addition to the steps above, an algorithm may also involve other registers, e.g., a GTC accumulation register. For example, as described in relation to FIG. 22, a GTC accumulation register (290) may be populated. Thus, it should be appreciated that at any point in time, the burst train accumulation register (280) and the GTC accumulation register (290) may hold a value. A supervisory algorithm (162), may be used to analyze the data in those registers (285) and (290). To clarify the flow of data in Example 1, reference is now made to FIG. 22, as well as the general description of supervisory algorithms in FIG. 14.

Figure 22:
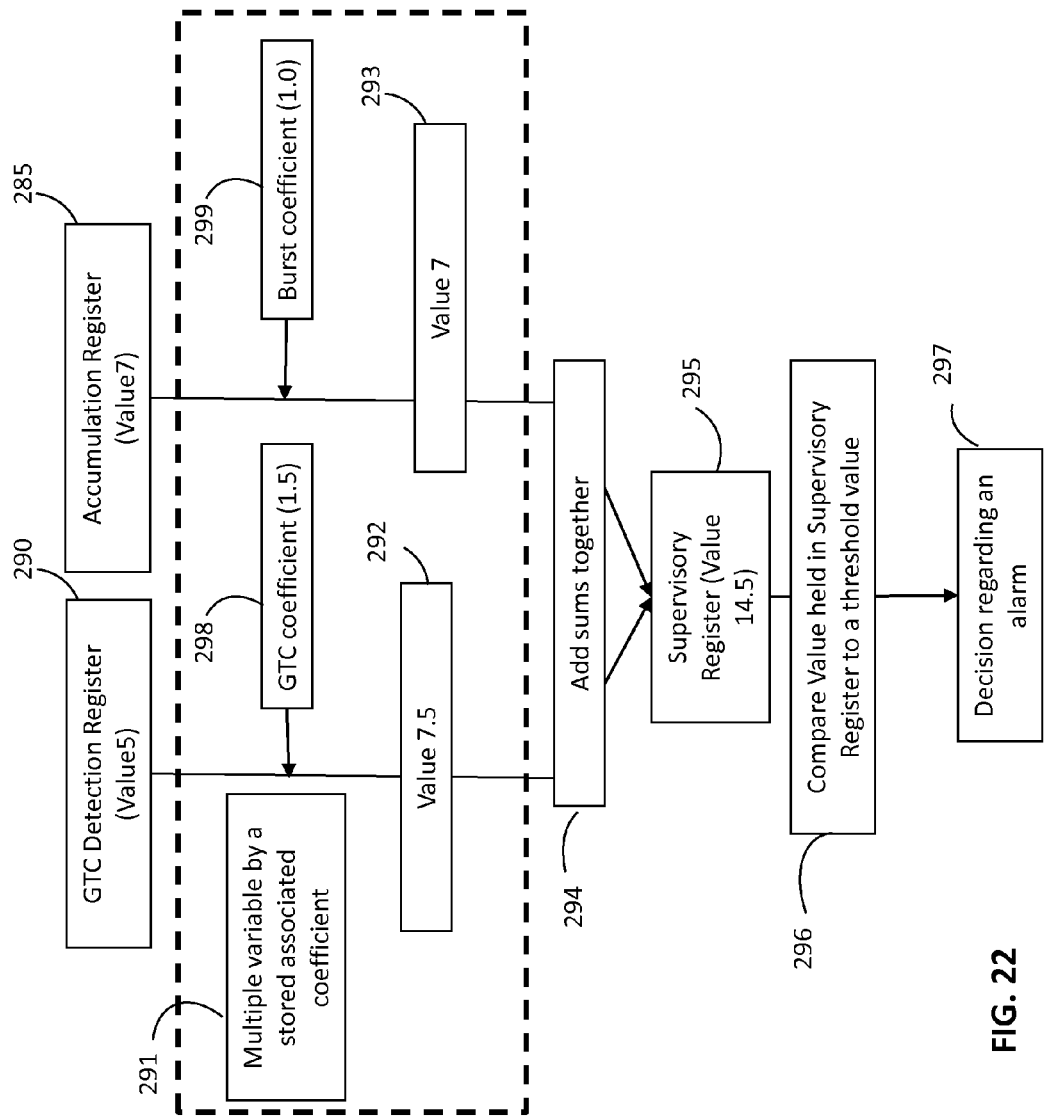
FIG. 22 illustrates how model data for analysis of data bursts is combined with data from a GTC accumulation register and how data in those registers may be analyzed in a supervisory algorithm.

As shown in FIG. 22, and using illustrative data for this Example 1, the GTC accumulation register (290) is shown to have a value of five. The burst train accumulation detection register (280) is shown to be in a state (285), and as noted previously, holds a value of seven. In a step 291 of the supervisory algorithm, the values of the registers are multiplied by a coefficient. That coefficient may be pulled from a template file and used as a weighting factor for associated seizure variables. That is, as shown in Example 1, a GTC weighting coefficient (298) may be 1.5 and a burst coefficient (299) may have a value of 1.0. The, weighted value of the two seizure variables following multiplication with their associated coefficients may then be 7.5 (292) and 7 (293). In a step (294) those values may be added together, and as shown in FIG. 22, a sum value, e.g., 14.5, may become associated with a supervisory register (295). In a step (296) the value of held in the supervisory register (295) may be compared to a threshold value. For example, a threshold value for reporting a seizure may be 14, and thus, an alarm protocol would be triggered.

In Example 1, the data that is input into the algorithm is historical data from a patient's time in the hospital. Thus, the operator may in step (297) compare the results determined by the algorithm to the actual state of the patient at the time that the data was collected. That is, an operator may compare the result that would have been initiated with the actual course that was appropriate. An operator may thus compare, for all of the data that is available, how accurately the algorithm detects actual seizures and whether the algorithm would have detected any false positives, e.g., decisions to declare an alarm when the proper course of action was to not report a seizure incident.

The computer program may allow the operator to manually adjust coefficients, including for example threshold values for burst or GTC waveform detection (such as slump to bump), GTC coefficient (298), burst coefficient (299), or combinations thereof. The program may be set to automatically adjust any combination of the aforementioned coefficients in an optimization routine, wherein the computer may modify the coefficients and look for an ideal combination that provides both accurately detects seizures and also minimizes false positive detections.

The patient in Example 1 may be sent home and monitored with a configuration of EMG electrodes that closely resembles the configuration of EMG electrodes used to optimize the detection algorithm. As the patient is monitored, data may be collected and the presence of any detected seizures, missed seizures (if present), and false positives may be reported. The system may periodically analyze the available archived data, including any archived data derived while the patient is at home, and re-optimize a combination of coefficients. Thus, the system may adapt to better monitor a given patient over time.

Example 2

In this Example 2, a patient may be set up to be monitored in a home setting using a pair of EMG electrodes on the biceps and triceps. The patient may be set up to be monitored based on a template file for patients that share a demographic with the patient. In Example 2, the patient may be an obese male and an initial set of coefficients and thresholds may be used to monitor the patient based on a set of coefficients and thresholds optimized for the entire set of data from all obese males for which data is available. As distinguished, from Example 1, the patient in this example may be monitored without previous evaluation in a hospital setting. That is, the patient may be monitored with weighting coefficients derived entirely by importing values associated with other patients, e.g., patients that share characteristics with the patient. The patient in Example 2 may be monitored for several weeks and the system may record electrode data. For the model data in Example 2, the system may accurately detect five seizure events but miss one seizure event. The system may then be optimized with archived data from the patient. That is, data from the patient may be used to adjust coefficients to improve the accuracy of detecting all events.

Example 3

Figure 23:
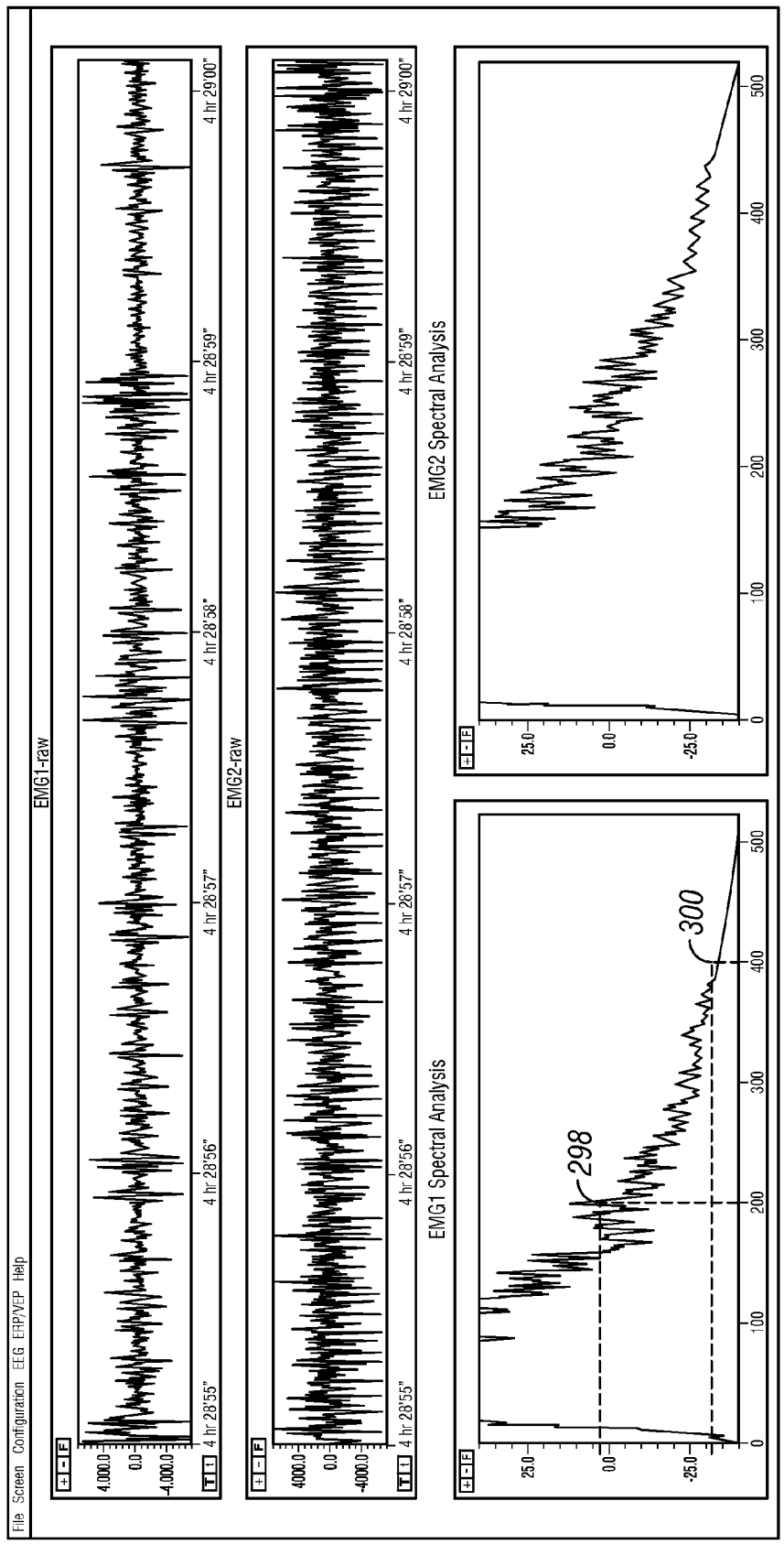
FIG. 23 illustrates exemplary EMG electrical data for a patient.

In FIG. 23, the top trace labeled "EMG1-raw" shows EMG electrical activity using a bipolar EMG electrode arrangement. The trace labeled "EMG2-raw" is from a similar bipolar electrode arrangement (differential electrode) on the triceps of the same arm. The vertical scale in the FIG. 23 graphs, EMG1-raw and EMG2-raw, is signal amplitude, e.g., the differential signal between either the pair of EMG electrode inputs on the biceps or the differential signal between the pair of EMG electrode inputs on the triceps, and the horizontal scale shows time (in FIG. 23, the time window is approximately 4 h28'55" to approximately 4 h29'00"). FIG. 23 shows the collection of 5 seconds worth of patient data. In some embodiments, data may be collected over some other time period. Attachment of EMG electrodes on opposing muscle groups, e.g., such as the biceps and triceps, may be beneficial for several reasons. For example, as further discussed below, an electrode configuration that involves opposing muscles may be useful in the interpretation of data wherein a patient is involved in certain activities, e.g., non-seizure motion, and differentiation of data collected while the patient is engaged in such activity from electrode data collected while the patient is experiencing a seizure.

Still referring to FIG. 23, the bottom left graph (labeled "EMG1 Spectral Analysis") is a representation of the frequencies of data collected from the EMG electrode over the biceps (spectral content). The bottom right graph (labeled "EMG2 Spectral Analysis") is a representation of the frequencies of the triceps EMG electrode. Data collected over a given time period, i.e., time domain electrode data, may be converted to frequency data, i.e., spectral content, using techniques such as Fast-Fourier Transform (FFT). For the spectral data, the horizontal scale is signal frequency, and the vertical scale is the signal amplitude, which for the spectral data described herein may be referred to as the spectral density. Note that the spectral data in FIG. 23 indicates a curving slope with decreasing amplitude as the frequency increases, i.e., the spectral density generally decreases as the frequency increases. The ratio of spectral density at low frequencies to the spectral density at higher frequencies is a seizure variable that, for any given set of electrode data, may have an associated value. For example, for the data shown in FIG. 23 the ratio of spectral density at a frequency of about 200 Hz (298) to the spectral density at about 400 Hz (300) may have a value of about 5.0. The ratio of spectral densities at those frequencies, or at other frequencies, may be a seizure variable and the value of that seizure variable, such as derived from data in FIG. 23, may be generally characteristic of non-seizure muscle activity, such as moving in bed or moving arms. In some cases, such as in FIG. 6, where the ratio at 200 Hz to 400 Hz is lower, such a ratio may be indicative of seizure activity.

Example 4

Figure 24:
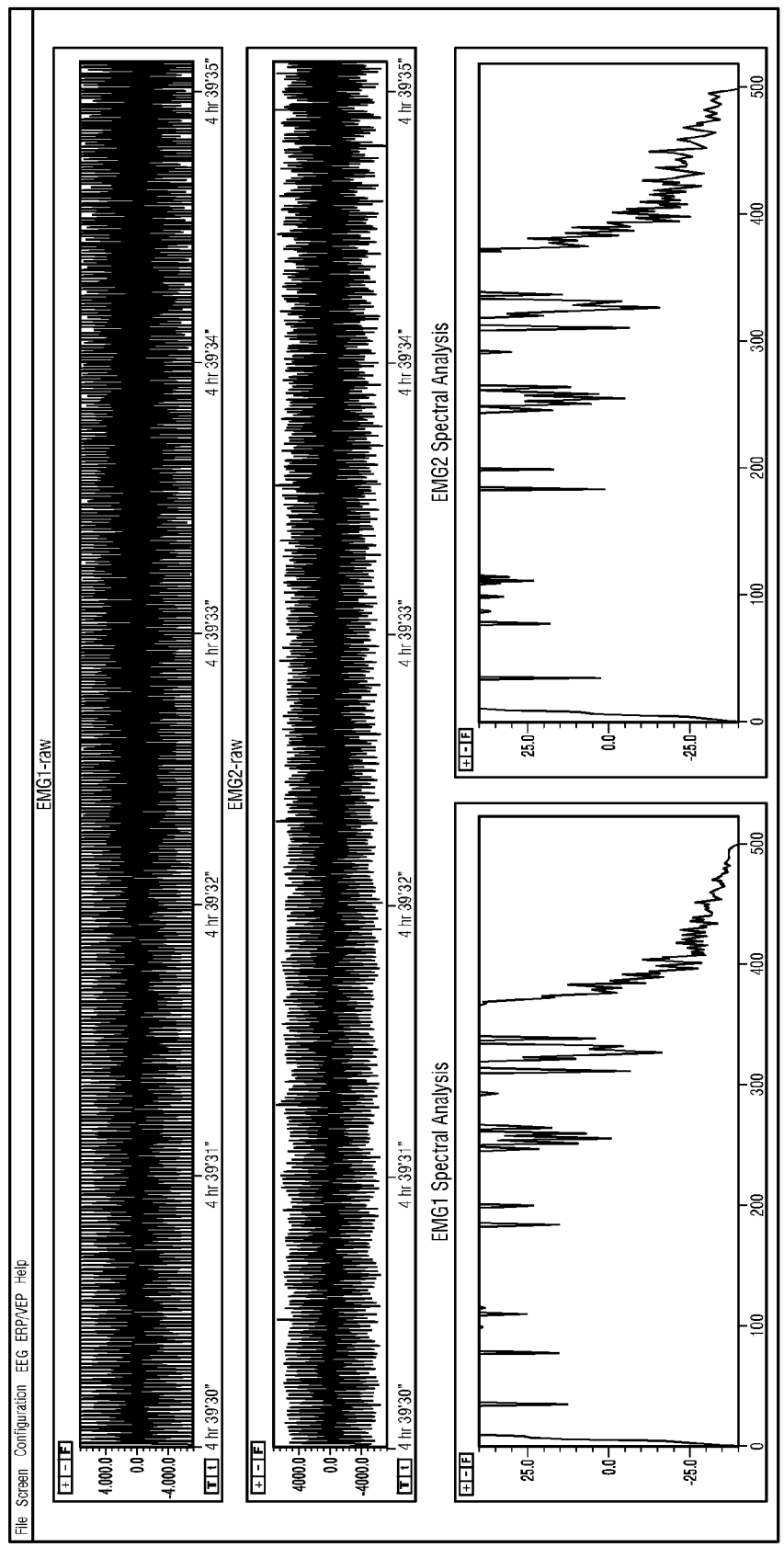
FIG. 24 illustrates exemplary EMG electrical data for a patient while non-seizure moving.

FIG. 24 provides a spectral graph of EMG signals at a different window of time than those of FIG. 23, namely, from approximately 4 h39'30" to approximately 4 h39'35" when the patient is again non-seizure moving. The spectral graph shows a high spectral density across a wide group of frequencies in the frequency band. Some normal voluntary muscle movement is a coordinated contraction of agonist and antagonistic muscles in a cooperative way to achieve a particular motion. In contrast to FIG. 23, and to illustrate the coordination of different muscle groups, in FIG. 24, the data in "EMG1-raw" and the data in "EMG2-raw" are from different electrodes associated with an agonist and antagonist muscle group, i.e., data from those muscles are superimposed upon each other. In some embodiments, the coordination of signals between electrodes on agonist and antagonist muscles may be used as a negative weighting factor for detection of a seizure. Often during seizures this coordination is lost. Instead, the muscles tend to lock up with muscles fighting each other. A good example of a scenario wherein coordination of agonist and antagonist muscles is lost may be seen in the tonic phase of a motor seizure when the biceps and triceps muscles are both stimulated. These muscles will fight each other with very high amplitude signals but the arms may not move much at all. That is, data traces from different electrodes where a phase relationship is maintained for some period of time may be evidence that an individual is not experiencing a seizure.

Example 5

Figure 25:
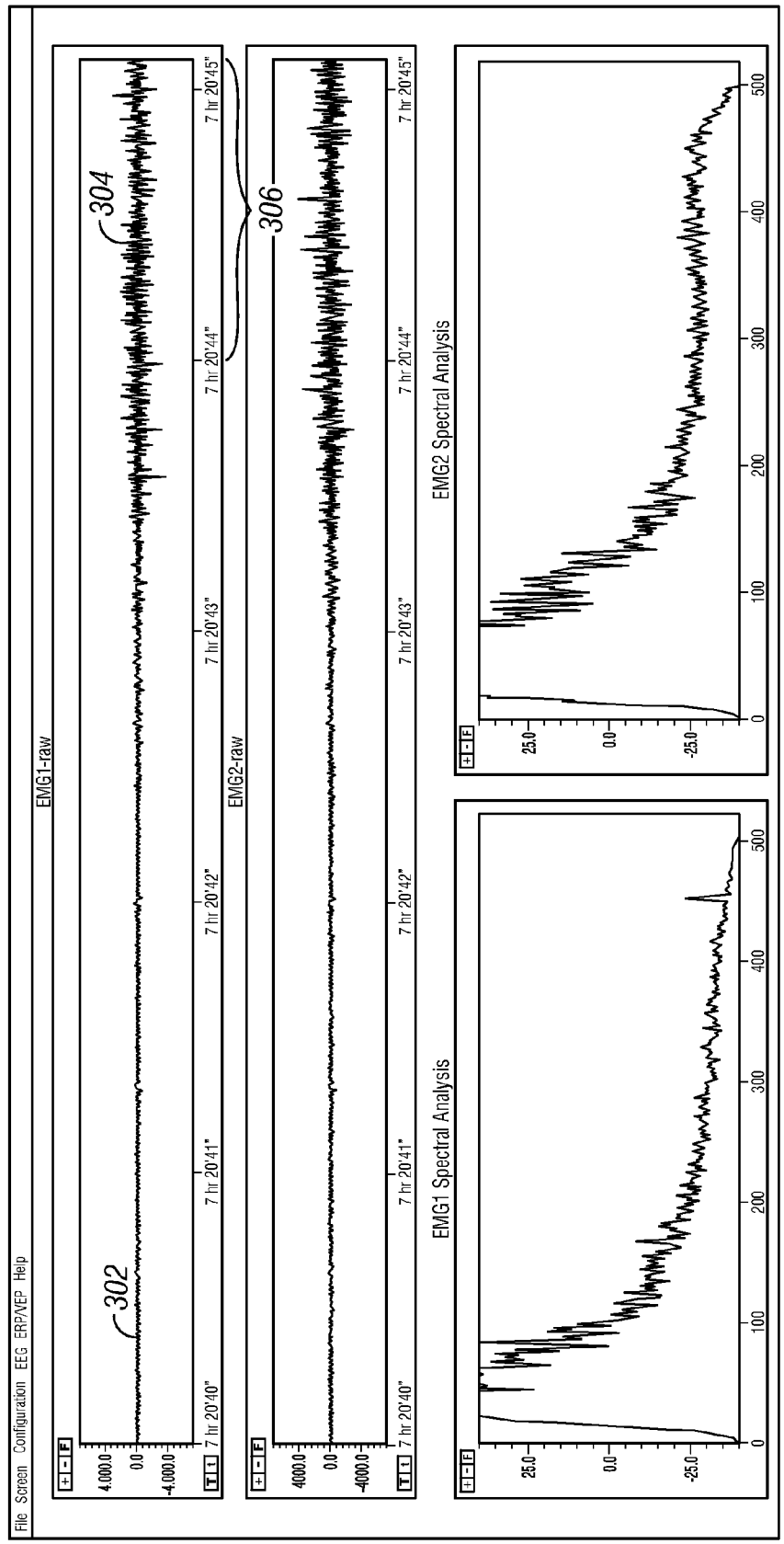
FIG. 25 illustrates exemplary EMG electrical data for a patient who is sleeping.
Figure 26:
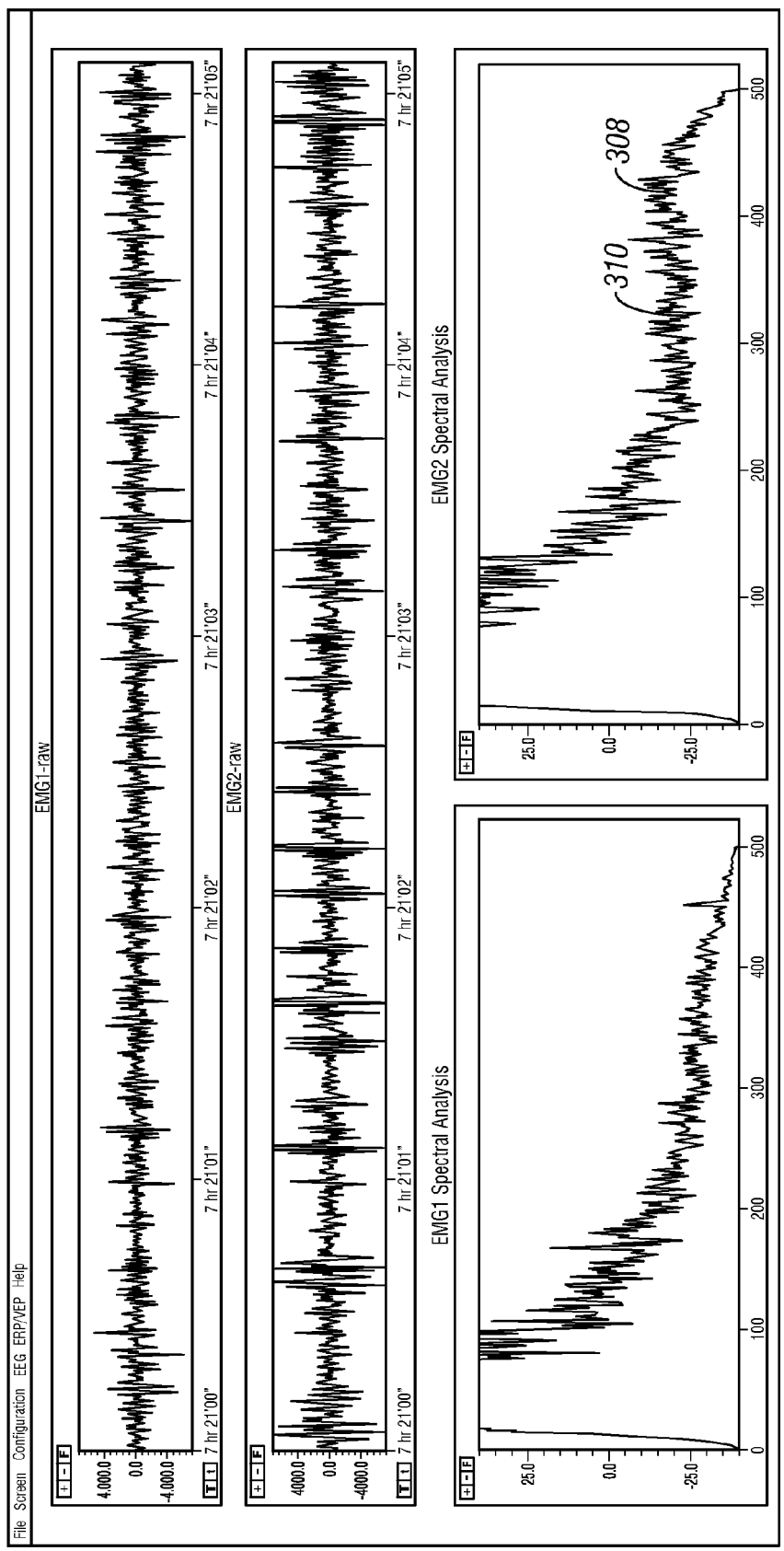
FIG. 26 illustrates exemplary EMG electrical data for a patient at the onset of a seizure.
Figure 27:
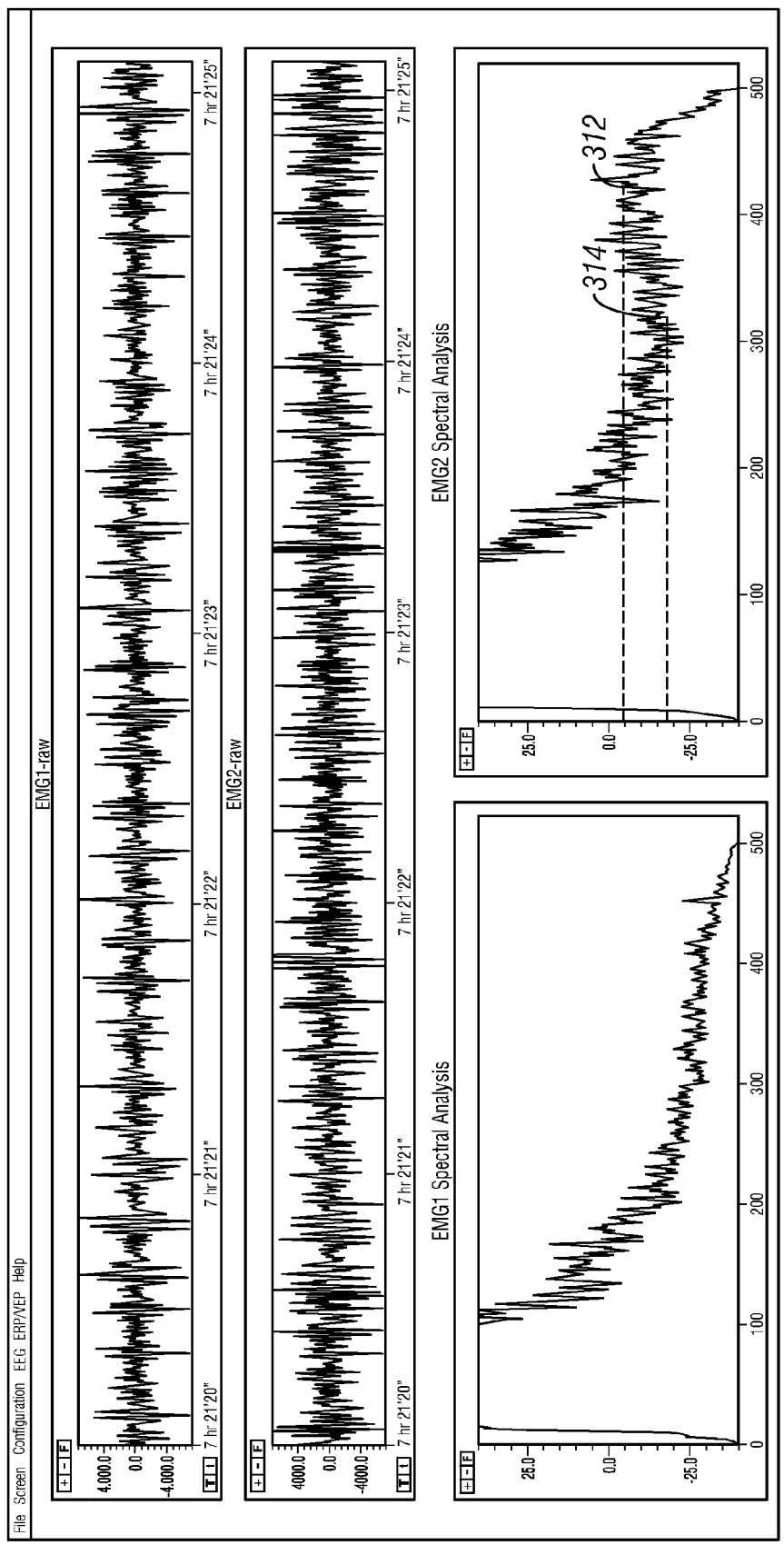
FIG. 27 illustrates exemplary EMG electrical data for a patient as the seizure progresses.

The data shown in FIGS. 25-27 are collectively indicative of how electrode data may change as patients transition from a non-seizure state to the experiencing of an actual seizure. FIG. 25 shows a relatively quiet time (from time approximately 7 h20'40" to approximately 7 h20'45") of EMG signals obtained during sleep just prior to a seizure. The spectral graph shows only relatively low frequency activity. The amplitude of electrode data at the far right of the time domain graph (later times), e.g., the amplitude at a point (304), is increased over data illustrated at earlier times, e.g., the amplitude at a point (302). That is, the amplitude of electrode data is increasing as the seizure approaches. In some embodiments, achieving a signal amplitude may trigger a change in state for an EMG electrode or initiate transfer of data between a detector and base unit and/or data storage unit. Changing states for detectors from sleep to active is discussed above. Achieving an amplitude at a point (304), or achieving such an amplitude with a certain frequency for data points over a certain period, e.g., such as a one second interval (306), may be used as a criteria that initiates the transfer of data between a detection unit and base unit and/or data archive.

FIG. 26 shows the EMG signals recorded during sleep at the onset of a seizure (showing time approximately 7 h21'00" to approximately 7 h21'05"). The two lower spectral graphs ("EMG 1 Spectral Analysis" and "EMG2 Spectral Analysis") show a minor "bump" (308) (with poor signal to noise) in the spectral display at the higher frequencies, between approximately 350-450 Hz, and a minor "slump" (310) in the spectral display at lower frequencies, between about 250-350 Hz. In brief, the data in FIG. 4 shows the beginning structure of a "GTC waveform," which is shown in FIG. 5 more clearly. However, at first, during a seizure, electrode data derived from muscles, e.g., muscles whose activity is in a process of building up, during a seizure may show the "GTC waveform" only poorly (if at all), and while the spectral density is greater at higher frequencies than typically seen for non-seizure data, such data, at the start of a seizure, may seem random or show only minor variations in spectral density across high frequency regions. Some electrical signals associated with normal voluntary muscle activity, recorded with macro-electrodes are almost entirely below 300 Hz. However, electrical frequencies recorded with macro-electrodes frequently extend above 300 Hz in a sustained manner during a seizure with motor manifestations. In some embodiments, the duration of time in which a threshold spectral density is achieved, e.g., at some high frequency, may be a seizure variable.

FIG. 27 shows the evolution of the EMG signals as the seizure progresses (showing time approximately 7 h21'20" to approximately 7 h21'25"). As may be seen in the bottom right spectral graph, which corresponds to the triceps electrode, the characteristic GTC waveform shows a region of elevated spectral density, i.e., a relatively high-frequency "bump" between approximately 300-500 Hz, and particularly around 400 Hz. That is, the spectral density at a point (312) in that region is elevated above the spectral density (314), e.g., within a "slumped" region, approximately located within a range of about 250 Hz to 350 Hz. The ratio of spectral density at the point (312) to the spectral density at the point (314), or slump to bump ratio, may be used as a seizure variable. In comparison of the spectral graph in FIGS. 26 and 27 it should be noted that as the patient begins to transition into a seizure that the GTC waveform changes. For example, a measurable slump to bump ratio becomes present in FIG. 27. As the ratio becomes measurable, a GTC detection register may become populated with an increasing value. If the GTC detection register becomes populated with a value that is greater than the leakage rate of the GTC accumulation register the value in the GTC accumulation register may increase over successive time periods.

In some embodiments, the slump to bump ratio may be used as a metric for detection of a GTC waveform. However, more advanced data analysis techniques, e.g., looking at a greater number of data points and/or advanced pattern recognition algorithms, may also be used to identify a GTC waveform. For example, in some embodiments a detection unit may include instructions for calculation of a slump to bump ratio and a base unit may calculate a slump to ratio and also corroborate the slump to bump calculation with more advanced pattern recognition analyses.

For this patient, the EMG data bursts have significant noise, i.e., large statistical fluctuations, at time points between them. Other patients may have less noise, resulting in GTC waveforms that are more clearly visible, and slump to bump ratios with greater signal to noise. A variety of analysis techniques may be used to improve the signal to noise for detection of a GTC waveform and/or slump to bump ratio. For example, in some embodiments, spectral data over a certain frequency range may be integrated, e.g., the area of the spectral curve within a frequency range of a "bump region" may be calculated. Also, the area of the curve within a frequency range of a "slump region" may be calculated. The specific ranges for slump to bump used for integration may be optimized for a given patient. That is, historical electrode data may be accessed from a data repository, different ranges for the slump region and/or the bump region may be selected, and different values for the slump to bump calculated for each selected ranges. Some slump to bump ratios, e.g., selected with some ranges, may show better S/N ratios and/or better correlation with the presence of a seizure than a slump to bump calculated with other ranges. That is, general seizure characteristics for the slump to bump ratio using frequency data in one range may prove to be more useful, i.e., show better correlation with the presence of a seizure, than a slump to bump ratio using another frequency range. Thus, a slump to bump seizure variable may be optimized for a given patient and may be updated periodically as historical data is collected for the patient.

In some embodiments, data in a predetermined frequency range, e.g., a range for a patient that typically shows a slump, may be smoothed and the local minimum in the data established. The area under a curve approximately centered on the local minimum may be calculated. Similarly, the algorithm may analyze data in another predetermined frequency range, e.g., a range for a patient that typically shows a bump. Data in that range may be smoothed, a local maximum established, and the area under the curve approximately centered on the local maximum may be calculated. The area under the local minimum, area under the local maximum, and ratio of those integrals may be used as seizure variables. In some embodiments, a detector unit may perform a calculation of the slump to bump ratio for a given portion of electrode data and a base station may perform more advanced pattern recognition techniques on the electrode data.

Example 6

Figure 28:
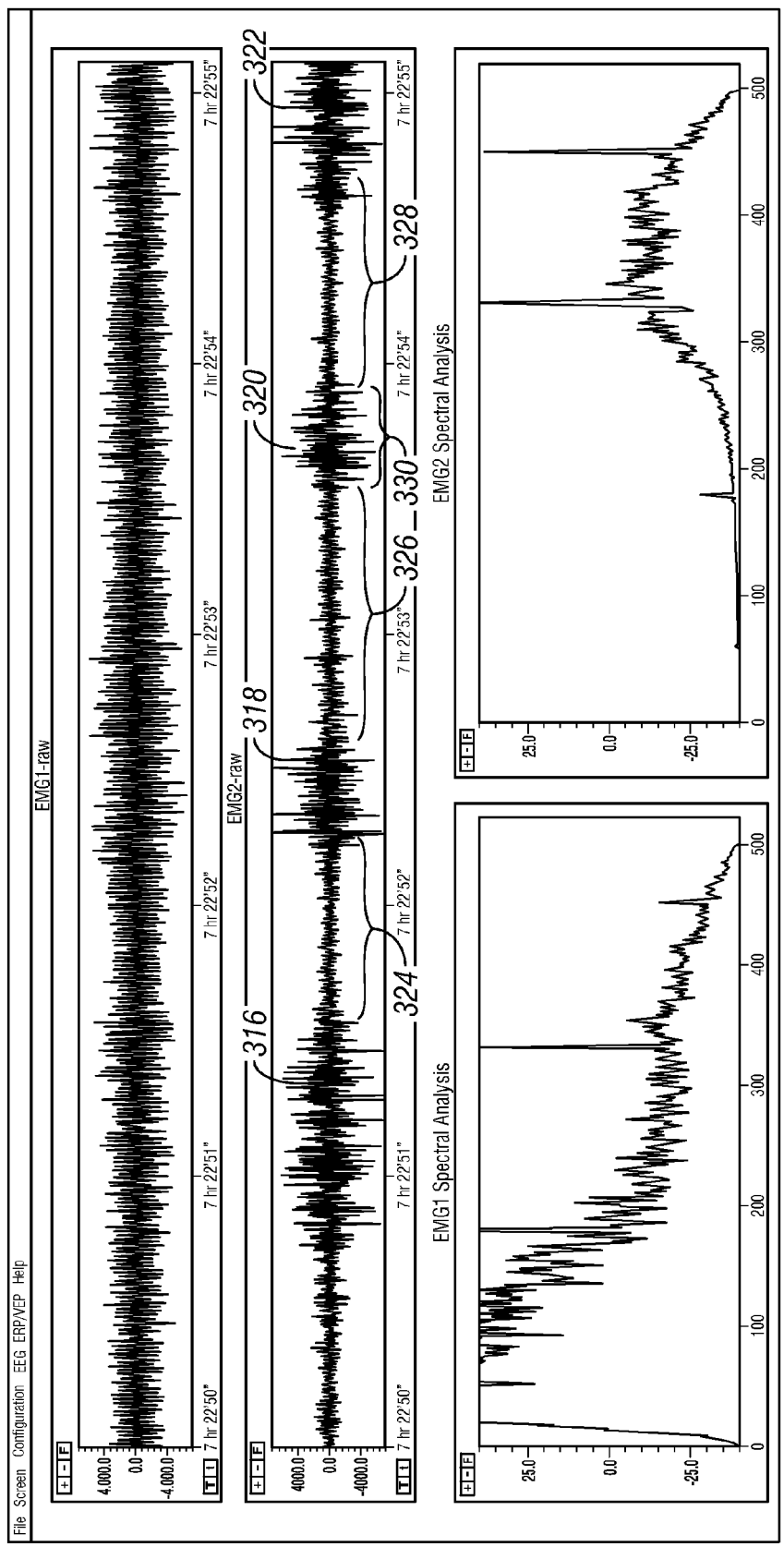
FIG. 28 illustrates exemplary EMG electrical data for a patient that has been filtered.

In Example 6, and associated FIGS. 28-31, some aspects of data filtering are described. FIG. 28 illustrates additional EMG data for the same patient also during a seizure. In this embodiment, the EMG 2 signal at time approximately 7 h22'50" to approximately 7 h22'55" has been filtered with a 3rd order Butterworth filter from 300 Hz to 500 Hz. When filtering is applied to the EMG 2 signal, the time domain data shows a series of bursts, i.e., regions of elevated EMG signal amplitude separated by lower amplitude signals, with high signal to noise. For example, at least four different burst regions (316, 318, 320, and 322) may be detected in the data of FIG. 28. The bursts shown in FIG. 28 may be categorized based upon the number of bursts, e.g., such as four, within a time window, the period between adjacent bursts (324, 326, and 328) and the time duration of a burst (330). Such burst features may be seizure variables. Referring now to the spectral graphs in FIG. 28, application of a high frequency filter in this embodiment, clearly illustrates the presence of high intensity frequency data. FIG. 28 also shows sharp, brief frequency "spikes" in the bottom two graphs. Those spikes may generally correspond to noise from overhead lighting at household frequency of 60 Hz, and may generally appear at 60 Hz harmonics. Such interferences may be recognized and an algorithm may include instructions to disregard such data signatures. Also, the EMG1 signal (biceps) shows sustained contraction (tonic activity), and the EMG2 signal (triceps) shows periodic contraction (clonic activity). Thus, and in contrast to the data illustrated in FIG. 27, such agonist and antagonist muscle groups do not necessarily have a correlated phase between them.

Figure 29:
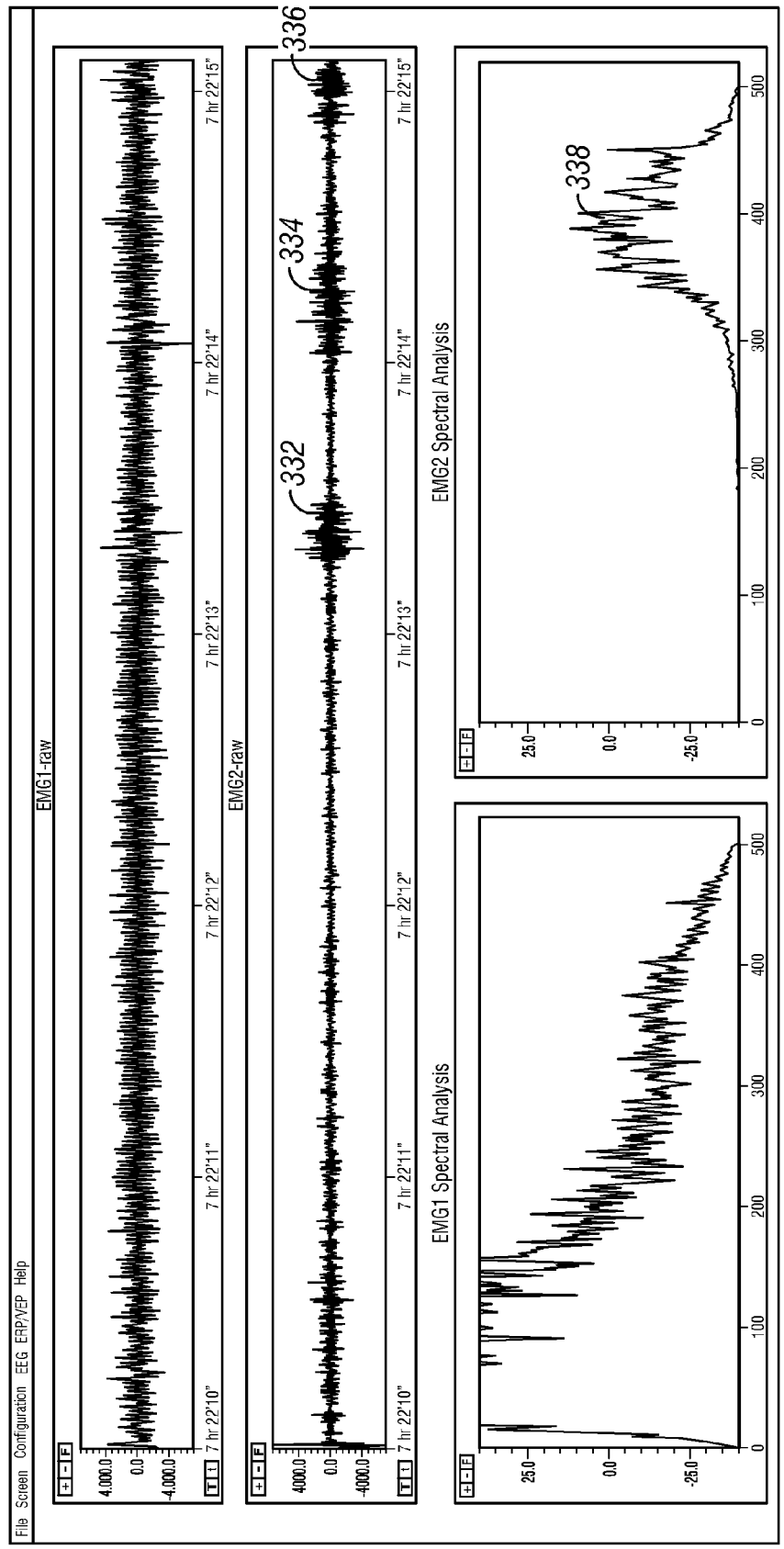
FIG. 29 illustrates further exemplary EMG electrical data for a patient that has also been filtered.

The lower right graph of FIG. 29 in particular shows even more dramatically how filtering from 350 Hz to 450 Hz, in the EMG 2 signal, can reveal bursts (332, 334, and 336) and high frequency information (338) out of the electrode signal (showing time approximately 7 h22'10" to approximately 7 h22'15"). The selection of a given filter may in some embodiments be adjusted for a given patient.

Figure 30:
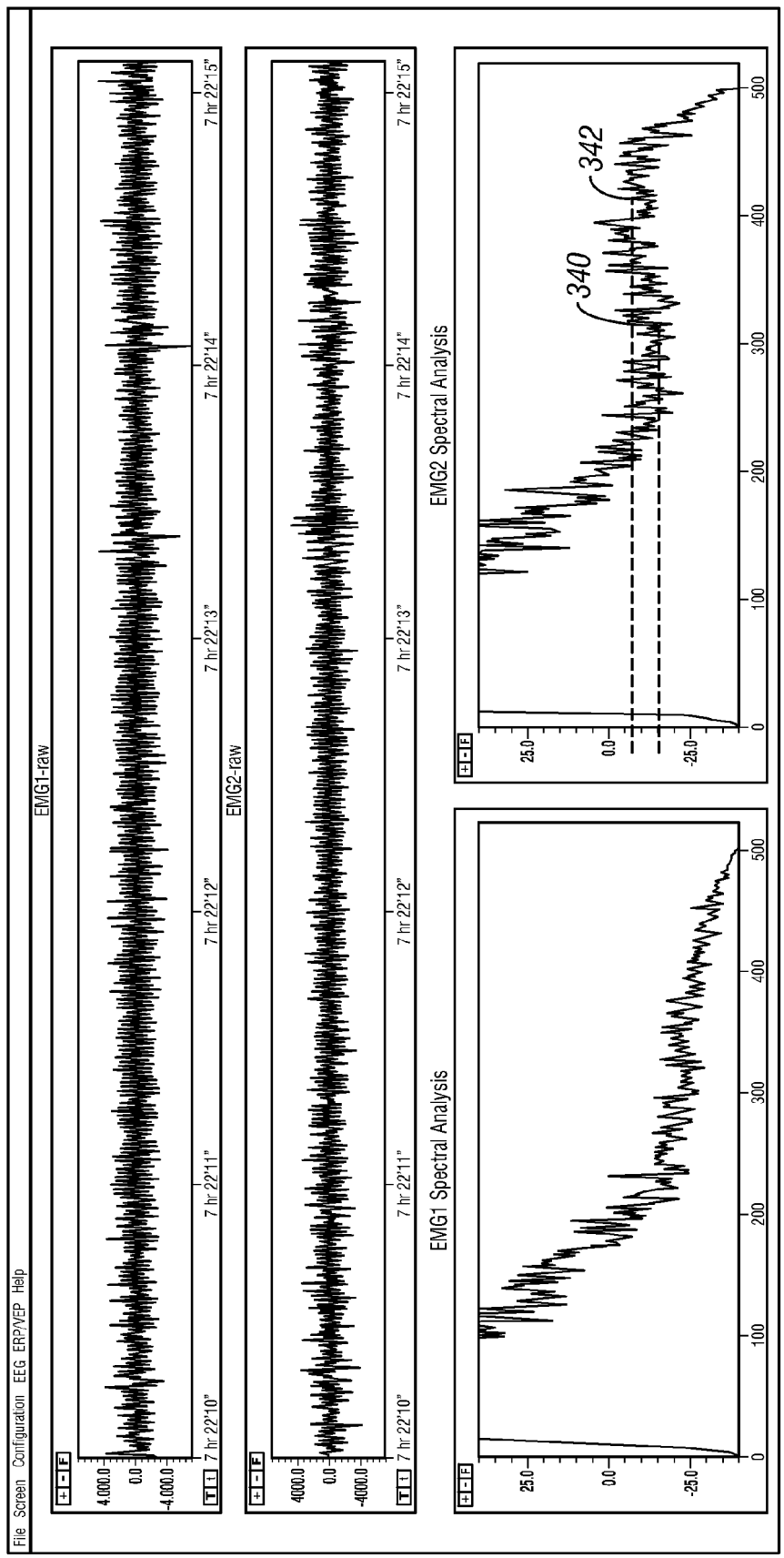
FIG. 30 illustrates the same exemplary EMG electrical data as shown in FIG. 29 and filtered using a different filter protocol.

FIG. 30 shows the exact same frame as FIG. 29, except the EMG 2 signal is unfiltered. It is evident from the spectral display that the lower frequencies have a higher amplitude as compared to the data in FIG. 29. Furthermore, bursts associated with the time domain data clearly have much lower signal to noise ratios. Based on the data in FIG. 29 and FIG. 30, it should be appreciated that electrode data may be filtered in any of various ways. The value of a given seizure variable may be determined from data collected using a filter that improves the signal to noise of the calculated value. For example, burst width and burst count may be collected from an electrode that uses a filter, such as a 3rd order Butterworth filter from 300 Hz to 500 Hz (FIG. 28) or a filter from 350 Hz to 450 Hz (FIG. 29). Other seizure variables, such as the slump to bump ratio of a GTC waveform may be collected without use of a filter or with another filter, such as one that passes a lower range of frequencies, as shown in FIG. 30. As shown in FIG. 30 a slump region (340) and a bump region (342) may be detected.

Figure 31:
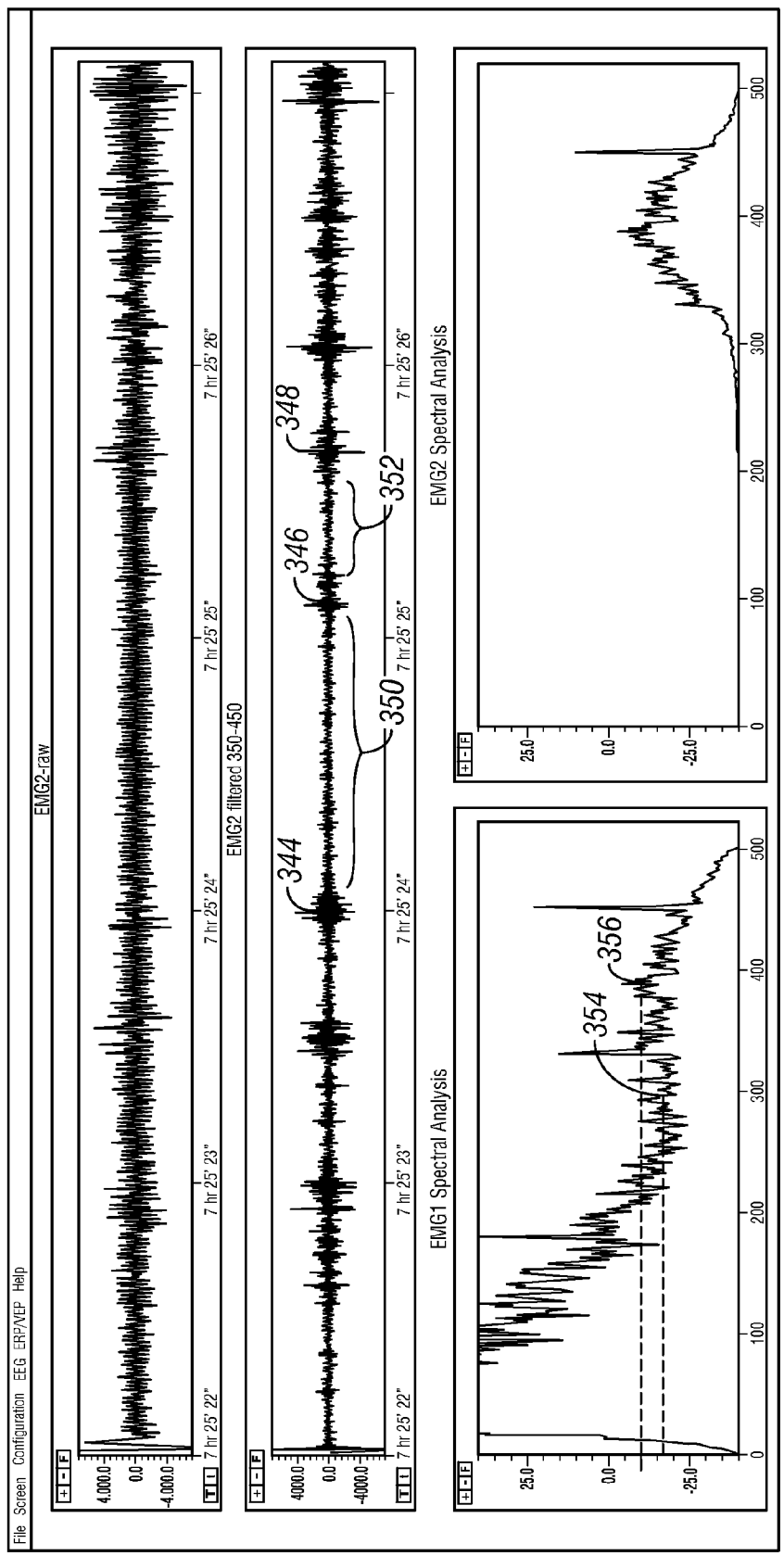
FIG. 31 illustrates exemplary EMG electrical data for a patient showing short-lived data events.

FIG. 31 provides another good example of increasing the discrimination of seizure bursts for the EMG 2 signal with respect to the noise (time approximately 7 h25'22" to approximately 7 h25'27"), e.g., increasing the signal to noise ratio of the spectral data by filtering the raw data. For example, representative burst (344) shows a high signal to noise ratio. Note the relative irregularity of the bursts (344, 346, and 348), as shown in the time domain data, which may be a factor that tends to indicate a seizure. That is, the periods between adjacent bursts, such as burst interval (350) and burst interval (352), have different values. In FIG. 31 the EMG 1 data, which has not been filtered, shows a characteristic GTC waveform, with a detectable slump (354) and bump (356).

Example 7

Figure 32:
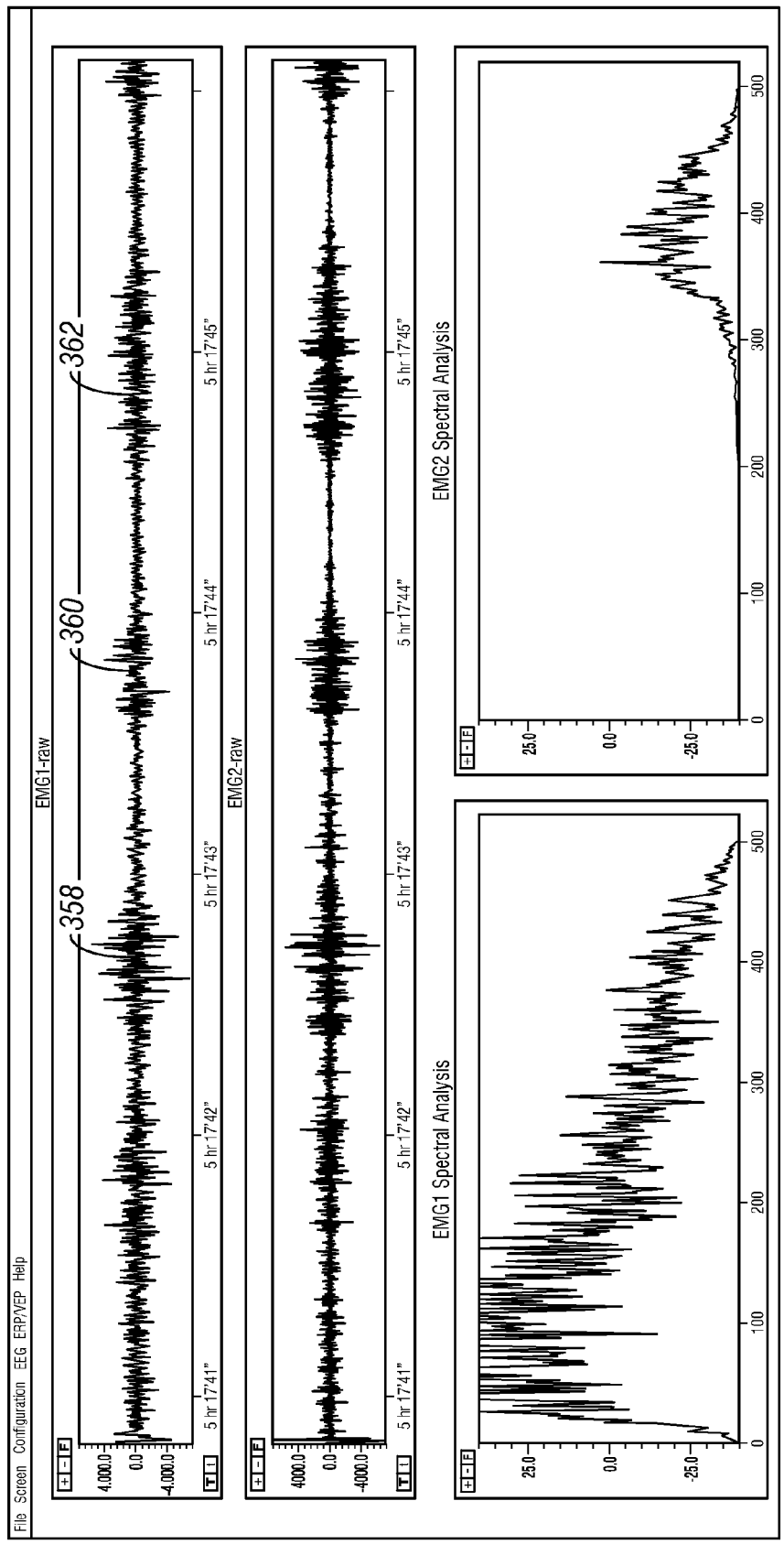
FIG. 32 illustrates still further exemplary EMG electrical data for a patient that has been filtered.
Figure 33:
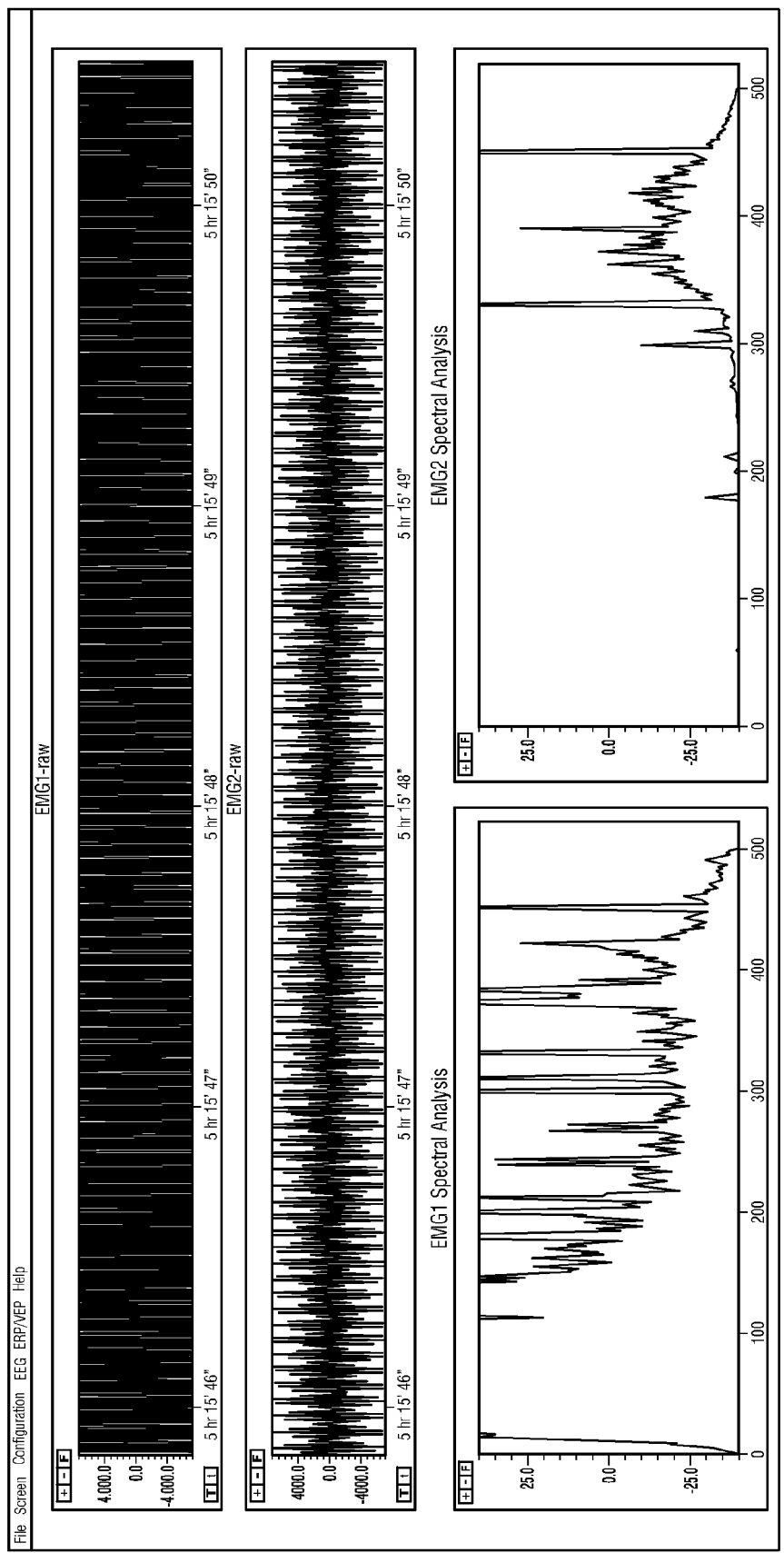
FIG. 33 illustrates exemplary EMG electrical data for a patient showing sustained signals.
Figure 34:
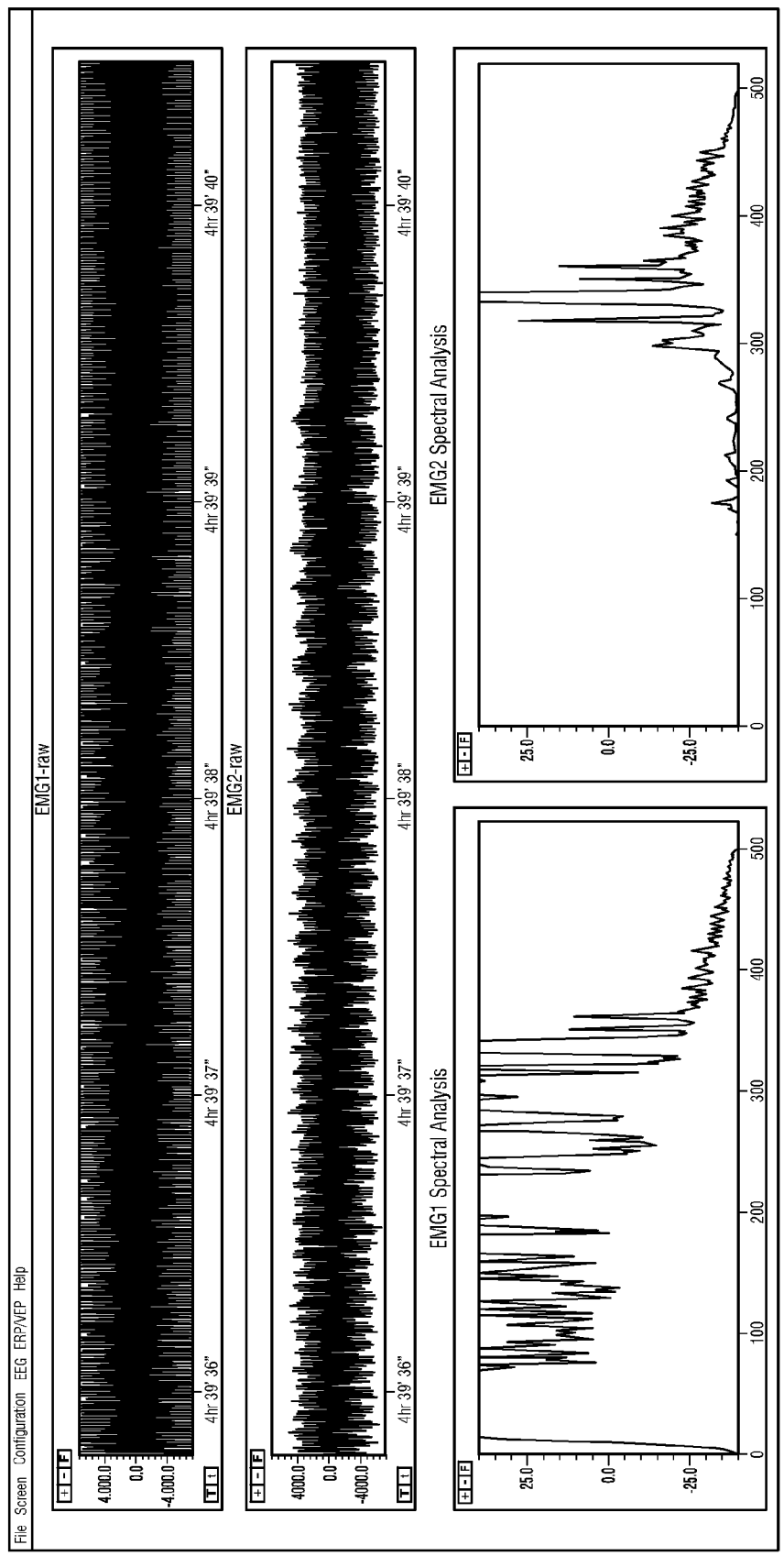
FIG. 34 illustrates another exemplary EMG electrical data for a patient that has been filtered.

In Example 7, and associated FIGS. 32-34, some aspects of data that may, for example, include features that may apply negative weighting to detection algorithm are discussed. FIG. 32 may indicate a short-lived seizure preceding the foregoing seizure (time approximately 5 h17'41" to approximately 5 h17'46"). Several bursts (358, 360, and 362) appear to have occurred, and are evident in both the EMG 1 and EMG 2 signals. Those bursts may be of relatively low concern due to their short duration. Some patients experience many of these short seizures. Comparison, of such short bursts with archived data, e.g., historical data for such patients, may be used to modify, e.g., a minimum burst detection width criteria. Thus, the algorithm may adapt to selectively neglect some data features, i.e., short and inconsequential bursts, and the algorithm may become better adapted to avoid initiation of unnecessary alarms.

FIG. 33 provides an example of high amplitude signals even after the EMG 2 signal has been filtered (time approximately 5 h15'46 to approximately 5 h15'51"). As the upper two waveforms show ("EMG1-raw" and "EMG2-raw"), the signals are highly uniform, a characteristic that may be detected and may be used to assess that the data may not indicate a seizure. The bursts are also very close together (the burst period is too small). Such a characteristic may also be detected and used to qualify the data and weigh against a determination that a seizure may be occurring. In some embodiments, either the signal uniformity or time period between regions of elevated amplitude may be used to disqualify data events or may be used to apply a negative weight to a seizure variable, e.g., amplitude bursts. Data that is highly uniform or has too short a period between data events may indicate an interfering signal, such as from a nearby electrical device. In real seizures, huge spikes at several discrete frequencies are rare or nonexistent. Again, historical data may be collected for a patient and analyzed. Coefficients may be adjusted to adapt the algorithm and avoid initiation of unnecessary alarms.

FIG. 34 (time approximately 4 h39'36" to approximately 4 h39'40") provides another example of sustained signals that may not trigger an alarm because they are too uniform and/or have too short a period between repeating data events. Such characteristics may be attributed to external noise and are typically not associated with a seizure.

Example 8

Figure 35:
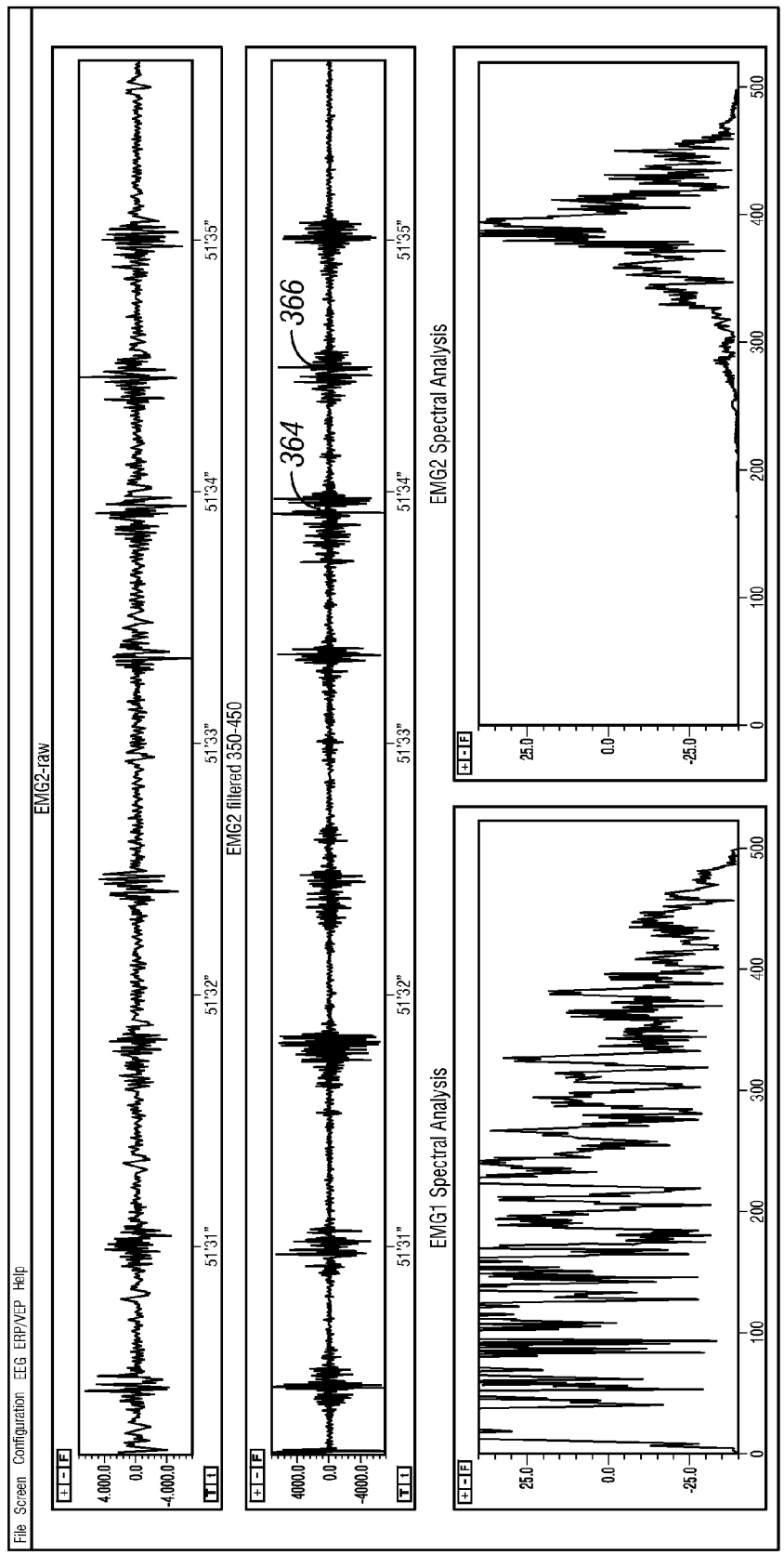
FIG. 35 illustrates another exemplary EMG electrical data for a patient.
Figure 36:
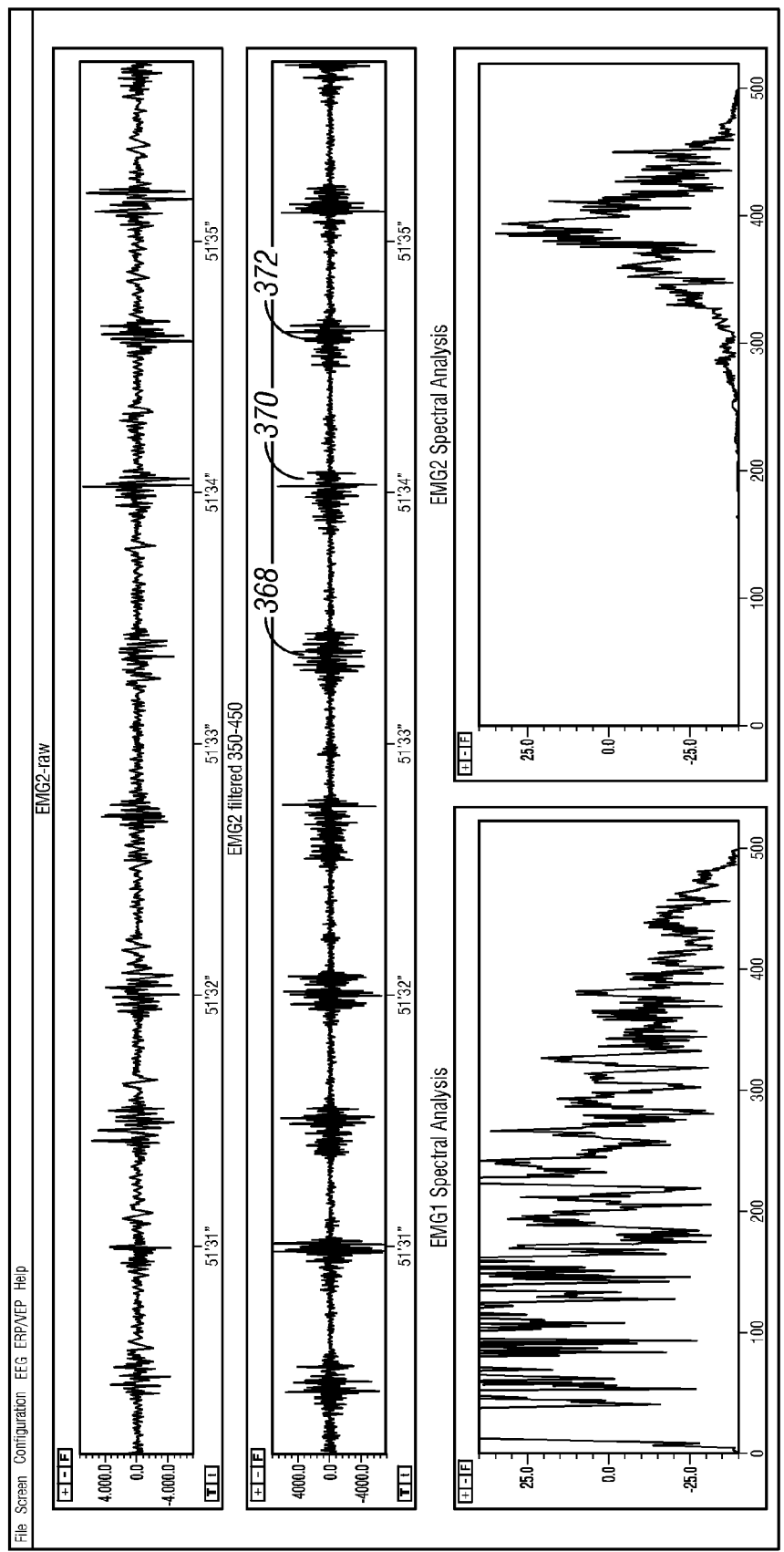
FIG. 36 illustrates yet another exemplary EMG electrical data.

In example 8, and associated FIGS. 35 and 36, data from another patient who exhibits data bursts is shown. Here, as well, a differential bipolar electrode with two inputs was placed over the person's biceps (graph not shown), and also over the persons triceps (upper graph labeled "EMG2-raw"). The vertical scale shows the amplitude of the signal. The middle graph (labeled "EMG2 filtered 350-450) shows the signal of the upper graph filtered to show 350-450 Hz frequencies. Note how well defined the bursts are, e.g., representative bursts (364) and (366), and how well the 350-450 Hz filtering works to reveal the characteristic GTC waveform, as seen in the middle graph and in the lower right graph (labeled "EMG2 Spectral Analysis"). The period of the bursts is fairly regular but not the same from burst to burst. In that light, it should be appreciated that while some seizures show fairly regular periodicity, real seizures are subject to fluctuations that are greater than some sources of noise, e.g., from man-made sources or from voluntary muscle activity. The balance between near perfect regularity for an artificial source of noise and the periodicity of burst trains may be balanced for an individual patient, such as by varying coefficients and threshold variables in a periodicity algorithm.

FIG. 36 continues the waveform of this patient, and shows how well ordered, but not completely uniform, a series of bursts (368, 370, and 372) may be. This pattern may be typical for some patients and may provide a very characteristic pattern that may be assigned very high weight in an algorithm.

Although the disclosed method and apparatus and their advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition, or matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods or steps.

We claim:

1. A system of apparatuses for monitoring a patient for seizure activity, the system comprising:
   one or more electromyography electrodes configured to provide an electromyography signal;
   a processor configured to receive the electromyography signal and process the electromyography signal to detect bursts characteristic of seizure activity based on whether regions of the electromyography signal meet criteria suitable to be qualified as bursts, including a comparison of criteria values to thresholds;

wherein said criteria values include a duration width and one or more of a signal-to-noise ratio and an amplitude;

wherein said thresholds include a minimum duration width, a maximum duration width, and one or more of a minimum signal-to-noise ratio, minimum amplitude, and maximum amplitude; and wherein said processor is configured to determine a detected burst count and include said detected burst count in a determination of whether to send an alert indicating detection of said seizure activity to one or more remote devices.

2. The system of claim 1 wherein said processor is further configured to assign certainty weight values to bursts included among said detected burst count.

3. The system of claim 1 wherein said processor is further configured to determine a periodicity contribution based on a regularity of time periods between bursts and include said periodicity contribution in the determination whether to send said alert.

4. The system of claim 1 further comprising a base station in communication with said processor, wherein said one or more remote devices include said base station;

wherein said one or more electromyography electrodes and said processor are packaged as a single unit mountable to said patient and physically separate from said base station; and wherein said base station is configured for receiving the alert and a transmitted portion of the electromyography signal, independently processing the transmitted portion of the electromyography signal to determine whether a seizure may be occurring, and generating an alarm if a seizure is detected.

5. The system of claim 4 wherein the base station is configured to select one or more of a plurality of pre-generated templates including base station threshold settings to determine whether a seizure is detected.

6. The system of claim 4 wherein the base station is configured to select base station threshold settings used to determine whether a seizure is detected that are based upon a location of the patient.

7. The system of claim 4 further comprising one or more environmental transceivers; and wherein said one or more environmental transceivers are configured to transmit to said base station information about a location of the patient.

8. The system of claim 1 wherein said processor is further configured to wirelessly transmit a compressed form of burst data to a base station; and wherein said base station is configured to use the compressed form of burst data to determine whether a seizure is detected using pre-defined base station threshold settings.

9. A method for monitoring a patient for seizure activity, the method comprising:

collecting an electromyography signal from the patient using one or more electromyography electrodes;

processing with one or more processors the electromyography signal to detect bursts characteristic of seizure activity based on whether regions of the electromyography signal meet criteria suitable to be qualified as said bursts, including a comparison of criteria values to thresholds;

wherein said criteria values include a duration width and one or more of a signal-to-noise ratio and an amplitude;

wherein said thresholds include a minimum duration width, a maximum duration width, and one or more of a minimum signal-to-noise ratio, minimum amplitude, and maximum amplitude;

determining a detected burst count; and weighting said detected burst count in determining whether to send an alert indicating detection of said seizure activity to one or more remote devices.

10. The method of claim 9 further comprising assigning certainty weight values to bursts including among said detected burst count.

11. The method of claim 9 further comprising determining a periodicity contribution based on a regularity of time periods between bursts and weighting said periodicity contribution together with the weighting of said detected burst count in determining whether to send said alert.

12. The method of claim 11 wherein the periodicity contribution negatively weights the determination of whether to send said alert when time periods between bursts are too regular to be indicative of seizure activity.

13. A method of monitoring a patient for seizure activity comprising:

collecting an electromyography signal from the patient using one or more electromyography electrodes;

processing with a processor the electromyography signal to detect bursts, assign certainty values to individual bursts among said detected bursts, and determine a burst count contribution to seizure detection based on a number of said detected bursts weighted as a function of the certainty values assigned to said individual bursts;

wherein said certainty values are based on how well one or more characteristics of the individual bursts compare to one or more reference burst characteristics;

said one or more characteristics selected from a group of characteristics including burst signal-to-noise ratio, burst duration width, and burst amplitude;

wherein burst detection includes determining the presence of bursts based on whether regions of the electromyography signal meet criteria suitable to be qualified as bursts, including a comparison of criteria values to thresholds;

wherein said criteria values include a duration width and one or more of a signal-to-noise ratio and an amplitude;

wherein said thresholds include a minimum duration width, a maximum duration width, and one or more of a minimum signal-to-noise ratio, minimum amplitude, and maximum amplitude;

including said burst count contribution into an algorithm to determine whether a seizure is occurring; and initiating an alert if a seizure is occurring.

14. The method of claim 13 further comprising identifying the presence of a plurality of bursts over a time period, determining a periodicity of bursts over said time period, determining a periodicity contribution to seizure detection, and including said periodicity contribution in determining whether a seizure is detected;

monitoring a location of the patient based on a detected location of the patient using one or more environmental transceivers; and wherein said thresholds are included in a template file selected from among a plurality of pre-generated template files, the template file selected based on a patient location as determined by the monitoring of the patient location using said one or more environmental transceivers.

15. A method for reviewing patient electromyography data, the method comprising:

downloading from a computer memory an electromyography signal, the signal collected using one or more electromyography electrodes disposed on a patient while monitoring the patient during one or more monitoring periods;

processing with a processor the electromyography signal to detect bursts, assign certainty values to individual bursts among said detected bursts, and determine a burst count contribution to seizure detection based on a number of said detected bursts weighted as a function of the certainty values assigned to said individual bursts;

wherein said certainty values are based on how well one or more characteristics of the individual bursts compare to one or more reference burst characteristics;

said one or more characteristics selected from a group of characteristics including burst signal-to-noise ratio, burst duration width, and burst amplitude;

wherein burst detection includes determining the presence of bursts based on whether regions of the electromyography signal meet criteria suitable to be qualified as bursts, including a comparison of criteria values to thresholds;

wherein said criteria values include a duration width and one or more of a signal-to-noise ratio and an amplitude;

wherein said thresholds include a minimum duration width, a maximum duration width, and one or more of a minimum signal-to-noise ratio, minimum amplitude, and maximum amplitude;

including said burst count contribution into an algorithm to determine whether a seizure is occurring; and initiating an alert if a seizure is occurring.

* * * * *